United States Patent
Gilmore et al.

(10) Patent No.: US 9,693,865 B2
(45) Date of Patent: Jul. 4, 2017

(54) SOFT TISSUE DEPTH-FINDING TOOL

(71) Applicant: 4 TECH INC., Waltham, MA (US)

(72) Inventors: Michael Gilmore, Rathbane (IE);
Charlotte Murphy, Turlough (IE);
Idan Tobis, Beth Hashmonai (IL)

(73) Assignee: 4 TECH INC., Waltham, MA (US)

( * ) Notice: Subject to any disclaimer, the term of this patent is extended or adjusted under 35 U.S.C. 154(b) by 0 days.

(21) Appl. No.: 15/264,250

(22) Filed: Sep. 13, 2016

(65) Prior Publication Data

US 2017/0000611 A1    Jan. 5, 2017

Related U.S. Application Data

(63) Continuation of application No. 14/759,768, filed as application No. PCT/IL2014/050027 on Jan. 9, 2014.
(Continued)

(51) Int. Cl.
*A61B 17/08* (2006.01)
*A61F 2/24* (2006.01)
(Continued)

(52) U.S. Cl.
CPC ........ *A61F 2/2487* (2013.01); *A61B 17/0401* (2013.01); *A61F 2/2478* (2013.01);
(Continued)

(58) Field of Classification Search
CPC ............ A61F 2/2478; A61F 2230/0091; A61F 2220/0016; A61N 1/0573; A61B 2017/0443; A61B 2017/0464; A61B 17/08
See application file for complete search history.

(56) References Cited

U.S. PATENT DOCUMENTS 4,214,349 A    7/1980 Munch
4,405,313 A    9/1983 Sisley et al.
(Continued)

FOREIGN PATENT DOCUMENTS

DE    102007043830    4/2009
EP    1568326    8/2005
(Continued)

OTHER PUBLICATIONS

An International Search Report and a Written Opinion both dated Dec. 6, 2013, which issued during the prosecution of Applicant's PCT/IL2013/050470.
(Continued)

*Primary Examiner* — Victor Nguyen
(74) *Attorney, Agent, or Firm* — Sughrue Mion, PLLC

(57) ABSTRACT

Apparatus is provided that includes a tissue anchor, which (a) includes a helical tissue-coupling element which has a distal tissue-penetrating tip at a distal end of the tissue anchor, and is configured to be advanced into soft tissue, and (b) is shaped so as to define a longitudinal channel extending to the distal end of the tissue anchor. The apparatus further includes (a) a depth-finding tool, which includes a radiopaque bead, which is shaped so as to define a hole therethrough, and which is positioned within and axially moveable along the channel so as to serve as a marker indicating a depth of penetration of the tissue-coupling element into the soft tissue, and (b) a shaft that is removably positioned within the channel, such that the shaft passes through the hole of the bead, and such that the bead is axially moveable along the shaft and along the channel.

11 Claims, 17 Drawing Sheets

Related U.S. Application Data

(60) Provisional application No. 61/750,427, filed on Jan. 9, 2013.

(51) Int. Cl.
*A61N 1/05* (2006.01)
*A61B 17/04* (2006.01)
*A61B 17/064* (2006.01)
*A61B 90/00* (2016.01)

(52) U.S. Cl.
CPC .... *A61N 1/0573* (2013.01); *A61B 2017/0443* (2013.01); *A61B 2017/0464* (2013.01); *A61B 2017/0649* (2013.01); *A61B 2090/062* (2016.02); *A61F 2220/0016* (2013.01); *A61F 2230/0091* (2013.01)

(56) References Cited

U.S. PATENT DOCUMENTS

| | | |
|---|---|---|
| 4,423,525 A | 1/1984 | Vallana |
| 4,444,207 A | 4/1984 | Robicsek |
| 4,493,329 A | 1/1985 | Crawford et al. |
| 4,532,926 A | 8/1985 | O'Holla |
| 4,548,202 A | 10/1985 | Duncan |
| 4,602,911 A | 7/1986 | Ahmadi et al. |
| 4,625,727 A | 12/1986 | Leiboff |
| 4,712,549 A | 12/1987 | Peters et al. |
| 4,741,336 A | 5/1988 | Failla et al. |
| 4,778,468 A | 10/1988 | Hunt et al. |
| 4,808,157 A | 2/1989 | Coombs |
| 4,853,986 A | 8/1989 | Allen |
| 5,108,420 A | 4/1992 | Marks |
| 5,330,521 A | 7/1994 | Cohen |
| 5,336,233 A | 8/1994 | Chen |
| 5,350,399 A | 9/1994 | Erlebacher et al. |
| 5,450,860 A | 9/1995 | O'Connor |
| 5,473,812 A | 12/1995 | Morris et al. |
| 5,474,518 A | 12/1995 | Farrer-Velazquez |
| 5,702,343 A | 12/1997 | Alferness |
| 5,776,178 A | 7/1998 | Pohndorf et al. |
| 5,792,400 A | 8/1998 | Talja et al. |
| 5,843,120 A | 12/1998 | Israel |
| 5,843,164 A | 12/1998 | Frantzen et al. |
| 5,904,697 A | 5/1999 | Gifford et al. |
| 5,948,000 A | 9/1999 | Larsen et al. |
| 5,957,953 A | 9/1999 | DiPoto et al. |
| 5,961,440 A | 10/1999 | Schweich, Jr. et al. |
| 6,010,113 A | 1/2000 | Rotering |
| 6,027,523 A | 2/2000 | Schmieding |
| 6,045,497 A | 4/2000 | Schweich, Jr. et al. |
| 6,050,936 A | 4/2000 | Schweich, Jr. et al. |
| 6,077,214 A | 6/2000 | Mortier et al. |
| 6,183,512 B1 | 2/2001 | Howanec, Jr. et al. |
| 6,193,734 B1 | 2/2001 | Bolduc et al. |
| 6,206,913 B1 | 3/2001 | Yencho et al. |
| 6,210,432 B1 | 4/2001 | Solem et al. |
| 6,231,516 B1 | 5/2001 | Keilman et al. |
| 6,260,552 B1 | 7/2001 | Mortier et al. |
| 6,298,272 B1 | 10/2001 | Peterfeso et al. |
| 6,299,635 B1 | 10/2001 | Frantzen |
| 6,332,893 B1 | 12/2001 | Mortier et al. |
| 6,338,738 B1 | 1/2002 | Bellotti et al. |
| 6,402,780 B2 | 6/2002 | Williamson, IV et al. |
| 6,402,781 B1 | 6/2002 | Langberg et al. |
| 6,406,420 B1 | 6/2002 | McCarthy et al. |
| 6,461,336 B1 | 10/2002 | Larre |
| 6,533,810 B2 | 3/2003 | Hankh et al. |
| 6,537,198 B1 | 3/2003 | Vidlund et al. |
| 6,537,314 B2 | 3/2003 | Langberg et al. |
| 6,575,976 B2 | 6/2003 | Grafton |
| 6,585,766 B1 | 7/2003 | Huynh et al. |
| 6,602,288 B1 | 8/2003 | Cosgrove et al. |
| 6,613,078 B1 | 9/2003 | Barone |
| 6,613,079 B1 | 9/2003 | Wolinsky |
| 6,616,684 B1 | 9/2003 | Vidlund et al. |
| 6,619,291 B2 | 9/2003 | Hlavka et al. |
| 6,622,730 B2 | 9/2003 | Ekvall et al. |
| 6,626,899 B2 | 9/2003 | Houser et al. |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,641,597 B2 | 11/2003 | Burkhart et al. |
| 6,645,193 B2 | 11/2003 | Mangosong |
| 6,669,687 B1 | 12/2003 | Saadat |
| 6,695,768 B1 | 2/2004 | Levine et al. |
| 6,702,846 B2 | 3/2004 | Mikus |
| 6,709,456 B2 | 3/2004 | Langberg et al. |
| 6,718,985 B2 | 4/2004 | Hlavka et al. |
| 6,719,767 B1 | 4/2004 | Kimblad |
| 6,723,038 B1 | 4/2004 | Schroeder et al. |
| 6,730,118 B2 | 5/2004 | Spenser et al. |
| 6,743,198 B1 | 6/2004 | Tihon |
| 6,746,472 B2 | 6/2004 | Frazier et al. |
| 6,764,510 B2 | 7/2004 | Vidlund et al. |
| 6,776,754 B1 | 8/2004 | Wilk |
| 6,797,001 B2 | 9/2004 | Mathis |
| 6,810,882 B2 | 11/2004 | Langberg et al. |
| 6,884,250 B2 | 4/2005 | Monassevitch |
| 6,893,459 B1 | 5/2005 | Macoviak |
| 6,908,478 B2 | 6/2005 | Alferness et al. |
| 6,929,660 B1 | 8/2005 | Ainsworth et al. |
| 6,989,028 B2 | 1/2006 | Lashinski et al. |
| 6,997,951 B2 | 2/2006 | Solem et al. |
| 7,011,682 B2 | 3/2006 | Lashinski et al. |
| 7,018,406 B2 | 3/2006 | Seguin et al. |
| 7,018,408 B2 | 3/2006 | Bailey et al. |
| 7,037,290 B2 | 5/2006 | Gardeski et al. |
| 7,041,097 B1 | 5/2006 | Webler |
| 7,044,967 B1 | 5/2006 | Solem et al. |
| 7,063,711 B1 | 6/2006 | Loshakove et al. |
| 7,077,861 B2 | 7/2006 | Spence |
| 7,083,628 B2 | 8/2006 | Bachman |
| 7,087,064 B1 | 8/2006 | Hyde |
| 7,094,244 B2 | 8/2006 | Schreck |
| 7,101,395 B2 | 9/2006 | Tremulis et al. |
| 7,101,396 B2 | 9/2006 | Artof et al. |
| 7,112,219 B2 | 9/2006 | Vidlund et al. |
| 7,125,421 B2 | 10/2006 | Tremulis et al. |
| 7,144,363 B2 | 12/2006 | Pai et al. |
| 7,159,593 B2 | 1/2007 | McCarthy et al. |
| 7,166,127 B2 | 1/2007 | Spence et al. |
| 7,169,187 B2 | 1/2007 | Datta |
| 7,175,625 B2 | 2/2007 | Culbert |
| 7,179,282 B2 | 2/2007 | Alferness et al. |
| 7,186,262 B2 | 3/2007 | Saadat |
| 7,189,199 B2 | 3/2007 | McCarthy et al. |
| 7,192,442 B2 | 3/2007 | Solem et al. |
| 7,192,443 B2 | 3/2007 | Solem et al. |
| 7,198,646 B2 | 4/2007 | Figulla et al. |
| 7,201,772 B2 | 4/2007 | Schwammenthal |
| 7,211,107 B2 | 5/2007 | Bruckheimer et al. |
| 7,211,110 B2 | 5/2007 | Rowe et al |
| 7,241,257 B1 | 7/2007 | Ainsworth et al. |
| 7,247,134 B2 | 7/2007 | Vidlund et al. |
| 7,258,697 B1 | 8/2007 | Cox et al. |
| 7,291,168 B2 | 11/2007 | Macoviak et al. |
| 7,311,697 B2 | 12/2007 | Osborne |
| 7,311,728 B2 | 12/2007 | Solem et al. |
| 7,316,706 B2 | 1/2008 | Bloom et al. |
| 7,316,710 B1 | 1/2008 | Cheng et al. |
| 7,329,279 B2 | 2/2008 | Haug et al. |
| 7,331,972 B1 | 2/2008 | Cox |
| 7,335,213 B1 | 2/2008 | Hyde et al. |
| 7,338,506 B2 | 3/2008 | Caro |
| 7,351,256 B2 | 4/2008 | Hojeibane |
| 7,371,244 B2 | 5/2008 | Chatlynne et al. |
| 7,374,573 B2 | 5/2008 | Gabbay |
| 7,381,210 B2 | 6/2008 | Zarbatany et al. |
| 7,381,220 B2 | 6/2008 | Macoviak et al. |
| 7,390,329 B2 | 6/2008 | Westra et al. |
| 7,431,692 B2 | 10/2008 | Zollinger et al. |
| 7,431,726 B2 | 10/2008 | Spence et al. |
| 7,485,143 B2 | 2/2009 | Webler et al. |

(56) References Cited

U.S. PATENT DOCUMENTS

| | | |
|---|---|---|
| 7,500,989 B2 | 3/2009 | Solem et al. |
| 7,503,931 B2 | 3/2009 | Kowalsky et al. |
| 7,510,575 B2 | 3/2009 | Spenser et al. |
| 7,527,646 B2 | 5/2009 | Rahdert et al. |
| 7,530,995 B2 | 5/2009 | Quijano et al. |
| 7,547,321 B2 | 6/2009 | Silvestri et al. |
| 7,549,983 B2 | 6/2009 | Roue et al. |
| 7,597,703 B2 | 10/2009 | Sater |
| 7,608,102 B2 | 10/2009 | Adams et al. |
| 7,618,449 B2 | 11/2009 | Tremulis et al. |
| 7,628,797 B2 | 12/2009 | Tieu et al. |
| 7,632,303 B1 | 12/2009 | Stalker et al. |
| 7,637,946 B2 | 12/2009 | Solem et al. |
| 7,666,204 B2 | 2/2010 | Thornton et al. |
| 7,695,512 B2 | 4/2010 | Lashinski et al. |
| 7,704,277 B2 | 4/2010 | Zakay et al. |
| 7,722,523 B2 | 5/2010 | Mortier et al. |
| 7,758,632 B2 | 7/2010 | Hojeibane et al. |
| 7,771,467 B2 | 8/2010 | Svensson |
| 7,780,726 B2 | 8/2010 | Seguin |
| 7,785,366 B2 | 8/2010 | Maurer et al. |
| 7,803,187 B2 | 9/2010 | Hauser |
| 7,806,910 B2 | 10/2010 | Anderson |
| 7,837,727 B2 | 11/2010 | Goetz et al. |
| 7,841,502 B2 | 11/2010 | Walberg et al. |
| 7,857,846 B2 | 12/2010 | Alferness et al. |
| 7,871,433 B2 | 1/2011 | Lattouf |
| 7,883,539 B2 | 2/2011 | Schweich, Jr. et al. |
| 7,942,927 B2 | 5/2011 | Kaye et al. |
| 7,947,207 B2 | 5/2011 | Mcniven et al. |
| 7,972,378 B2 | 7/2011 | Tabor et al. |
| 7,991,484 B1 | 8/2011 | Sengupta et al. |
| 7,992,567 B2 | 8/2011 | Hirotsuka |
| 7,993,368 B2 | 8/2011 | Gambale et al. |
| 7,993,397 B2 | 8/2011 | Lashinski et al. |
| 8,010,207 B2 | 8/2011 | Smits et al. |
| 8,025,495 B2 | 9/2011 | Hardert et al. |
| 8,029,518 B2 | 10/2011 | Goldfarb et al. |
| 8,052,592 B2 | 11/2011 | Goldfarb et al. |
| 8,075,616 B2 | 12/2011 | Solem et al. |
| 8,092,520 B2 | 1/2012 | Quadri |
| 8,092,525 B2 | 1/2012 | Eliasen et al. |
| 8,100,820 B2 | 1/2012 | Hauser et al. |
| 8,108,054 B2 | 1/2012 | Helland |
| 8,109,996 B2 | 2/2012 | Stacchino et al. |
| 8,137,381 B2 | 3/2012 | Foerster et al. |
| 8,142,493 B2 | 3/2012 | Spence et al. |
| 8,142,495 B2 | 3/2012 | Hasenkam et al. |
| 8,147,542 B2 | 4/2012 | Maisano et al. |
| 8,157,810 B2 | 4/2012 | Case et al. |
| 8,172,898 B2 | 5/2012 | Alferness et al. |
| 8,197,441 B2 | 6/2012 | Webler et al. |
| 8,202,281 B2 | 6/2012 | Voss |
| 8,202,315 B2 | 6/2012 | Hlavka et al. |
| 8,216,302 B2 | 7/2012 | Wilson et al. |
| 8,226,707 B2 | 7/2012 | White |
| 8,236,013 B2 | 8/2012 | Chu |
| 8,236,049 B2 | 8/2012 | Rowe et al. |
| 8,252,005 B2 | 8/2012 | Findlay et al. |
| 8,262,567 B2 | 9/2012 | Sharp et al. |
| 8,262,724 B2 | 9/2012 | Seguin et al. |
| 8,262,725 B2 | 9/2012 | Subramanian |
| 8,267,981 B2 | 9/2012 | Boock et al. |
| 8,313,497 B2 | 11/2012 | Walberg et al. |
| 8,313,498 B2 | 11/2012 | Pantages et al. |
| 8,323,312 B2 | 12/2012 | Clark |
| 8,323,335 B2 | 12/2012 | Rowe et al. |
| 8,332,051 B2 | 12/2012 | Sommer et al. |
| 8,361,088 B2 | 1/2013 | McIntosh |
| 8,382,829 B1 | 2/2013 | Call et al. |
| 8,398,672 B2 | 3/2013 | Kleshinski et al. |
| 8,409,273 B2 | 4/2013 | Thornton et al. |
| 8,419,753 B2 | 4/2013 | Stafford |
| 8,430,893 B2 | 4/2013 | Ma |
| 8,449,606 B2 | 5/2013 | Eliasen et al. |
| 8,460,368 B2 | 6/2013 | Taylor et al. |
| 8,460,371 B2 | 6/2013 | Hlavka et al. |
| 8,475,525 B2 | 7/2013 | Maisano et al. |
| 8,480,691 B2 | 7/2013 | Dana et al. |
| 8,480,730 B2 | 7/2013 | Maurer et al. |
| 8,523,881 B2 | 9/2013 | Cabiri et al. |
| 8,524,132 B2 | 9/2013 | Von Oepen et al. |
| 8,529,621 B2 | 9/2013 | Alfieri et al. |
| 8,545,553 B2 | 10/2013 | Zipory et al. |
| 8,568,475 B2 | 10/2013 | Nguyen et al. |
| 8,568,476 B2 | 10/2013 | Rao et al. |
| 8,591,460 B2 | 11/2013 | Wilson et al. |
| 8,597,347 B2 | 12/2013 | Maurer et al. |
| 8,628,569 B2 | 1/2014 | Benichou et al. |
| 8,628,571 B1 | 1/2014 | Hacohen |
| 8,663,248 B2 | 3/2014 | Zung et al. |
| 8,685,080 B2 | 4/2014 | White |
| 8,685,083 B2 | 4/2014 | Perier et al. |
| 8,721,588 B2 | 5/2014 | Echarri et al. |
| 8,728,097 B1 | 5/2014 | Sugimoto et al. |
| 8,747,463 B2 | 6/2014 | Fogarty et al. |
| 8,753,357 B2 | 6/2014 | Roorda et al. |
| 8,753,373 B2 | 6/2014 | Chau et al. |
| 8,778,017 B2 | 7/2014 | Eliasen et al. |
| 8,784,481 B2 | 7/2014 | Alkhatib et al. |
| 8,790,394 B2 | 7/2014 | Miller et al. |
| 8,795,356 B2 | 8/2014 | Quadri et al. |
| 8,808,366 B2 | 8/2014 | Braido et al. |
| 8,808,368 B2 | 8/2014 | Maisano et al. |
| 8,845,723 B2 | 9/2014 | Spence et al. |
| 8,852,270 B2 | 10/2014 | Maurer et al. |
| 8,852,272 B2 | 10/2014 | Gross et al. |
| 8,858,594 B2 | 10/2014 | Clark |
| 8,858,623 B2 | 10/2014 | Miller et al. |
| 8,864,822 B2 | 10/2014 | Spence et al. |
| 8,870,949 B2 | 10/2014 | Rowe |
| 8,870,950 B2 | 10/2014 | Hacohen |
| 8,893,947 B2 | 11/2014 | Reynolds et al. |
| 8,911,461 B2 | 12/2014 | Traynor et al. |
| 8,926,691 B2 | 1/2015 | Chau et al. |
| 8,945,177 B2 | 2/2015 | Dell et al. |
| 8,945,211 B2 | 2/2015 | Sugimoto |
| 8,951,285 B2 | 2/2015 | Sugimoto et al. |
| 8,961,594 B2 | 2/2015 | Maisano et al. |
| 8,961,595 B2 | 2/2015 | Alkhatib |
| 8,961,596 B2 | 2/2015 | Maisano et al. |
| 8,968,335 B2 | 3/2015 | Robinson et al. |
| 8,968,336 B2 | 3/2015 | Conklin et al. |
| 8,968,395 B2 | 3/2015 | Hauser et al. |
| 8,979,922 B2 | 3/2015 | Jayasinghe et al. |
| 8,979,923 B2 | 3/2015 | Spence et al. |
| 9,005,273 B2 | 4/2015 | Salahieh et al. |
| 9,011,468 B2 | 4/2015 | Ketai et al. |
| 9,017,347 B2 | 4/2015 | Oba et al. |
| 9,034,032 B2 | 5/2015 | McLean et al. |
| 9,034,033 B2 | 5/2015 | McLean et al. |
| 9,078,652 B2 | 7/2015 | Conklin et al. |
| 9,084,676 B2 | 7/2015 | Chau et al. |
| 9,107,749 B2 | 8/2015 | Bobo et al. |
| 9,131,939 B1 | 9/2015 | Call et al. |
| 9,138,335 B2 | 9/2015 | Cartledge et al. |
| 9,180,005 B1 | 11/2015 | Lashinski et al. |
| 9,192,471 B2 | 11/2015 | Bolling |
| 9,211,203 B2 | 12/2015 | Pike et al. |
| 9,241,702 B2 | 1/2016 | Maisano et al. |
| 9,241,706 B2 | 1/2016 | Paraschac et al. |
| 9,259,218 B2 | 2/2016 | Robinson |
| 9,259,317 B2 | 2/2016 | Wilson et al. |
| 9,282,965 B2 | 3/2016 | Kokish |
| 9,289,282 B2 | 3/2016 | Olson et al. |
| 9,289,297 B2 | 3/2016 | Wilson et al. |
| 9,301,749 B2 | 4/2016 | Rowe et al. |
| 9,314,242 B2 | 4/2016 | Bachman |
| 9,326,870 B2 | 5/2016 | Berglund et al. |
| 9,358,111 B2 | 6/2016 | Spence et al. |
| 9,408,607 B2 | 8/2016 | Cartledge et al. |
| 9,474,605 B2 | 10/2016 | Rowe et al. |
| 2002/0013571 A1 | 1/2002 | Goldfarb et al. |
| 2002/0032481 A1 | 3/2002 | Gabbay |

(56) References Cited

U.S. PATENT DOCUMENTS

| | | |
|---|---|---|
| 2002/0082625 A1 | 6/2002 | Huxel et al. |
| 2002/0107564 A1 | 8/2002 | Cox et al. |
| 2002/0151961 A1 | 10/2002 | Lashinski et al. |
| 2002/0156517 A1 | 10/2002 | Perouse |
| 2002/0177904 A1 | 11/2002 | Huxel et al. |
| 2003/0033003 A1 | 2/2003 | Harrison et al. |
| 2003/0057156 A1 | 3/2003 | Peterson et al. |
| 2003/0083742 A1 | 5/2003 | Spence et al. |
| 2003/0093096 A1 | 5/2003 | McGuckin, Jr. et al. |
| 2003/0167071 A1 | 9/2003 | Martin et al. |
| 2003/0229350 A1 | 12/2003 | Kay |
| 2003/0236568 A1 | 12/2003 | Hojeibane et al. |
| 2004/0117009 A1 | 6/2004 | Cali et al. |
| 2004/0133274 A1 | 7/2004 | Webler et al. |
| 2004/0172046 A1 | 9/2004 | Hlavka et al. |
| 2004/0181287 A1 | 9/2004 | Gellman |
| 2004/0186566 A1 | 9/2004 | Hindrichs et al. |
| 2004/0193092 A1 | 9/2004 | Deal |
| 2004/0236419 A1 | 11/2004 | Milo |
| 2004/0260389 A1 | 12/2004 | Case et al. |
| 2005/0004668 A1 | 1/2005 | Aklog et al. |
| 2005/0016560 A1 | 1/2005 | Voughlohn |
| 2005/0021085 A1 | 1/2005 | Abrams et al. |
| 2005/0055089 A1 | 3/2005 | Macoviak et al. |
| 2005/0059997 A1 | 3/2005 | Bauman et al. |
| 2005/0075723 A1 | 4/2005 | Schroeder et al. |
| 2005/0080483 A1 | 4/2005 | Solem et al. |
| 2005/0090827 A1 | 4/2005 | Gedebou |
| 2005/0096666 A1 | 5/2005 | Gordon et al. |
| 2005/0107812 A1 | 5/2005 | Starksen et al. |
| 2005/0107871 A1 | 5/2005 | Realyvasquez et al. |
| 2005/0113900 A1 | 5/2005 | Shiroff et al. |
| 2005/0125077 A1 | 6/2005 | Harmon et al. |
| 2005/0137688 A1 | 6/2005 | Salahieh et al. |
| 2005/0137695 A1 | 6/2005 | Salahieh et al. |
| 2005/0143770 A1* | 6/2005 | Carter .................. A61B 1/018 606/170 |
| 2005/0154448 A1 | 7/2005 | Cully et al. |
| 2005/0177180 A1 | 8/2005 | Kaganov et al. |
| 2005/0177228 A1 | 8/2005 | Solem |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0251208 A1 | 11/2005 | Elmer et al. |
| 2005/0256532 A1 | 11/2005 | Nayak et al. |
| 2005/0273138 A1 | 12/2005 | To et al. |
| 2005/0283246 A1 | 12/2005 | Cauthen et al. |
| 2006/0004442 A1 | 1/2006 | Spenser et al. |
| 2006/0020326 A9 | 1/2006 | Bolduc et al. |
| 2006/0020327 A1 | 1/2006 | Lashinski et al. |
| 2006/0052821 A1 | 3/2006 | Abbott et al. |
| 2006/0106420 A1 | 5/2006 | Dolan et al. |
| 2006/0106423 A1 | 5/2006 | Weisel et al. |
| 2006/0129166 A1 | 6/2006 | Lavelle |
| 2006/0161265 A1 | 7/2006 | Levine et al. |
| 2006/0173524 A1 | 8/2006 | Salahieh et al. |
| 2006/0178700 A1 | 8/2006 | Quinn |
| 2006/0200199 A1 | 9/2006 | Bonutti et al. |
| 2006/0206201 A1 | 9/2006 | Garcia et al. |
| 2006/0229708 A1 | 10/2006 | Powell et al. |
| 2006/0241745 A1 | 10/2006 | Solem |
| 2006/0241748 A1 | 10/2006 | Lee et al. |
| 2006/0259135 A1 | 11/2006 | Navia et al. |
| 2006/0259137 A1 | 11/2006 | Artof et al. |
| 2006/0276871 A1 | 12/2006 | Lamson et al. |
| 2006/0282161 A1 | 12/2006 | Huynh et al. |
| 2007/0016287 A1 | 1/2007 | Cartledge |
| 2007/0016288 A1 | 1/2007 | Gurskis |
| 2007/0021781 A1 | 1/2007 | Jervis et al. |
| 2007/0032787 A1 | 2/2007 | Hassett et al. |
| 2007/0038221 A1 | 2/2007 | Fine et al. |
| 2007/0038296 A1 | 2/2007 | Navia |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055340 A1 | 3/2007 | Pryor |
| 2007/0060895 A1 | 3/2007 | Sibbitt et al. |
| 2007/0060989 A1 | 3/2007 | Deem et al. |
| 2007/0061010 A1 | 3/2007 | Hauser et al. |
| 2007/0066863 A1 | 3/2007 | Rafiee et al. |
| 2007/0083168 A1 | 4/2007 | Whiting et al. |
| 2007/0093869 A1 | 4/2007 | Bloom et al. |
| 2007/0100427 A1 | 5/2007 | Perouse |
| 2007/0112425 A1 | 5/2007 | Schaller et al. |
| 2007/0118151 A1 | 5/2007 | Davidson |
| 2007/0123936 A1 | 5/2007 | Goldin et al. |
| 2007/0162107 A1 | 7/2007 | Haug et al. |
| 2007/0168013 A1 | 7/2007 | Douglas |
| 2007/0185532 A1 | 8/2007 | Stone et al. |
| 2007/0198082 A1 | 8/2007 | Kapadia et al. |
| 2007/0203391 A1 | 8/2007 | Bloom et al. |
| 2007/0208389 A1 | 9/2007 | Amundson et al. |
| 2007/0219558 A1 | 9/2007 | Deutsch |
| 2007/0250160 A1 | 10/2007 | Rafiee |
| 2007/0265700 A1 | 11/2007 | Eliasen et al. |
| 2007/0270943 A1 | 11/2007 | Solem et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0288089 A1 | 12/2007 | Gurskis et al. |
| 2008/0003539 A1 | 1/2008 | Lundgren |
| 2008/0015617 A1 | 1/2008 | Harari et al. |
| 2008/0027268 A1 | 1/2008 | Buckner et al. |
| 2008/0027446 A1 | 1/2008 | Stone et al. |
| 2008/0027483 A1 | 1/2008 | Cartledge |
| 2008/0035160 A1 | 2/2008 | Woodson et al. |
| 2008/0039845 A1* | 2/2008 | Bonutti ............. A61B 17/0401 606/62 |
| 2008/0058866 A1 | 3/2008 | Young et al. |
| 2008/0077231 A1 | 3/2008 | Heringes et al. |
| 2008/0097595 A1 | 4/2008 | Gabbay |
| 2008/0125861 A1 | 5/2008 | Webler et al. |
| 2008/0140116 A1 | 6/2008 | Bonutti |
| 2008/0140188 A1 | 6/2008 | Rahdert et al. |
| 2008/0167714 A1 | 7/2008 | St. Goar |
| 2008/0190989 A1 | 8/2008 | Crews et al. |
| 2008/0262598 A1 | 10/2008 | Elmaleh |
| 2008/0262609 A1 | 10/2008 | Gross et al. |
| 2008/0275469 A1 | 11/2008 | Fanton et al. |
| 2008/0281411 A1 | 11/2008 | Berreklouw et al. |
| 2008/0288044 A1 | 11/2008 | Osborne |
| 2008/0288062 A1 | 11/2008 | Andrieu et al. |
| 2008/0300629 A1 | 12/2008 | Surti |
| 2009/0005863 A1 | 1/2009 | Goetz et al. |
| 2009/0043382 A1 | 2/2009 | Maurer et al. |
| 2009/0048668 A1 | 2/2009 | Wilson et al. |
| 2009/0082828 A1 | 3/2009 | Ostroff |
| 2009/0082847 A1 | 3/2009 | Zacharias et al. |
| 2009/0084386 A1 | 4/2009 | McClellan et al. |
| 2009/0099647 A1 | 4/2009 | Glimsdale et al. |
| 2009/0099649 A1 | 4/2009 | Chobotov et al. |
| 2009/0112052 A1 | 4/2009 | Lund et al. |
| 2009/0118776 A1 | 5/2009 | Kelsch et al. |
| 2009/0131849 A1 | 5/2009 | Maurer et al. |
| 2009/0132033 A1 | 5/2009 | Maurer et al. |
| 2009/0143808 A1 | 6/2009 | Houser |
| 2009/0149872 A1 | 6/2009 | Gross et al. |
| 2009/0171439 A1 | 7/2009 | Nissl |
| 2009/0216265 A1 | 8/2009 | DeVries |
| 2009/0240326 A1 | 9/2009 | Wilson et al. |
| 2009/0254103 A1 | 10/2009 | Deutsch et al. |
| 2009/0259307 A1 | 10/2009 | Gross et al. |
| 2009/0264991 A1 | 10/2009 | Paul et al. |
| 2009/0264995 A1 | 10/2009 | Subramanian |
| 2009/0276040 A1 | 11/2009 | Rowe et al. |
| 2009/0287304 A1 | 11/2009 | Dahlgren et al. |
| 2009/0306622 A1 | 12/2009 | Machold et al. |
| 2009/0326648 A1 | 12/2009 | Machold et al. |
| 2010/0022948 A1 | 1/2010 | Wilson et al. |
| 2010/0023117 A1 | 1/2010 | Yoganathan et al. |
| 2010/0023118 A1 | 1/2010 | Medlock et al. |
| 2010/0029071 A1 | 2/2010 | Russell et al. |
| 2010/0030329 A1 | 2/2010 | Frater |

(56) References Cited

U.S. PATENT DOCUMENTS

| | | |
|---|---|---|
| 2010/0049293 A1 | 2/2010 | Zukowski et al. |
| 2010/0063520 A1 | 3/2010 | Bilotti |
| 2010/0063542 A1 | 3/2010 | Van der Burg et al. |
| 2010/0063586 A1 | 3/2010 | Hasenkam et al. |
| 2010/0121349 A1 | 5/2010 | Meier et al. |
| 2010/0121434 A1 | 5/2010 | Paul et al. |
| 2010/0121435 A1 | 5/2010 | Subramanian et al. |
| 2010/0130992 A1 | 5/2010 | Machold et al. |
| 2010/0161041 A1 | 6/2010 | Maisano et al. |
| 2010/0161042 A1 | 6/2010 | Maisano et al. |
| 2010/0161043 A1 | 6/2010 | Maisano et al. |
| 2010/0161047 A1 | 6/2010 | Cabiri |
| 2010/0168791 A1 | 7/2010 | Kassab |
| 2010/0174358 A1 | 7/2010 | Rabkin |
| 2010/0185278 A1 | 7/2010 | Schankereli |
| 2010/0204662 A1 | 8/2010 | Orlov et al. |
| 2010/0211166 A1 | 8/2010 | Miller et al. |
| 2010/0217382 A1 | 8/2010 | Chau et al. |
| 2010/0228269 A1 | 9/2010 | Garrison et al. |
| 2010/0234935 A1 | 9/2010 | Bashiri |
| 2010/0249908 A1 | 9/2010 | Chau et al. |
| 2010/0249920 A1 | 9/2010 | Bolling et al. |
| 2010/0264192 A1 | 10/2010 | Marczyk |
| 2010/0268204 A1 | 10/2010 | Tieu et al. |
| 2010/0280603 A1 | 11/2010 | Maisano et al. |
| 2010/0280604 A1 | 11/2010 | Zipory et al. |
| 2010/0280605 A1 | 11/2010 | Hammer et al. |
| 2010/0286628 A1 | 11/2010 | Gross |
| 2010/0286767 A1 | 11/2010 | Zipory et al. |
| 2010/0298930 A1 | 11/2010 | Orlov |
| 2010/0324598 A1 | 12/2010 | Anderson |
| 2010/0324668 A1 | 12/2010 | Maurer et al. |
| 2011/0004296 A1 | 1/2011 | Lutter et al. |
| 2011/0009818 A1 | 1/2011 | Goff |
| 2011/0011917 A1 | 1/2011 | Loulmet |
| 2011/0022164 A1 | 1/2011 | Quinn et al. |
| 2011/0029066 A1 | 2/2011 | Gilad |
| 2011/0029071 A1 | 2/2011 | Zlotnick et al. |
| 2011/0035000 A1 | 2/2011 | Nieminen et al. |
| 2011/0040366 A1 | 2/2011 | Goetz et al. |
| 2011/0071626 A1 | 3/2011 | Wright et al. |
| 2011/0077733 A1 | 3/2011 | Solem |
| 2011/0082538 A1 | 4/2011 | Dahlgren et al. |
| 2011/0087146 A1 | 4/2011 | Ryan et al. |
| 2011/0092993 A1 | 4/2011 | Jacobs |
| 2011/0093002 A1 | 4/2011 | Rucker et al. |
| 2011/0098732 A1 | 4/2011 | Jacobs |
| 2011/0106245 A1 | 5/2011 | Miller et al. |
| 2011/0106247 A1 | 5/2011 | Miller et al. |
| 2011/0112619 A1 | 5/2011 | Foster et al. |
| 2011/0112632 A1 | 5/2011 | Chau et al. |
| 2011/0137397 A1 | 6/2011 | Chau et al. |
| 2011/0152998 A1 | 6/2011 | Berez et al. |
| 2011/0166636 A1 | 7/2011 | Rowe |
| 2011/0184510 A1 | 7/2011 | Maisano |
| 2011/0190879 A1 | 8/2011 | Bobo et al. |
| 2011/0208283 A1 | 8/2011 | Rust et al. |
| 2011/0224785 A1 | 9/2011 | Hacohen |
| 2011/0238088 A1 | 9/2011 | Bolduc et al. |
| 2011/0238112 A1 | 9/2011 | Kim et al. |
| 2011/0251678 A1 | 10/2011 | Eidenschink |
| 2011/0264208 A1 | 10/2011 | Duffy et al. |
| 2011/0301698 A1 | 12/2011 | Miller et al. |
| 2012/0016343 A1 | 1/2012 | Gill |
| 2012/0022633 A1 | 1/2012 | Olson et al. |
| 2012/0022639 A1 | 1/2012 | Hacohen et al. |
| 2012/0022640 A1 | 1/2012 | Gross et al. |
| 2012/0035712 A1 | 2/2012 | Maisano |
| 2012/0083806 A1 | 4/2012 | Goertzen |
| 2012/0123531 A1 | 5/2012 | Tsukashima et al. |
| 2012/0130374 A1 | 5/2012 | Bouduban et al. |
| 2012/0130421 A1 | 5/2012 | Hafez et al. |
| 2012/0143320 A1 | 6/2012 | Eliasen et al. |
| 2012/0158053 A1 | 6/2012 | Paulos |
| 2012/0179244 A1 | 7/2012 | Schankereli et al. |
| 2012/0215236 A1 | 8/2012 | Matsunaga et al. |
| 2012/0222969 A1 | 9/2012 | Osborne et al. |
| 2012/0226349 A1 | 9/2012 | Tuval et al. |
| 2012/0232373 A1 | 9/2012 | Hallander et al. |
| 2012/0245604 A1 | 9/2012 | Tegzes |
| 2012/0283757 A1 | 11/2012 | Miller et al. |
| 2012/0296349 A1 | 11/2012 | Smith et al. |
| 2012/0310328 A1 | 12/2012 | Olson et al. |
| 2013/0018459 A1 | 1/2013 | Maisano et al. |
| 2013/0030522 A1 | 1/2013 | Rowe et al. |
| 2013/0041459 A1 | 2/2013 | Wilson et al. |
| 2013/0053951 A1 | 2/2013 | Baliarda |
| 2013/0085529 A1 | 4/2013 | Housman |
| 2013/0096664 A1 | 4/2013 | Goetz et al. |
| 2013/0096672 A1 | 4/2013 | Reich et al. |
| 2013/0110230 A1 | 5/2013 | Solem |
| 2013/0166017 A1 | 6/2013 | Cartledge et al. |
| 2013/0166022 A1 | 6/2013 | Conklin |
| 2013/0172978 A1 | 7/2013 | Vidlund et al. |
| 2013/0281760 A1 | 10/2013 | Farnan et al. |
| 2013/0296925 A1 | 11/2013 | Chanduszko et al. |
| 2013/0325110 A1 | 12/2013 | Khalil et al. |
| 2013/0331930 A1 | 12/2013 | Rowe et al. |
| 2014/0005778 A1 | 1/2014 | Buchbinder et al. |
| 2014/0018911 A1 | 1/2014 | Zhou et al. |
| 2014/0031864 A1 | 1/2014 | Jafari et al. |
| 2014/0031928 A1 | 1/2014 | Murphy et al. |
| 2014/0058405 A1 | 2/2014 | Foster |
| 2014/0066693 A1 | 3/2014 | Goldfarb et al. |
| 2014/0067054 A1 | 3/2014 | Chau et al. |
| 2014/0114390 A1 | 4/2014 | Tobis et al. |
| 2014/0121763 A1 | 5/2014 | Duffy et al. |
| 2014/0142689 A1 | 5/2014 | De Canniere et al. |
| 2014/0163690 A1 | 6/2014 | White |
| 2014/0200657 A1 | 7/2014 | Maurer et al. |
| 2014/0207231 A1 | 7/2014 | Hacohen et al. |
| 2014/0214159 A1 | 7/2014 | Vidlund et al. |
| 2014/0243894 A1 | 8/2014 | Groothuis et al. |
| 2014/0257475 A1 | 9/2014 | Gross et al. |
| 2014/0275757 A1 | 9/2014 | Goodwin et al. |
| 2014/0277390 A1 | 9/2014 | Ratz et al. |
| 2014/0277427 A1 | 9/2014 | Ratz et al. |
| 2014/0288639 A1 | 9/2014 | Gainor |
| 2014/0296962 A1 | 10/2014 | Cartledge et al. |
| 2014/0309730 A1 | 10/2014 | Alon et al. |
| 2014/0324164 A1 | 10/2014 | Gross et al. |
| 2014/0358224 A1 | 12/2014 | Tegels et al. |
| 2014/0371843 A1 | 12/2014 | Wilson et al. |
| 2014/0379006 A1 | 12/2014 | Sutherland et al. |
| 2014/0379074 A1 | 12/2014 | Spence et al. |
| 2014/0379076 A1 | 12/2014 | Vidlund et al. |
| 2015/0018940 A1 | 1/2015 | Quill et al. |
| 2015/0045879 A1 | 2/2015 | Longoria et al. |
| 2015/0051698 A1 | 2/2015 | Baliarda et al. |
| 2015/0066138 A1 | 3/2015 | Alexander et al. |
| 2015/0073545 A1 | 3/2015 | Braido |
| 2015/0094800 A1 | 4/2015 | Chawla |
| 2015/0094802 A1 | 4/2015 | Buchbinder et al. |
| 2015/0100116 A1 | 4/2015 | Mohl et al. |
| 2015/0119936 A1 | 4/2015 | Gilmore et al. |
| 2015/0127097 A1 | 5/2015 | Neumann et al. |
| 2015/0142049 A1 | 5/2015 | Delgado et al. |
| 2015/0142103 A1 | 5/2015 | Vidlund |
| 2015/0142105 A1 | 5/2015 | Bolling et al. |
| 2015/0182336 A1 | 7/2015 | Zipory et al. |
| 2015/0196693 A1 | 7/2015 | Lin |
| 2015/0223934 A1 | 8/2015 | Vidlund et al. |
| 2015/0250590 A1 | 9/2015 | Gries et al. |
| 2015/0272730 A1 | 10/2015 | Melnick et al. |
| 2015/0320414 A1 | 11/2015 | Conklin et al. |
| 2015/0351909 A1 | 12/2015 | Bobo et al. |
| 2015/0351910 A1 | 12/2015 | Gilmore et al. |
| 2016/0022417 A1 | 1/2016 | Karapetian et al. |
| 2016/0038285 A1 | 2/2016 | Glenn et al. |
| 2016/0081829 A1 | 3/2016 | Rowe |
| 2016/0120672 A1 | 5/2016 | Martin et al. |
| 2016/0128689 A1 | 5/2016 | Sutherland et al. |
| 2016/0157862 A1 | 6/2016 | Hernandez et al. |
| 2016/0174979 A1 | 6/2016 | Wei |

(56) References Cited

U.S. PATENT DOCUMENTS

| | | |
|---|---|---|
| 2016/0228246 A1 | 8/2016 | Zimmerman |
| 2016/0228252 A1 | 8/2016 | Keidar |
| 2016/0235526 A1 | 8/2016 | Lashinski et al. |
| 2016/0242762 A1 | 8/2016 | Gilmore et al. |
| 2016/0256269 A1 | 9/2016 | Cahalane et al. |
| 2016/0262741 A1 | 9/2016 | Gilmore et al. |
| 2016/0270776 A1 | 9/2016 | Miraki et al. |
| 2016/0270916 A1 | 9/2016 | Cahalane et al. |
| 2016/0287383 A1 | 10/2016 | Rowe |
| 2016/0287387 A1 | 10/2016 | Wei |

FOREIGN PATENT DOCUMENTS

| | | |
|---|---|---|
| EP | 1397176 | 3/2007 |
| EP | 1759663 | 3/2007 |
| EP | 1 836 971 | 9/2007 |
| EP | 1562522 | 12/2008 |
| EP | 1357843 | 5/2009 |
| EP | 1 968 491 | 7/2010 |
| EP | 1928357 | 11/2010 |
| EP | 1718249 | 4/2011 |
| EP | 2399549 | 3/2014 |
| EP | 1646332 | 6/2015 |
| EP | 2410948 | 7/2016 |
| EP | 2465568 | 8/2016 |
| EP | 2023858 | 10/2016 |
| WO | 92/05093 | 4/1992 |
| WO | 97/41778 | 11/1997 |
| WO | 00/28923 | 5/2000 |
| WO | 01/10306 | 2/2001 |
| WO | 2004/069055 | 8/2004 |
| WO | 2004/082538 | 9/2004 |
| WO | 2005/021063 | 3/2005 |
| WO | 2005/058206 | 6/2005 |
| WO | 2005/102194 | 11/2005 |
| WO | 2006/019498 | 2/2006 |
| WO | 2006/097931 | 9/2006 |
| WO | 2006/105008 | 10/2006 |
| WO | 2006/105009 | 10/2006 |
| WO | 2007/080595 | 7/2007 |
| WO | 2007/140309 | 12/2007 |
| WO | 2008/065044 | 6/2008 |
| WO | 2008/068756 | 6/2008 |
| WO | 2009/039400 | 3/2009 |
| WO | 2009/101617 | 8/2009 |
| WO | 2010/004546 | 1/2010 |
| WO | 2010/008549 | 1/2010 |
| WO | 2010/071494 | 6/2010 |
| WO | 2010/073246 | 7/2010 |
| WO | 2010/099032 | 9/2010 |
| WO | 2010/108079 | 9/2010 |
| WO | 2010/128502 | 11/2010 |
| WO | 2010/128503 | 11/2010 |
| WO | 2011/014496 | 2/2011 |
| WO | 2011/037891 | 3/2011 |
| WO | 2011/051942 | 5/2011 |
| WO | 2011/089601 | 7/2011 |
| WO | 2011/097355 | 8/2011 |
| WO | 2011/143263 | 11/2011 |
| WO | 2011/153408 | 12/2011 |
| WO | 2012/127309 | 9/2012 |
| WO | 2013/003228 | 1/2013 |
| WO | 2013/011502 | 1/2013 |
| WO | 2013/028145 | 2/2013 |
| WO | 2013/078497 | 6/2013 |
| WO | 2014/043527 | 3/2014 |
| WO | 2014/064694 | 5/2014 |
| WO | 2014/087402 | 6/2014 |
| WO | 2014/108903 | 7/2014 |
| WO | 2014/141239 | 9/2014 |
| WO | 2015/015497 | 2/2015 |
| WO | 2015/063580 | 5/2015 |
| WO | 2015/193728 | 12/2015 |
| WO | 2016/011275 | 1/2016 |
| WO | 2016/087934 | 6/2016 |

OTHER PUBLICATIONS

U.S. Appl. No. 62/131,636, filed Mar. 11, 2015.

Alfieri et al., "An effective technique to correct anterior mitral leaflet prolapse," J Card Surg 14(6):468-470 (1999).

U.S. Appl. No. 62/014,397, filed Jun. 19, 2014.

Alfieri et al., "Novel suture device for beating heart mitral leaflet approximation," Annals of Thoracic Surgery 74:1488 1493 (2002).

Alfieri et al., "The double orifice technique in mitral valve repair: a simple solution for complex problems," Journal of Thoracic Cardiovascular Surgery 122:674-681 (2001).

Amplatzer Cardiac Plug Brochure (English Pages), AGA Medical Corporation, Plymouth, MN Copyright 2008-2011, downloaded Jan. 11, 2011.

Beale BS, "Surgical Repair of Collateral Ligament Injuries," presented at 63rd CVMA Convention, Halifax, Nova Scotia, Canada, Jul. 6-9, 2011.

Dentistry Today, "Implant Direct" product information page, Jun. 1, 2011, downloaded Dec. 10, 2012 from http://dentistrytoday.com/top25implant-i/5558-implant-direct.

Maisano et al., "The double-orifice technique as a standardized approach to treat mitral regurgitation due to severe myxomatous disease: surgical technique," European Journal of Cardio-thoracic Surgery 17 (2000) 201-205.

Shikhar Agarwal et al., "Interventional Cardiology Perspective of Functional Tricuspid Regurgitation," Circulatoin: Cardiovascular Interventions, pp. 565-573; Dec. 2009; vol. 2, Issue 6.

Smith & Nephew MINITAC™ TI 2.0 Suture Anchor Product Description, downloaded on Dec. 9, 2012 from http://global.smith-nephew.com/us/MINITAC_TI_2_SUTURE_ANCHR_3127.htm.

Second Notice of Allowance dated May 10, 2013, which issued during the prosecution of U.S. Appl. No. 12/692,061.

An Interview Summary dated Nov. 5, 2012, which issued during the prosecution of U.S. Appl. No. 12/692,061.

An Office Action dated Jul. 6, 2012, which issued during the prosecution of U.S. Appl. No. 12/692,061.

A Notice of Allowance dated Mar. 6, 2013, which issued during the prosecution of U.S. Appl. No. 12/692,061.

An International Search Report and a Written Opinion both dated May 19, 2011, which issued during the prosecution of Applicant's PCT/IL11/00064.

An International Search Report and a Written Opinion both dated Jan. 22, 2013, which issued during the prosecution of Applicant's PCT/IL2012/000282.

An Office Action dated Dec. 5, 2013, which issued during the prosecution of U.S. Appl. No. 13/485,145.

An International Search Report and a Written Opinion both dated Mar. 17, 2014, which issued during the prosecution of Applicant's PCT/IL2013/050937.

Invitation to pay additional fees in PCT/IL2014/050027 dated Apr. 4, 2014.

An International Search Report and a Written Opinion both dated May 28, 2014, which issued during the prosecution of Applicant's PCT/IL2014/050027.

U.S. Appl. No. 60/902,146, filed Feb. 16, 2007.

European Search Report dated Apr. 10, 2015, which issued during the prosecution of Applicant's European App No. 11734451.5.

European Search Report dated May 15, 2015, which issued during the prosecution of Applicant's European App No. 12814417.7.

An Office Action dated Sep. 14, 2015, which issued during the prosecution of U.S. Appl. No. 13/553,081.

An English Translation of an Office Action dated Jun. 30, 2015 which issued during the prosecution of Chinese Patent Application No. 201180015301.6.

An English Translation of an Office Action dated Jul. 7, 2015 which issued during the prosecution of Japanese Patent Application No. 2012-549463.

An Office Action dated Oct. 7, 2015, which issued during the prosecution of U.S. Appl. No. 13/574,088.

Invitation to Pay Additional Fees dated Apr. 20, 2015, which issued during the prosecution of Applicant's PCT/IB2014/002351.

(56) References Cited

OTHER PUBLICATIONS

An International Search Report and a Written Opinion both dated Jun. 10, 2015, which issued during the prosecution of Applicant's PCT/IB2014/002351.
An Office Action dated Feb. 2, 2015, which issued during the prosecution of U.S. Appl. No. 14/143,355.
An English Translation of an Office Action dated Feb. 10, 2015 which issued during the prosecution of Chinese Patent Application No. 201180015301.6.
An Office Action dated Feb. 25, 2015, which issued during the prosecution of U.S. Appl. No. 13/574,088.
Notice of Allowance dated Sep. 24, 2015, which issued during the prosecution of U.S. Appl. No. 14/143,355.
Notice of Allowance dated Dec. 4, 2015, which issued during the prosecution of U.S. Appl. No. 14/143,355.
An Office Action dated Jul. 7, 2014, which issued during the prosecution of U.S. Appl. No. 13/485,145.
An English Translation of an Office Action dated Jun. 30, 2014 which issued during the prosecution of Chinese Patent Application No. 201180015301.6.
An Office Action dated Sep. 25, 2014, which issued during the prosecution of U.S. Appl. No. 13/485,145.
An English Translation of an Office Action dated Oct. 28, 2014,which issued during the prosecution of Japanese Patent Application No. 2012-549463.
Notice of Allowance dated Dec. 9, 2014, which issued during the prosecution of U.S. Appl. No. 13/485,145.
An International Search Report and a Written Opinion both dated Jun. 30, 2014, which issued during the prosecution of Applicant's PCT/IL2014/050233.
An International Search Report and a Written Opinion both dated Jan. 8 2016, 2014, which issued during the prosecution of Applicant's PCT/IB2015/001196.
Invitation to pay additional fees in PCT/IB2015/001196 dated Oct. 26, 2015.
Notice of Allowance dated Dec. 4, 2014, which issued during the prosecution of U.S. Appl. No. 13/188,175.
An Office Action dated Nov. 25, 2014, which issued during the prosecution of U.S. Appl. No. 13/553,081.
An Office Action dated Apr. 18, 2016, which issued during the prosecution of U.S. Appl. No. 14/584,286.
Spinal & Epidural Needles—downloaded on Feb. 18, 2016 from http://www.cothon.net/Anestesia_Obstetrica/Neuroaxial_needles.html.
An Office Action dated May 11, 2016, which issued during the prosecution of U.S. Appl. No. 13/574,088.
An International Search Report and a Written Opinion both dated Apr. 15, 2016, 2014, which issued during the prosecution of Applicant's PCT/IB2015/002354.
U.S. Appl. No. 62/167,660, filed May 28, 2015.
An English Translation of an Office Action dated Jun. 23, 2016 which issued during the prosecution of Chinese Patent Application No. 201480028044.3. (the relevant part only).
U.S. Appl. No. 62/086,269, filed Dec. 2, 2014.
Notice of Allowance dated Sep. 5, 2016, which issued during the prosecution of Chinese Patent Application No. 2014800280443.
An Office Action dated Sep. 14, 2016, which issued during the prosecution of U.S. Appl. No. 13/574,088.
Invitation to pay additional fees in PCT/IB2016/000840 dated Oct. 13, 2016.
U.S. Appl. No. 61/750,427, filed Jan. 9, 2013.
An International Search Report and Written Opinion in PCT/1B2016/000840, dated Dec. 8, 2016.

\* cited by examiner

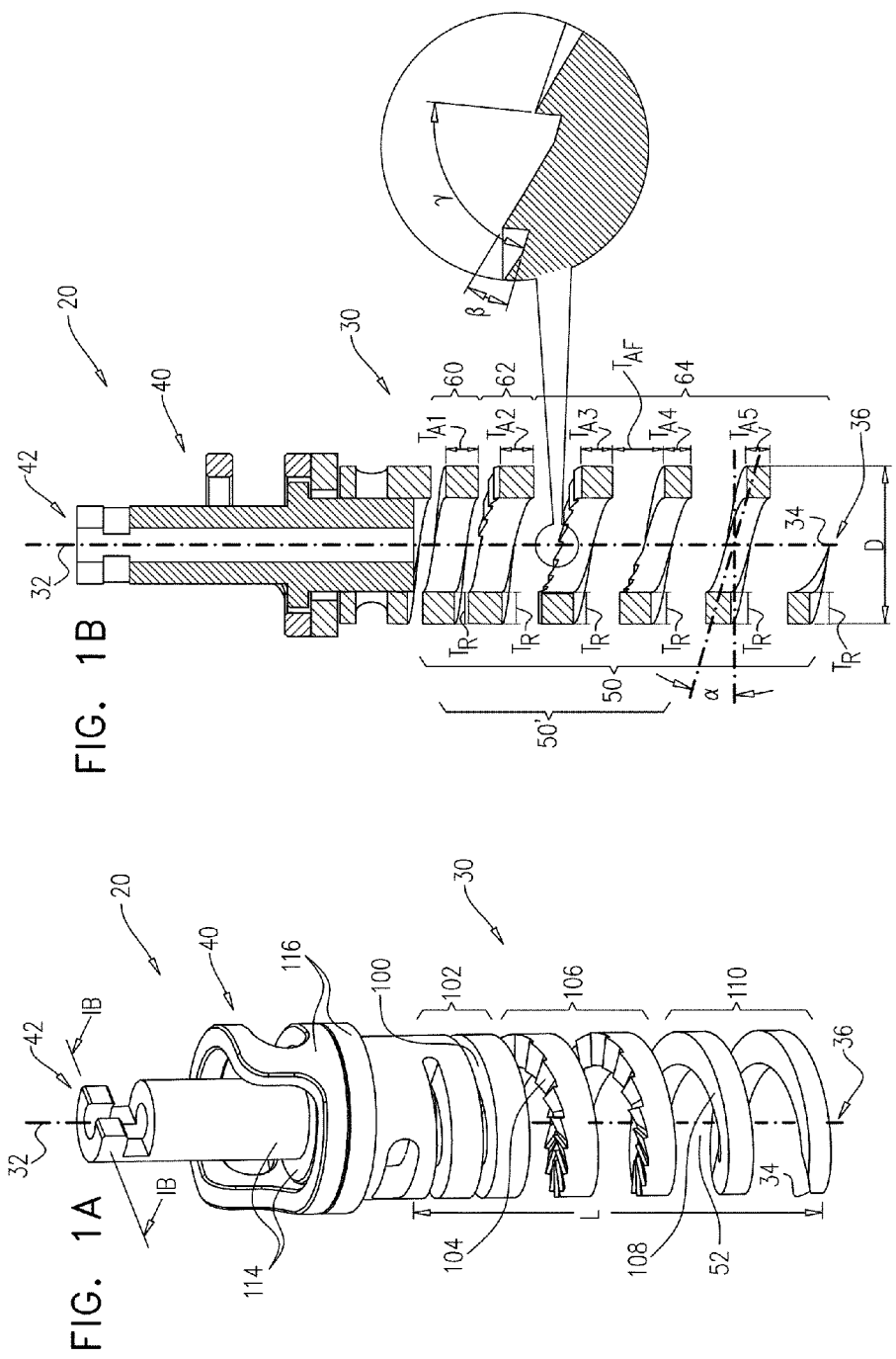

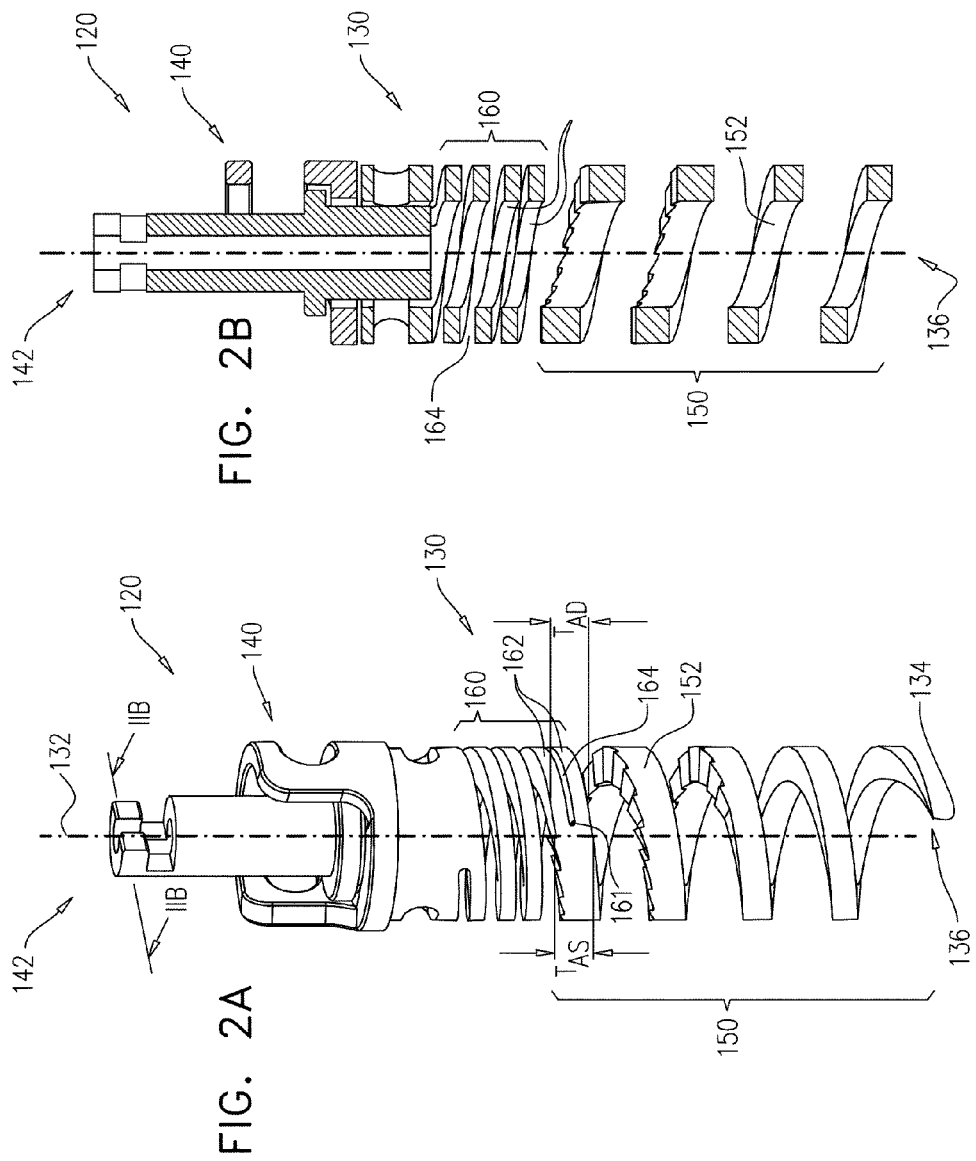

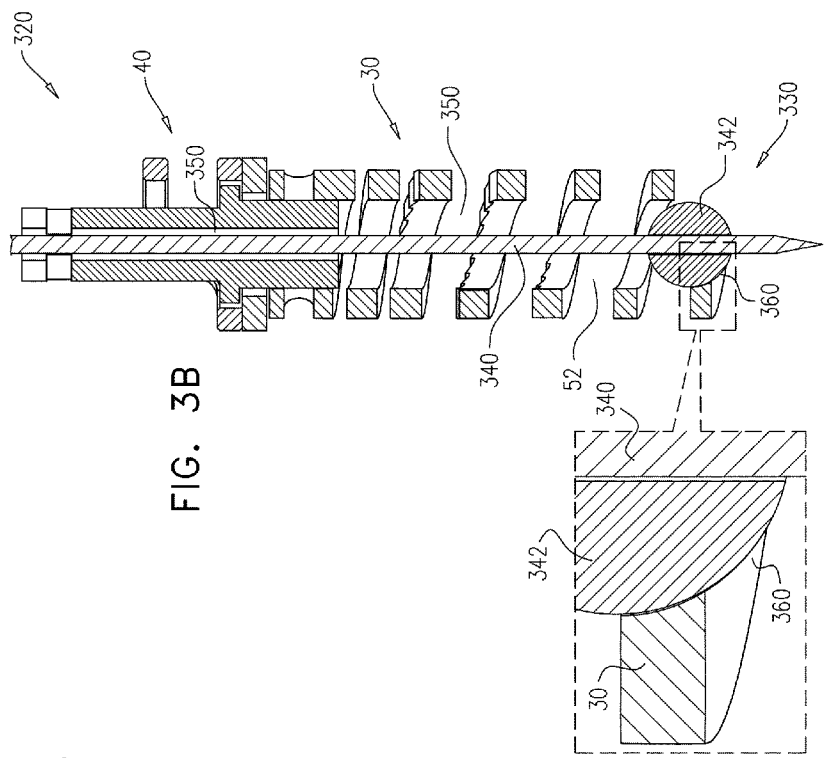
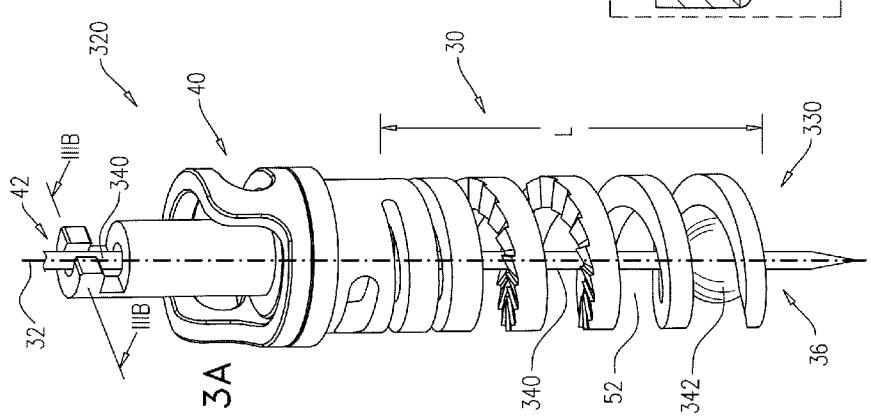
FIG. 3A
FIG. 3B

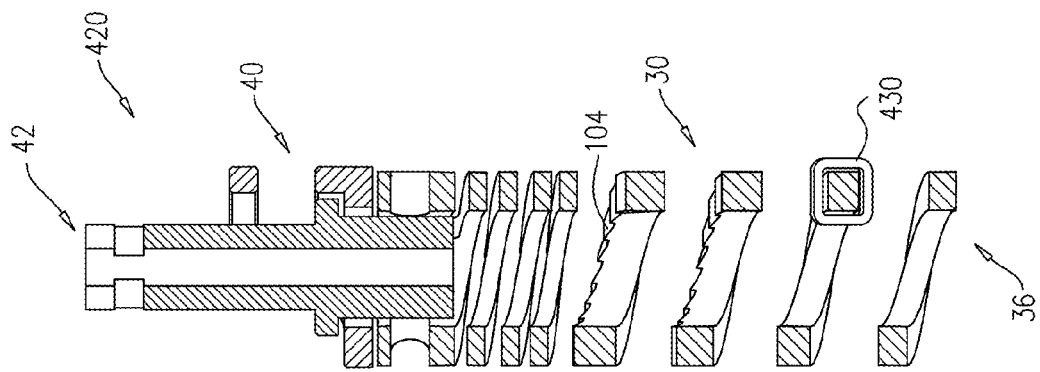
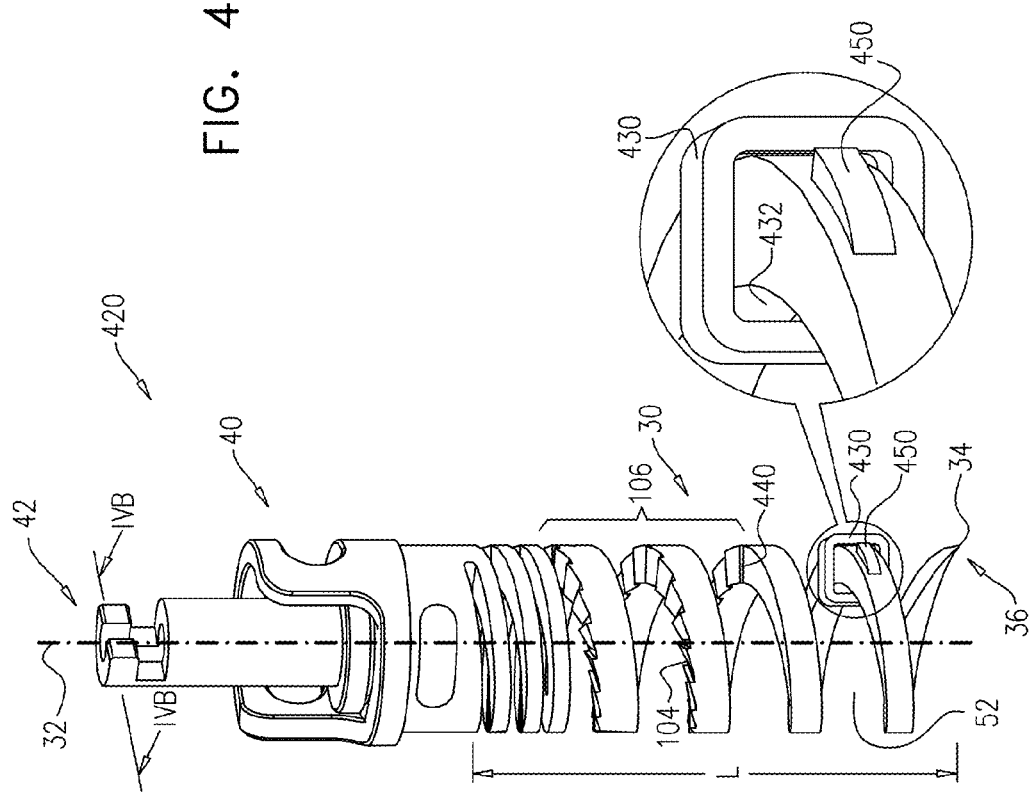
FIG. 4B
FIG. 4A

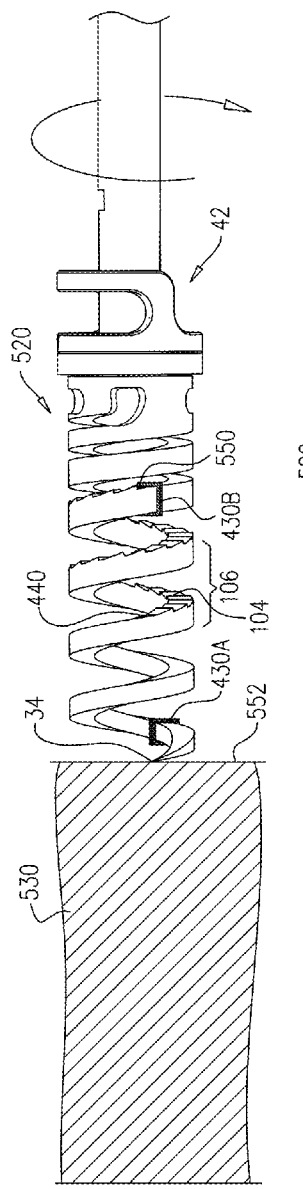
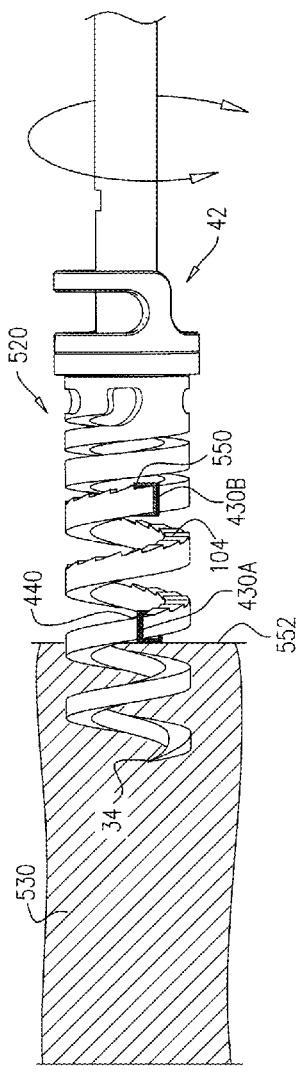
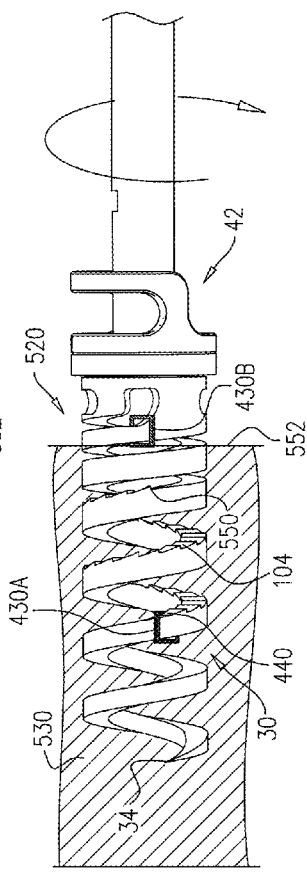
FIG. 5A
FIG. 5B
FIG. 5C

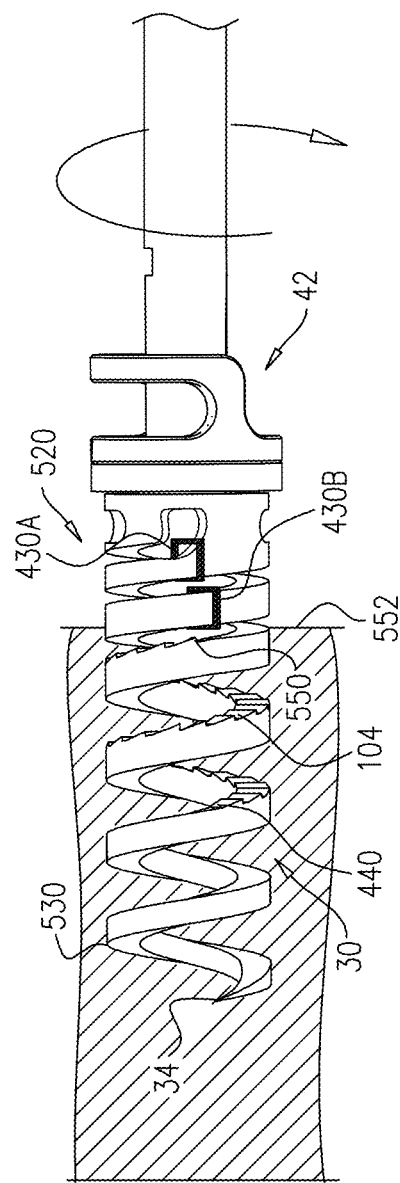

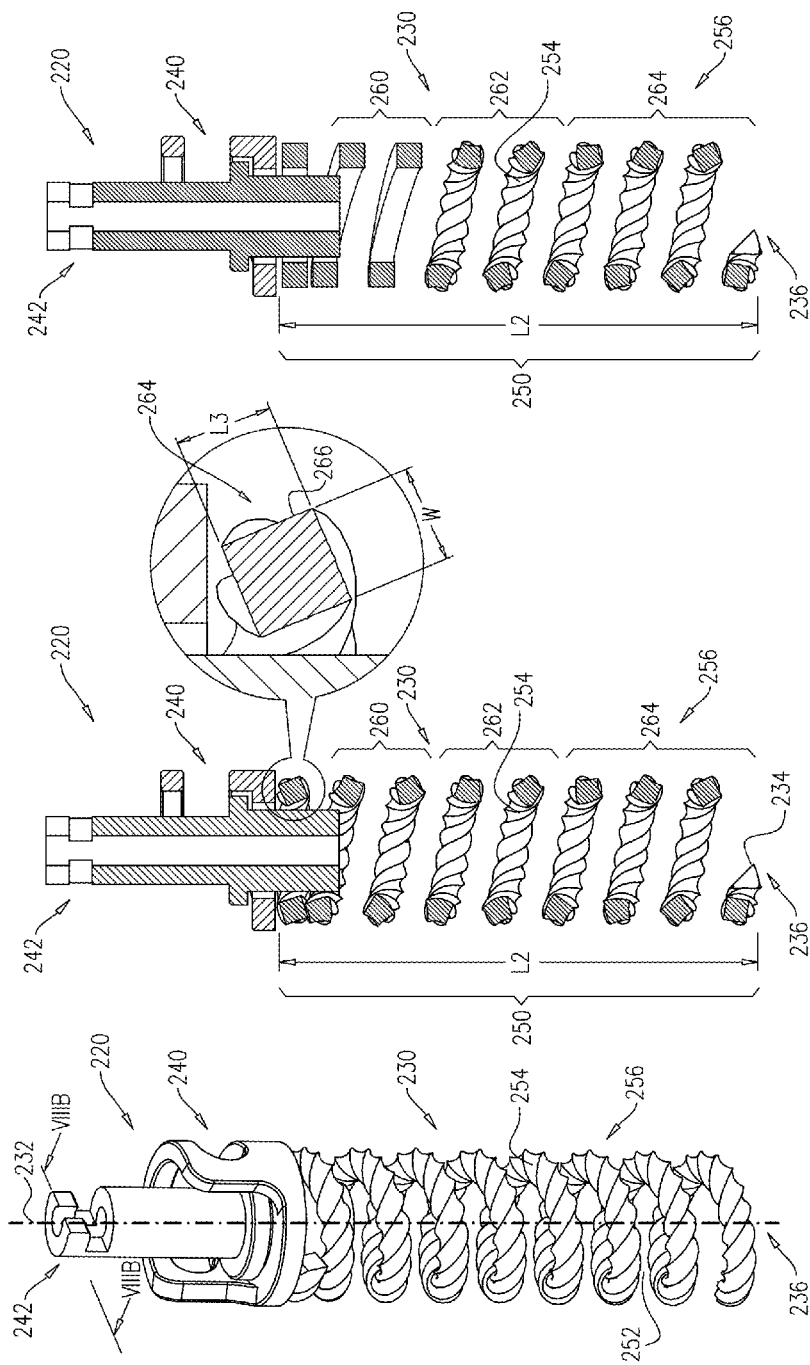

SOFT TISSUE DEPTH-FINDING TOOL

CROSS-REFERENCE TO RELATED APPLICATIONS

The present application is a continuation of U.S. application Ser. No. 14/759,768, filed Jul. 8, 2015, which is the US national state of International Application PCT/IL2014/050027, filed Jan. 9, 2014, which claims from U.S. Provisional Application 61/750,427, filed Jan. 9, 2013, which is assigned to the assignee of the present application and is incorporated herein by reference.

FIELD OF THE APPLICATION

The present invention relates generally to tissue anchors, and specifically to anchors for tissue anchors for implantation in soft tissue, such as cardiac tissue.

BACKGROUND OF THE APPLICATION

Tissue anchors are used for anchoring elements, such as electrode leads or sutures, to tissue, such as bone or soft tissue. Some tissue anchors are shaped so as to define a shaft and screw thread therearound, while other tissue anchors are shaped so as define a helical tissue-coupling element without a shaft.

SUMMARY OF THE APPLICATION

Some applications of the present invention provide tissue anchors, each of which comprises a generally helical tissue-coupling element and, typically, a proximal head. Typically, the helical tissue-coupling element has a generally rectangular, e.g., square, cross section. For some applications, the helical tissue-coupling element has (a) a first axial thickness along a first axial portion of a shaftless helical portion of the helical tissue-coupling element, and (b) a second axial thickness along a second axial portion of the shaftless helical portion more distal than the first axial portion. The second axial thickness is greater than the first axial thickness. The first and second axial thicknesses are measured along a longitudinal axis of the helical tissue-coupling element. Alternatively or additionally, the helical tissue-coupling element has (a) a first axial yield strength along the first axial portion, and (b) a second axial yield strength along the second axial portion (more distal than the first axial portion). The second axial yield strength is greater than the first axial yield strength. Further alternatively or additionally, the helical tissue-coupling element has (a) a first axial stiffness along the first axial portion, and (b) a second axial stiffness along the second axial portion (more distal than the first axial portion). The second axial stiffness is greater than the first axial stiffness.

One result of these differing thicknesses, yield strengths, and/or axial stiffnesses is that if excessive tension is applied to the proximal head, such as by a flexible longitudinal member as described below, the helical tissue-coupling element generally elongates along the first axial portion before along the second axial portion. The first axial portion thus serves as a mechanical fuse. Providing the first axial portion effective reduces the force on the main part of the anchor which holds the anchor in place, thereby reducing or eliminating the danger of unscrewing the anchor, breaking the anchor, or tearing the tissue, both during the implantation procedure and thereafter during long-term implantation of the anchor. Alternatively or additionally, the physician may reduce or cease increasing the tension before the second axial portion elongates, thereby reducing the risk of the elongation causing damage to the tissue in which the second axial portion is implanted, and the risk that the tension will pull the anchor from the tissue. For some applications, the physician senses elongation of the first axial portion in real time while applying the tension, such as by using imaging and/or tactile feedback. The first axial portion may undergo plastic deformation when elongated. As a result, excess force applied to the anchor is absorbed by the first axial portion, instead of detaching the anchor from the tissue, or causing failure elsewhere on the anchor.

For some applications, the helical tissue-coupling element is shaped so as to define (a) a first surface along a first axial surface characteristic portion of the shaftless helical portion of the helical tissue-coupling element, which first surface has a first surface characteristic, and (b) a second surface along a second axial surface characteristic portion of the shaftless helical portion different from the first axial surface characteristic portion. The second surface has a second surface characteristic that is configured to inhibit rotation of the helical tissue-coupling element to a greater extent than does the first surface characteristic. The first surface characteristic may, for example, be a high level of smoothness.

For some applications, the helical tissue-coupling element is configured to rotate in a first rotational direction when being advanced into tissue, and the second surface characteristic is configured to inhibit rotation of the helical tissue-coupling element in the first rotational direction to a lesser extent than in a second rotational direction opposite the first rotational direction. The second surface thus is configured to generally not inhibit the distal advancing (e.g., screwing) of the helical tissue-coupling element into the tissue, and to inhibit the proximal removal (e.g., unscrewing) of the helical tissue-coupling element from the tissue, thereby providing better anchoring of the helical tissue-coupling element in the tissue.

For some applications, the second surface is sawtooth-shaped so as to provide the second surface characteristic. Typically, the sawtooth-shaped second surface does not define any cutting surfaces. Alternatively or additionally, for some applications, the second surface characteristic is surface roughness. For some applications, these varying surface characteristics are implemented in combination with the varying axial thicknesses, yield strengths, and/or stiffnesses described hereinabove.

For some applications, the helical tissue-coupling element includes a shaftless single-helix axial portion, and a shaftless double-helix axial portion joined to the single-helix axial portion at a junction along the helical tissue-coupling element. The shaftless single-helix axial portion is shaped so as to define a single helical element. The shaftless double-helix axial portion is shaped so as to define two helical elements axially offset from each other. The shaftless single- and double-helix portions are thus arranged such that the shaftless single-helix portion axially splits into the shaftless double-helix portion at the junction. Typically, the shaftless double-helix axial portion is proximal to the shaftless single-helix axial portion.

An axial yield strength of the shaftless single-helix axial portion is typically greater than an axial yield strength of the shaftless double-helix axial portion. These differing axial yield strengths may provide the same benefit described above regarding the differing axial yield strengths of the first and second axial portions. In addition, for some applications, the two helical elements of the shaftless double-helix portion are rotationally offset from each other by between 160 and 200 degrees, such as 180 degrees, which may cancel out or reduce any moments of force.

For some applications, along at least a shaftless helical portion of the helical tissue-coupling element, an axial thickness of the helical tissue-coupling element varies while a radial thickness of the helical tissue-coupling element remains constant. The axial thickness is measured along the axis, and the radial thickness is measured perpendicular to the axis.

In general, the tissue anchors described herein provide good tissue anchoring, typically for at least the 500,000 to 1 million cardiac cycles required before cardiac tissue growth firmly implants the anchors. The configurations of the tissue anchors reduce the likelihood of the tissue anchors unscrewing, coming loose with a portion of the tissue, or mechanically breaking.

In some applications of the present invention, the tissue anchor further comprises a radiopaque bead shaped so as to define a hole therethrough. The helical tissue-coupling element passes through the hole of the bead, such that the bead is slidable along the helical tissue-coupling element. The bead thus serves as a marker that indicates a depth of penetration of the tissue-coupling element into soft tissue, such as cardiac tissue.

When rotated, the helical tissue-coupling element penetrates and is advanced into the tissue. The bead does not penetrate the tissue, and thus remains at a surface of the tissue, in contact therewith. As a result, as the tissue-coupling element advances into the tissue, the bead remains stationary and slides along the tissue-coupling element toward the proximal end of the anchor (and toward the head). In other words, the proximal end of the anchor (and the head) move closer to the bead, as measured along the axis. Both the bead and more proximal portions of the anchor (such as the head) are viewed using imaging (e.g., fluoroscopy), and the distance between the bead and the proximal end of the anchor (e.g., the head) is estimated and monitored in real time as the anchor is advanced into the tissue. When the bead reaches a desired distance from the head (such as reaches the head itself), the tissue-coupling element has been fully advanced, e.g., screwed, into and embedded in the tissue, and the physician thus ceases rotating the anchor.

Without using a technique such as this for visualizing the advancement of the anchor into the tissue, it is often difficult to ascertain when the tissue anchor has been fully embedded into the tissue, because the tissue is difficult to see in some images, such as fluoroscopic images. As a result, the tissue anchor may inadvertently be insufficiently advanced into the tissue, resulting in poor anchoring in the tissue, or over-advanced into the tissue, possible tearing or otherwise damaging the tissue.

Some applications of the present invention provide a depth-finding tool, which comprises a shaft and a radiopaque bead shaped so as to define a hole therethrough. The shaft and bead are arranged such that the shaft passes through the hole of the bead, such that the bead is slidable along the shaft. The tissue anchor is shaped so as to define a longitudinal channel extending from a proximal end to a distal end thereof. The shaft of the depth-finding tool is removably positioned within the channel, typically coaxially with the longitudinal axis of the anchor. The bead is positioned within the distal portion of the channel. The bead is typically initially positioned at or near the distal end of the tissue anchor. For some applications, the helical tissue-coupling element is shaped so as to define a distal stopper that prevents the bead from advancing distally off of the shaft.

The bead serves as a marker that indicates a depth of penetration of the helical tissue-coupling element into soft tissue, such as cardiac tissue. When rotated, the helical tissue-coupling element penetrates and is advanced into the tissue. The bead does not penetrate the tissue, and thus remains at the surface of the tissue, in contact therewith. As a result, as the tissue-coupling element advances into the tissue, the bead remains stationary, and moves toward the proximal end of the anchor (and toward the head). In other words, the proximal end of the anchor (and the head) move closer to the bead, as measured along the axis.

Both the bead and more proximal portions of the anchor (such as the head) are viewed using imaging (e.g., fluoroscopy), and the distance between the bead and the proximal end of the anchor (e.g., the head) is estimated and monitored in real time as the anchor is advanced into the tissue. When the bead reaches a desired distance from the head (such as reaches the head itself), the tissue-coupling element has been fully advanced, e.g., screwed, into and embedded in the tissue, and the physician thus ceases rotating the anchor. The physician proximally withdraws the shaft from the channel, leaving the bead at the proximal end of an empty space defined by the helix; the helical tissue-coupling element contains the bead.

Without using a technique such as this for visualizing the advancement of the anchor into the tissue, it is often difficult to ascertain when the tissue anchor has been fully embedded into the tissue, because the tissue is difficult to see in some images, such as fluoroscopic images. As a result, the tissue anchor may inadvertently be insufficiently advanced into the tissue, resulting in poor anchoring in the tissue, or over-advanced into the tissue, possible tearing or otherwise damaging the tissue.

In some applications of the present invention, the tissue anchors and tools described herein are used for repairing a tricuspid valve using tension. Typically, the techniques described herein for repairing the tricuspid valve facilitate reducing of tricuspid valve regurgitation by altering the geometry of the tricuspid valve and/or by altering the geometry of the wall of the right atrium of the heart of the patient. In some applications of the present invention, techniques are provided to achieve bicuspidization of the tricuspid valve. For such applications, typically, the anterior leaflet and the septal leaflet are drawn together to enhance coaptation. For some applications, a first tissue-engaging element, which comprises one of the tissue anchors described herein, punctures a portion of cardiac tissue of the patient and is implanted at a first implantation site. A second tissue-engaging element comprises a stent that is implanted at a second implantation site in either the inferior or superior vena cava. A flexible longitudinal member is coupled between the first and the second tissue-engaging elements and used to provide tension between the elements. For some applications, a plurality of first tissue-engaging elements are provided (such as two or three), which are implanted in respective portions of cardiac tissue in a vicinity of the heart valve.

Some applications of the present invention provide a delivery system for delivering the first tissue-engaging element. The first tissue-engaging element may optionally comprise one of the tissue anchors described herein. The delivery system comprises an anchor-deployment tube and a radiopaque marker, which is coupled to a distal end of the anchor-deployment tube, typically by flexible connecting element, such as a spring, a braid, a mesh, or a cut tube. The radiopaque marker and flexible connecting element are initially arranged radially surrounding the first tissue-engaging element, such that the radiopaque marker is axially moveable along the first tissue-engaging element with respect to the distal end of the anchor-deployment tube. The flexible connecting element axially compresses as the marker moves toward the distal end of the anchor-deployment tube. The flexible connecting element biases the marker distally. The marker may have any appropriate shape, such as a disc.

As the physician begins to rotate the first tissue-engaging element into tissue at the first implantation site, the spring pushes the marker distally against the surface of the tissue. The marker does not penetrate the tissue, and thus remains at the surface of the tissue, in contact therewith. As a result, as the physician continues to rotate the first tissue-engaging element further into the tissue, the surface of the tissue holds the marker in place, bringing the marker closer to the distal end of the anchor-deployment tube and closer to the head of the first tissue-engaging element.

Both the marker and more proximal portions of the anchor (such as the head) are viewed using imaging (e.g., fluoroscopy), and the distance between the market and the proximal end of the anchor (e.g., the head) is estimated and monitored in real time as the anchor is advanced into the tissue. When the marker reaches a desired distance from the head (such as reaches the head itself), the tissue-coupling element has been fully advanced, e.g., screwed, into and embedded in the tissue, and the physician thus ceases rotating the anchor.

There is therefore provided, in accordance with an application of the present invention, apparatus including a tissue anchor, which includes a helical tissue-coupling element disposed about a longitudinal axis thereof and having a distal tissue-penetrating tip, wherein the helical tissue-coupling element has:

a first axial thickness along a first axial portion of a shaftless helical portion of the helical tissue-coupling element, and a second axial thickness along a second axial portion of the shaftless helical portion more distal than the first axial portion, which second axial thickness is greater than the first axial thickness, the first and second axial thicknesses being measured along the axis.

For some applications, the helical tissue-coupling element has:

a first axial yield strength along the first axial portion of the helical tissue-coupling element, a second axial yield strength along the second axial portion of the helical tissue-coupling element, which second axial yield strength is greater than the first axial yield strength, and a third axial yield strength along the third axial portion, which third axial yield strength is less than the second axial yield strength.

Alternatively or additionally, for some applications:

the first and the second axial portions are shaftless helical portions of the helical tissue-coupling elements, and the helical tissue-coupling element has:

a first axial thickness along the first axial portion, and a second axial thickness along the second axial portion, which second axial thickness is greater than the first axial thickness, the first and second axial thicknesses being measured along the axis.

For some applications, the helical tissue-coupling element has a third axial thickness along the third axial portion, which third axial thickness is less than the second axial thickness, the third axial thickness being measured along the axis.

For some applications, the helical tissue-coupling element has a third axial thickness along a third axial portion more distal than the second axial portion, which third axial thickness is less than the second axial thickness, the third axial thickness being measured along the axis.

Alternatively or additionally, for some applications, the tissue anchor is shaped so as to define a head at a proximal end thereof, and the apparatus further includes a flexible longitudinal member, which is coupled to the head.

For some applications:

the distal tissue-penetrating tip is at a distal end of the tissue anchor, and the tissue anchor is shaped so as to define a longitudinal channel extending from a proximal end of the anchor to the distal end, and the apparatus further includes a depth-finding tool, which includes a radiopaque bead shaped so as to define a hole therethrough, which bead is positioned within the channel, such that the bead is slidable along the channel.

For some applications, the depth-finding tool further includes a shaft that is removably positioned within the channel, such that the shaft passes through the hole of the bead, and such that the bead is slidable along the shaft and along the channel. For some applications, a distal tip of the shaft is sharp.

For some applications, the helical tissue-coupling element is shaped so as to define a distal stopper that prevents the radiopaque bead from advancing distally off of the shaft.

For any of the applications described above:

the tissue anchor may be shaped so as to define a head at the proximal end thereof, the helical tissue-coupling element may be shaped so as to define and radially surround an empty space that extends along at least 75% of an axial length of the helical tissue-coupling element, a distal portion of the channel may coincide with the empty space, a proximal portion of the channel may be defined by the head, the distal portion of the channel may be wider than the proximal portion of the channel, and the bead may be positioned within the distal portion of the channel, in the empty space.

For any of the applications described above, the depth-finding tool may further include a wire, which is at least partially disposed within the channel, and which couples the bead to the a proximal portion of the tissue anchor, thereby preventing the bead from exiting the distal end of the tissue anchor. For some applications, the wire is shaped as a helical spring.

There is further provided, in accordance with an application of the present invention, apparatus including a tissue anchor, which includes a helical tissue-coupling element disposed about a longitudinal axis thereof and having a distal tissue-penetrating tip, wherein the helical tissue-coupling element has:

a first axial yield strength along a first axial portion of the helical tissue-coupling element, a second axial yield strength along a second axial portion of the helical tissue-coupling element more distal than the first axial portion, which second axial yield strength is greater than the first axial yield strength, and a third axial yield strength along a third axial portion more distal than the second axial portion, which third axial yield strength is less than the second axial yield strength.

For some applications, the tissue anchor is shaped so as to define a head at a proximal end thereof, and the first axial portion extends to the head.

Alternatively or additionally, for some applications, the tissue anchor is shaped so as to define a head at a proximal end thereof, and the apparatus further includes a flexible longitudinal member, which is coupled to the head.

There is still further provided, in accordance with an application of the present invention, apparatus including a tissue anchor, which includes a helical tissue-coupling element disposed about a longitudinal axis thereof and having a distal tissue-penetrating tip, wherein the helical tissue-coupling element has:

a first axial stiffness along a first axial portion of the helical tissue-coupling element, a second axial stiffness along a second axial portion of the helical tissue-coupling element more distal than the first axial portion, which second axial stiffness is greater than the first axial stiffness, and a third axial stiffness along a third axial portion more distal than the second axial portion, which third axial stiffness is less than the second axial stiffness.

For some applications, the tissue anchor is shaped so as to define a head at a proximal end thereof, and the first axial portion extends to the head.

Alternatively or additionally, for some applications, the tissue anchor is shaped so as to define a head at a proximal end thereof, and the apparatus further includes a flexible longitudinal member, which is coupled to the head.

There is additionally provided, in accordance with an application of the present invention, apparatus including a tissue anchor, which includes a helical tissue-coupling element disposed about a longitudinal axis thereof and having a distal tissue-penetrating tip, wherein the helical tissue-coupling element is configured to rotate in a first rotational direction when being advanced into tissue, and has:

a first surface along a first axial portion of a shaftless helical portion of the helical tissue-coupling element, which first surface has a first surface characteristic, and a second surface along a second axial portion of the shaftless helical portion different from the first axial portion, which second surface has a second surface characteristic that is configured to (a) inhibit rotation of the helical tissue-coupling element to a greater extent than does the first surface characteristic, and (b) inhibit rotation of the helical tissue-coupling element in the first rotational direction to a lesser extent than in a second rotational direction opposite the first rotational direction, wherein the first and the second surfaces face in a same spatial direction.

For some applications, the second axial portion is more proximal than the first axial portion. Alternatively, the second axial portion is more distal than the first axial portion.

For some applications, the tissue anchor is shaped so as to define a head at a proximal end thereof, and the first axial portion extends to the head.

For some applications, the spatial direction is proximal, and the first and the second surfaces face proximally.

For some applications, the tissue anchor is shaped so as to define a head at a proximal end thereof, and the apparatus further includes a flexible longitudinal member, which is coupled to the head.

For any of the applications described above, the helical tissue-coupling element may have a third surface along a third axial portion of the helical tissue-coupling element more distal than the second axial portion, which third surface has a third surface characteristic that is configured to inhibit the rotation of the helical tissue-coupling element to a lesser extent than does the second surface characteristic, and the first, the second, and the third surfaces may face in the same spatial direction. For some applications, the first and third surface characteristics are configured to inhibit the rotation of the helical tissue-coupling element to a same extent.

For any of the applications described above, the second surface may be sawtooth-shaped so as to provide the second surface characteristic. For some applications, the sawtooth-shaped second surface does not define any cutting surfaces. For some applications, the spatial direction is proximal, and the first and the second surfaces face proximally.

For any of the applications described above, the second surface characteristic may be surface roughness. For some applications, the spatial direction is proximal, and the first and the second surfaces face proximally.

For any of the applications described above, an axial length of the first axial portion may be at least 10% of an axial length of the helical tissue-coupling element, and/or the axial length of the first axial portion may be no more than 30% of the axial length of the helical tissue-coupling element.

There is yet additionally provided, in accordance with an application of the present invention, apparatus including a tissue anchor, which includes:

a radiopaque bead shaped so as to define a hole therethrough; and a helical tissue-coupling element, which includes a shaftless helical portion that (a) is disposed about a longitudinal axis thereof, (b) has a distal tissue-penetrating tip, and (c) has an axial length of at least 3 mm, and wherein the shaftless helical portion passes through the hole of the bead, such that the bead is slidable along the shaftless helical portion.

For some applications, the axial length is less than 10 mm.

For some applications, the shaftless helical portion extends along at least 75% of the axial length of the helical tissue-coupling element.

For some applications, the tissue anchor is shaped so as to define a head at a proximal end thereof, and the apparatus further includes a flexible longitudinal member, which is coupled to the head.

For any of the applications described above, the radiopaque bead may include a plurality of radiopaque beads shaped so as to define respective holes therethrough, and the helical tissue-coupling element may pass through the holes of the beads such that the beads are slidable along the helical tissue-coupling element.

For some applications:

the helical tissue-coupling element is disposed about a longitudinal axis thereof, and has: (a) a first surface along a first axial portion of the shaftless helical portion, which first surface has a first surface characteristic, and (b) a second surface along a second axial portion of the shaftless helical portion different from the first axial portion, which second surface has a second surface characteristic that is configured to inhibit rotation of the helical tissue-coupling element to a greater extent than does the first surface characteristic, a first one of the beads is initially positioned distal to the second axial portion, and a second one of the beads is initially positioned proximal to the second axial portion.

For some applications, the radiopaque beads include exactly two radiopaque beads.

For any of the applications described above, the helical tissue-coupling element may be disposed about a longitudinal axis thereof, and may have: (a) a first surface along a first axial portion of the shaftless helical portion, which first surface has a first surface characteristic, and (b) a second surface along a second axial portion of the shaftless helical portion different from the first axial portion, which second surface has a second surface characteristic that is configured to inhibit rotation of the helical tissue-coupling element to a greater extent than does the first surface characteristic, and the bead may be initially positioned distal to the second axial portion. For some applications, the helical tissue-coupling element is configured to rotate in a first rotational direction when being advanced into tissue, and the second surface characteristic is configured to inhibit rotation of the helical tissue-coupling element in the first rotational direction to a lesser extent than in a second rotational direction opposite the first rotational direction.

There is also provided, in accordance with an application of the present invention, apparatus including a tissue anchor, which includes a helical tissue-coupling element, which is disposed about a longitudinal axis thereof, has a distal tissue-penetrating tip, and includes at least:

a shaftless single-helix axial portion, which is shaped so as to define a single helical element, and a shaftless double-helix axial portion joined to the shaftless single-helix axial portion at a junction along the helical tissue-coupling element.

For some applications, the helical tissue-coupling element has an axial length of at least 3 mm, and the shaftless single- and double-helix portions collectively extend along at least 75% of the axial length of the helical tissue-coupling element.

For some applications, the shaftless double-helix portion is shaped so as to define two helical elements rotationally offset from each other by between 160 and 200 degrees.

For some applications, the tissue anchor is shaped so as to define a head at a proximal end thereof, and the apparatus further includes a flexible longitudinal member, which is coupled to the head.

For some applications, the shaftless single-helix axial portion has a single-helix axial thickness at a first location on the shaftless single-helix axial portion at a distance of 250 microns from the junction, the distance measured circumferentially around the helical tissue-coupling element; the shaftless double-helix axial portion, including the two helical elements and the axial gap, has a double-helix axial thickness at a second location on the shaftless double-helix axial portion at the distance from the junction, the single-helix and double-helix axial thicknesses being measured along the axis; and the double-helix axial thickness equals between 75% and 120% of the single-helix axial thickness.

For some applications, the shaftless double-helix portion is shaped so as to define two helical elements axially offset from each other, separated by an axial gap.

For any of the applications described above, an axial yield strength of the shaftless single-helix axial portion may be greater than an axial yield strength of the shaftless double-helix axial portion. For some applications, the axial yield strength of the shaftless single-helix axial portion is at least 120% of the axial yield strength of the shaftless double-helix axial portion.

For any of the applications described above, the shaftless double-helix axial portion may be proximal to the shaftless single-helix axial portion. For some applications, the tissue anchor is shaped so as to define a head at a proximal end thereof, and wherein the shaftless double-helix axial portion extends to the head.

There is further provided, in accordance with an application of the present invention, apparatus including:

a tissue anchor, which (a) includes a helical tissue-coupling element which has a distal tissue-penetrating tip at a distal end of the tissue anchor, and (b) is shaped so as to define a longitudinal channel extending from a proximal end of the anchor to the distal end; and a depth-finding tool, which includes a radiopaque bead shaped so as to define a hole therethrough, which bead is positioned within the channel, such that the bead is slidable along the channel.

For some applications, the depth-finding tool further includes a shaft that is removably positioned within the channel, such that the shaft passes through the hole of the bead, and such that the bead is slidable along the shaft and along the channel. For some applications, a distal tip of the shaft is sharp. For some applications, the helical tissue-coupling element is shaped so as to define a distal stopper that prevents the radiopaque bead from advancing distally off of the shaft.

For any of the applications described above:

the tissue anchor may be shaped so as to define a head at the proximal end thereof, the helical tissue-coupling element may be shaped so as to define and radially surround an empty space that extends along at least 75% of an axial length of the helical tissue-coupling element, a distal portion of the channel may coincide with the empty space, a proximal portion of the channel may be defined by the head, the distal portion of the channel may be wider than the proximal portion of the channel, and the bead may be positioned within the distal portion of the channel, in the empty space.

For any of the applications described above, the depth-finding tool may further include a wire, which is at least partially disposed within the channel, and which couples the bead to the a proximal portion of the tissue anchor, thereby preventing the bead from exiting the distal end of the tissue anchor. For some applications, the wire is shaped as a helical spring.

There is still further provided, in accordance with an application of the present invention, apparatus including a tissue anchor, which includes a helical tissue-coupling element disposed about a longitudinal axis thereof and having a distal tissue-penetrating tip, the helical tissue-coupling element including a wire which (a) is shaped as a helix, (b) has a non-circular cross section, and (c) is twisted about its longitudinal axis, so as to define a ridged surface.

For some applications, the wire is twisted about its longitudinal axis at between 1 and 5 twists per cm of a length the wire before it is shaped into the helix.

For some applications, the cross section is shaped as a polygon.

For some applications, the tissue anchor is shaped so as to define a head at a proximal end thereof, and the apparatus further includes a flexible longitudinal member, which is coupled to the head.

For any of the applications described above, the helical tissue-coupling element may have:

a first axial stiffness along a first axial portion of the helical tissue-coupling element, a second axial stiffness along a second axial portion of the helical tissue-coupling element more distal than the first axial portion, which second axial stiffness is greater than the first axial stiffness, and a third axial stiffness along a third axial portion more distal than the second axial portion, which third axial stiffness is less than the second axial stiffness.

For some applications, the tissue anchor is shaped so as to define a head at a proximal end thereof, and the first axial portion extends to the head.

There is additionally provided, in accordance with an application of the present invention, apparatus for use with a tissue anchor, the apparatus including a delivery system, which includes:

an anchor-deployment tube;

a flexible connecting element selected from the group consisting of: a spring, a braid, a mesh, and a cut tube;

a radiopaque marker, which is coupled to a distal end of the anchor-deployment tube by the flexible connecting element, wherein the radiopaque marker and the flexible connecting element are arranged radially surrounding the tissue anchor, such that the radiopaque marker is axially moveable along the tissue anchor with respect to the distal end, and wherein the flexible connecting element is arranged so as to axially compress as the marker moves toward the distal end.

For some applications, the radiopaque marker is shaped as a disc.

There is also provided, in accordance with an application of the present invention, a method including:

providing a tissue anchor, which includes a helical tissue-coupling element disposed about a longitudinal axis thereof and having a distal tissue-penetrating tip, wherein the helical tissue-coupling element has (a) a first axial yield strength along a first axial portion of the helical tissue-coupling element, (b) a second axial yield strength along a second axial portion of the helical tissue-coupling element more distal than the first axial portion, which second axial yield strength is greater than the first axial yield strength, and (c) a third axial yield strength along a third axial portion more distal than the second axial portion, which third axial yield strength is less than the second axial yield strength; and advancing the helical tissue-coupling element into soft tissue.

For some applications:

providing the tissue anchor includes providing the tissue anchor in which the helical tissue-coupling element has (a) a first axial yield strength along the first axial portion of the helical tissue-coupling element, and (b) a second axial yield strength along the second axial portion of the helical tissue-coupling element, which second axial yield strength is greater than the first axial yield strength, and the method further includes:

applying tension to a proximal head of the tissue anchor; and sensing elongation of the first axial portion while applying the tension.

For some applications, providing the tissue anchor includes providing the tissue anchor in which the helical tissue-coupling element has (a) a first axial stiffness along the first axial portion of the helical tissue-coupling element, (b) a second axial stiffness along the second axial portion of the helical tissue-coupling element, which second axial stiffness is greater than the first axial stiffness, and (c) a third axial stiffness along the third axial portion, which third axial stiffness is less than the second axial stiffness.

For some applications, providing the tissue anchor includes providing the tissue anchor in which (i) the first and the second axial portions are shaftless helical portions of the helical tissue-coupling elements, and (ii) the helical tissue-coupling element has (a) a first axial thickness along the first axial portion, and (b) a second axial thickness along the second axial portion, which second axial thickness is greater than the first axial thickness, the first and second axial thicknesses being measured along the axis. For some applications, providing the tissue anchor includes providing the tissue anchor in which the helical tissue-coupling element has a third axial thickness along the third axial portion, which third axial thickness is less than the second axial thickness, the third axial thickness being measured along the axis.

For some applications, the method further includes applying tension to a proximal head of the tissue anchor. For some applications, applying the tension includes sensing elongation of the first axial portion while applying the tension. For some applications, sensing the elongation includes sensing the elongation using imaging. Alternatively or additionally, sensing the elongation includes sensing the elongation using tactile feedback. For some applications, applying the tension includes pulling on a flexible longitudinal member that is coupled to the proximal head.

For some applications, advancing the helical tissue-coupling element into the soft tissue includes advancing the second and the third axial portions completely into the soft tissue, and leaving at least a portion of the first axial portion outside of the soft tissue. For some applications, leaving the at least a portion of the first axial portion outside of the soft tissue includes leaving the first axial portion entirely outside of the soft tissue.

For some applications, providing the tissue anchor includes providing the tissue anchor shaped so as to define a head at a proximal end thereof, and the first axial portion extends to the head.

For some applications:

wherein providing the tissue anchor includes providing the tissue anchor (a) in which the distal tissue-penetrating tip is at a distal end of the tissue anchor, and (b) which is shaped so as to define a longitudinal channel extending from a proximal end of the anchor to the distal end, wherein the method further includes providing a depth-finding tool, which includes a radiopaque bead shaped so as to define a hole therethrough, which bead is positioned within the channel, such that the bead is slidable along the channel, and wherein advancing the helical tissue-coupling element into the soft tissue includes advancing the helical tissue-coupling element into the soft tissue, such that the bead comes into contact with and remains at a surface of the soft tissue.

For some applications, providing the depth-finding tool includes providing the depth-finding tool further including a shaft that is removably positioned within the channel, such that the shaft passes through the hole of the bead, and the bead is slidable along the shaft and along the channel. For some applications, the method further includes proximally withdrawing the shaft from the channel, leaving the bead in the channel. For some applications, providing the depth-finding tool includes providing the depth-finding tool in which a distal tip of the shaft is sharp. For some applications, the method further includes advancing the shaft into the soft tissue while advancing the helical tissue-coupling element into the soft tissue. For some applications, the method further includes, after fully advancing the helical tissue-coupling element into the soft tissue, proximally withdrawing the shaft from the channel, leaving the bead in the channel.

For some applications, the method further includes, before advancing the helical tissue-coupling element into the soft tissue, inserting the sharp distal tip of the shaft into the soft tissue slightly, in order to prevent sliding of the depth-finding tool and the anchor on a surface of the soft tissue before advancing the anchor into the tissue.

For some applications, the method further includes: viewing the bead and a proximal portion of the soft tissue anchor using imaging; and assessing a depth of penetration of the helical tissue-coupling element into the soft tissue by estimating a distance between the bead and the proximal portion of the tissue anchor.

For some applications, providing the depth-finding tool includes providing the depth-finding tool further including a wire, which is at least partially disposed within the channel, and which couples the bead to the a proximal portion of the tissue anchor, thereby preventing the bead from exiting the distal end of the tissue anchor. For some applications, wherein providing the depth-finding tool includes providing the depth-finding tool in which the wire is shaped as a helical spring.

For some applications:
  providing the tissue anchor includes providing the tissue anchor in which:
    the tissue anchor is shaped so as to define a head at the proximal end thereof,
    the helical tissue-coupling element is shaped so as to define and radially surround an empty space that extends along at least 75% of an axial length of the helical tissue-coupling element,
    a distal portion of the channel coincides with the empty space,
    a proximal portion of the channel is defined by the head, and
    the distal portion of the channel is wider than the proximal portion of the channel, and
  providing the depth-finding tool includes providing the depth-finding tool in which the bead is positioned within the distal portion of the channel, in the empty space.

There is further provided, in accordance with an inventive concept 1 of the present invention, a method comprising:
  providing a tissue anchor, which includes a helical tissue-coupling element disposed about a longitudinal axis thereof and having a distal tissue-penetrating tip, wherein the helical tissue-coupling element has (a) a first axial yield strength along a first axial portion of the helical tissue-coupling element, and (b) a second axial yield strength along a second axial portion of the helical tissue-coupling element more distal than the first axial portion, which second axial yield strength is greater than the first axial yield strength;
  advancing the helical tissue-coupling element into soft tissue;
  applying tension to a proximal head of the tissue anchor; and
  sensing elongation of the first axial portion while applying the tension.

Inventive concept 2. The method according to inventive concept 1, wherein sensing the elongation comprises sensing the elongation using imaging.

Inventive concept 3. The method according to inventive concept 1, wherein sensing the elongation comprises sensing the elongation using tactile feedback.

Inventive concept 4. The method according to inventive concept 1, wherein applying the tension comprises pulling on a flexible longitudinal member that is coupled to the proximal head.

Inventive concept 5. The method according to inventive concept 1, wherein advancing the helical tissue-coupling element into the soft tissue comprises advancing the second axial portion completely into the soft tissue, and leaving at least a portion of the first axial portion outside of the soft tissue.

Inventive concept 6. The method according to inventive concept 5, wherein leaving the at least a portion of the first axial portion outside of the soft tissue comprises leaving the first axial portion entirely outside of the soft tissue.

Inventive concept 7. The method according to inventive concept 1, wherein providing the tissue anchor comprises providing the tissue anchor shaped so as to define a head at a proximal end thereof, and wherein the first axial portion extends to the head.

There is still further provided, in accordance with an inventive concept 8 of the present invention, a method comprising:
  providing a tissue anchor, which includes a helical tissue-coupling element disposed about a longitudinal axis thereof and having a distal tissue-penetrating tip, wherein the helical tissue-coupling element has (a) a first axial stiffness along a first axial portion of the helical tissue-coupling element, (b) a second axial stiffness along a second axial portion of the helical tissue-coupling element more distal than the first axial portion, which second axial stiffness is greater than the first axial stiffness, and (c) a third axial stiffness along a third axial portion more distal than the second axial portion, which third axial stiffness is less than the second axial stiffness; and
  advancing the helical tissue-coupling element into soft tissue.

Inventive concept 9. The method according to inventive concept 8, further comprising applying tension to a proximal head of the tissue anchor.

Inventive concept 10. The method according to inventive concept 9, wherein applying the tension comprises sensing elongation of the first axial portion while applying the tension.

Inventive concept 11. The method according to inventive concept 10, wherein sensing the elongation comprises sensing the elongation using imaging.

Inventive concept 12. The method according to inventive concept 10, wherein sensing the elongation comprises sensing the elongation using tactile feedback.

Inventive concept 13. The method according to inventive concept 9, wherein applying the tension comprises pulling on a flexible longitudinal member that is coupled to the proximal head.

Inventive concept 14. The method according to inventive concept 8, wherein advancing the helical tissue-coupling element into the soft tissue comprises advancing the second and the third axial portions completely into the soft tissue, and leaving at least a portion of the first axial portion outside of the soft tissue.

Inventive concept 15. The method according to inventive concept 14, wherein leaving the at least a portion of the first axial portion outside of the soft tissue comprises leaving the first axial portion entirely outside of the soft tissue.

Inventive concept 16. The method according to inventive concept 8, wherein providing the tissue anchor comprises providing the tissue anchor shaped so as to define a head at a proximal end thereof, and wherein the first axial portion extends to the head.

There is additionally provided, in accordance with an inventive concept 17 of the present invention, a method comprising:

providing a tissue anchor, which (a) includes a helical tissue-coupling element which has a distal tissue-penetrating tip at a distal end of the tissue anchor, and (b) is shaped so as to define a longitudinal channel extending from a proximal end of the anchor to the distal end;

providing a depth-finding tool, which includes a radiopaque bead shaped so as to define a hole therethrough, which bead is positioned within the channel, such that the bead is slidable along the channel; and advancing the helical tissue-coupling element into soft tissue, such that the bead comes into contact with and remains at a surface of the soft tissue.

Inventive concept 18. The method according to inventive concept 17, wherein providing the depth-finding tool comprises providing the depth-finding tool further including a shaft that is removably positioned within the channel, such that the shaft passes through the hole of the bead, and the bead is slidable along the shaft and along the channel.

Inventive concept 19. The method according to inventive concept 18, further comprising proximally withdrawing the shaft from the channel, leaving the bead in the channel.

Inventive concept 20. The method according to inventive concept 18, wherein providing the depth-finding tool comprises providing the depth-finding tool in which a distal tip of the shaft is sharp.

Inventive concept 21. The method according to inventive concept 20, further comprising advancing the shaft into the soft tissue while advancing the helical tissue-coupling element into the soft tissue.

Inventive concept 22. The method according to inventive concept 21, further comprising, after fully advancing the helical tissue-coupling element into the soft tissue, proximally withdrawing the shaft from the channel, leaving the bead in the channel.

Inventive concept 23. The method according to inventive concept 20, further comprising, before advancing the helical tissue-coupling element into the soft tissue, inserting the sharp distal tip of the shaft into the soft tissue slightly, in order to prevent sliding of the depth-finding tool and the anchor on a surface of the soft tissue before advancing the anchor into the tissue.

Inventive concept 24. The method according to inventive concept 17, further comprising:

viewing the bead and a proximal portion of the soft tissue anchor using imaging; and assessing a depth of penetration of the helical tissue-coupling element into the soft tissue by estimating a distance between the bead and the proximal portion of the tissue anchor.

Inventive concept 25. The method according to inventive concept 17, wherein providing the depth-finding tool comprises providing the depth-finding tool further including a wire, which is at least partially disposed within the channel, and which couples the bead to the a proximal portion of the tissue anchor, thereby preventing the bead from exiting the distal end of the tissue anchor.

Inventive concept 26. The method according to inventive concept 25, wherein providing the depth-finding tool comprises providing the depth-finding tool in which the wire is shaped as a helical spring.

Inventive concept 27. The method according to inventive concept 17, wherein providing the tissue anchor comprises providing the tissue anchor in which:

the tissue anchor is shaped so as to define a head at the proximal end thereof, the helical tissue-coupling element is shaped so as to define and radially surround an empty space that extends along at least 75% of an axial length of the helical tissue-coupling element, a distal portion of the channel coincides with the empty space, a proximal portion of the channel is defined by the head, and the distal portion of the channel is wider than the proximal portion of the channel, and wherein providing the depth-finding tool comprises providing the depth-finding tool in which the bead is positioned within the distal portion of the channel, in the empty space.

There is yet additionally provided, in accordance with an inventive concept 28 of the present invention, a method comprising:

providing a tissue anchor, which includes a helical tissue-coupling element disposed about a longitudinal axis thereof and having a distal tissue-penetrating tip, wherein the helical tissue-coupling element has (a) a first axial thickness along a first axial portion of a shaftless helical portion of the helical tissue-coupling element, and (b) a second axial thickness along a second axial portion of the shaftless helical portion more distal than the first axial portion, which second axial thickness is greater than the first axial thickness, the first and second axial thicknesses being measured along the axis; and advancing the helical tissue-coupling element into soft tissue.

Inventive concept 29. The method according to inventive concept 28, further comprising applying tension to a proximal head of the tissue anchor.

Inventive concept 30. The method according to inventive concept 29, wherein applying the tension comprises sensing elongation of the first axial portion while applying the tension.

Inventive concept 31. The method according to inventive concept 30, wherein sensing the elongation comprises sensing the elongation using imaging.

Inventive concept 32. The method according to inventive concept 30, wherein sensing the elongation comprises sensing the elongation using tactile feedback.

Inventive concept 33. The method according to inventive concept 29, wherein applying the tension comprises pulling on a flexible longitudinal member that is coupled to the proximal head.

Inventive concept 34. The method according to inventive concept 28, wherein advancing the helical tissue-coupling element into the soft tissue comprises advancing the second axial portion completely into the soft tissue, and leaving at least a portion of the first axial portion outside of the soft tissue.

Inventive concept 35. The method according to inventive concept 34, wherein leaving the at least a portion of the first axial portion outside of the soft tissue comprises leaving the first axial portion entirely outside of the soft tissue.

Inventive concept 36. The method according to inventive concept 28, wherein providing the tissue anchor comprises providing the tissue anchor in which the helical tissue-coupling element has a third axial thickness along a third axial portion more distal than the second axial portion, which third axial thickness is less than the second axial thickness, the third axial thickness being measured along the axis.

There is also provided, in accordance with an inventive concept 37 of the present invention, a method comprising:
providing a tissue anchor, which includes a helical tissue-coupling element disposed about a longitudinal axis thereof and having a distal tissue-penetrating tip, wherein the helical tissue-coupling element has (a) a first axial stiffness along a first axial portion of the helical tissue-coupling element, and (b) a second axial stiffness along a second axial portion of the helical tissue-coupling element more distal than the first axial portion, which second axial stiffness is greater than the first axial stiffness;
advancing the helical tissue-coupling element into soft tissue;
applying tension to a proximal head of the tissue anchor; and
sensing elongation of the first axial portion while applying the tension.

Inventive concept 38. The method according to inventive concept 37, wherein sensing the elongation comprises sensing the elongation using imaging.

Inventive concept 39. The method according to inventive concept 37, wherein sensing the elongation comprises sensing the elongation using tactile feedback.

Inventive concept 40. The method according to inventive concept 37, wherein applying the tension comprises pulling on a flexible longitudinal member that is coupled to the proximal head.

Inventive concept 41. The method according to inventive concept 37, wherein advancing the helical tissue-coupling element into the soft tissue comprises advancing the second axial portion completely into the soft tissue, and leaving at least a portion of the first axial portion outside of the soft tissue.

Inventive concept 42. The method according to inventive concept 41, wherein leaving the at least a portion of the first axial portion outside of the soft tissue comprises leaving the first axial portion entirely outside of the soft tissue.

Inventive concept 43. The method according to inventive concept 37, wherein providing the tissue anchor comprises providing the tissue anchor shaped so as to define a head at a proximal end thereof, and wherein the first axial portion extends to the head.

There is further provided, in accordance with an inventive concept 44 of the present invention, a method comprising:
providing a tissue anchor, which includes a helical tissue-coupling element disposed about a longitudinal axis thereof and having a distal tissue-penetrating tip, wherein the helical tissue-coupling element has (a) a first surface along a first axial portion of a shaftless helical portion of the helical tissue-coupling element, which first surface has a first surface characteristic, and (b) a second surface along a second axial portion of the shaftless helical portion different from the first axial portion; and
advancing the helical tissue-coupling element into soft tissue,
wherein the second surface has a second surface characteristic that is configured to, immediately upon advancing of the helical tissue-coupling element into the soft tissue, mechanically inhibit rotation of the helical tissue-coupling element to a greater extent than does the first surface characteristic, and
wherein the first and the second surfaces face in a same spatial direction.

Inventive concept 45. The method according to inventive concept 44, wherein advancing the helical tissue-coupling element into the soft tissue comprises advancing the second axial portion completely into the soft tissue.

Inventive concept 46. The method according to inventive concept 44, wherein providing the tissue anchor comprises providing the tissue anchor in which the second axial portion is more proximal than the first axial portion.

Inventive concept 47. The method according to inventive concept 44, wherein providing the tissue anchor comprises providing the tissue anchor in which the second axial portion is more distal than the first axial portion.

Inventive concept 48. The method according to inventive concept 47, wherein advancing the helical tissue-coupling element into the soft tissue comprises advancing the second axial portion completely into the soft tissue, and leaving at least a portion of the first axial portion outside of the soft tissue.

Inventive concept 49. The method according to inventive concept 44, wherein providing the tissue anchor comprises providing the tissue anchor in which the helical tissue-coupling element has a third surface along a third axial portion of the helical tissue-coupling element more distal than the second axial portion, which third surface has a third surface characteristic that is configured to inhibit the rotation of the helical tissue-coupling element to a lesser extent than does the second surface characteristic, and the first, the second, and the third surfaces face in the same spatial direction.

Inventive concept 50. The method according to inventive concept 49, wherein providing the tissue anchor comprises providing the tissue anchor in which the first and third surface characteristics are configured to inhibit the rotation of the helical tissue-coupling element to a same extent.

Inventive concept 51. The method according to inventive concept 44,
wherein advancing the helical tissue-coupling element into the soft tissue comprises rotating the helical tissue-coupling element in a first rotational direction, and
wherein providing the tissue anchor comprises providing the tissue anchor in which the second surface characteristic is configured to inhibit rotation of the helical tissue-coupling element in the first rotational direction to a lesser extent than in a second rotational direction opposite the first rotational direction.

Inventive concept 52. The method according to inventive concept 44, wherein providing the tissue anchor comprises providing the tissue anchor in which the tissue anchor is shaped so as to define a head at a proximal end thereof, and wherein the first axial portion extends to the head.

Inventive concept 53. The method according to inventive concept 44, wherein the spatial direction is proximal, and wherein providing the tissue anchor comprises providing the tissue anchor in which the first and the second surfaces face proximally.

Inventive concept 54. The method according to inventive concept 44, wherein providing the tissue anchor comprises providing the tissue anchor in which the second surface is sawtooth-shaped so as to provide the second surface characteristic.

Inventive concept 55. The method according to inventive concept 54, wherein providing the tissue anchor comprises providing the tissue anchor in which the sawtooth-shaped second surface does not define any cutting surfaces.

Inventive concept 56. The method according to inventive concept 54, wherein the spatial direction is proximal, and wherein providing the tissue anchor comprises providing the tissue anchor in which the first and the second surfaces face proximally.

Inventive concept 57. The method according to inventive concept 44, wherein the second surface characteristic is surface roughness.

Inventive concept 58. The method according to inventive concept 57, wherein the spatial direction is proximal, and wherein providing the tissue anchor comprises providing the tissue anchor in which the first and the second surfaces face proximally.

There is still further provided, in accordance with an inventive concept 59 of the present invention, a method comprising:

providing a tissue anchor, which includes (a) a radiopaque bead shaped so as to define a hole therethrough, and (b) a helical tissue-coupling element, which includes a shaftless helical portion that (i) is disposed about a longitudinal axis thereof, (ii) has a distal tissue-penetrating tip, and (iii) has an axial length of at least 3 mm, wherein the shaftless helical portion passes through the hole of the bead, such that the bead is slidable along the shaftless helical portion; and advancing the helical tissue-coupling element into soft tissue, such that the bead comes into contact with and remains at a surface of the soft tissue.

Inventive concept 60. The method according to inventive concept 59, further comprising:

viewing the bead and a proximal portion of the soft tissue anchor using imaging; and assessing a depth of penetration of the helical tissue-coupling element into the soft tissue by estimating a distance between the bead and the proximal portion of the tissue anchor.

Inventive concept 61. The method according to inventive concept 59, wherein providing the tissue anchor comprises providing the tissue anchor in which the radiopaque bead includes a plurality of radiopaque beads shaped so as to define respective holes therethrough, and the helical tissue-coupling element passes through the holes of the beads such that the beads are slidable along the helical tissue-coupling element.

Inventive concept 62. The method according to inventive concept 61, wherein providing the tissue anchor comprises providing the tissue anchor in which the helical tissue-coupling element is disposed about a longitudinal axis thereof, and has (a) a first surface along a first axial portion of the shaftless helical portion, which first surface has a first surface characteristic, and (b) a second surface along a second axial portion of the shaftless helical portion different from the first axial portion, which second surface has a second surface characteristic that is configured to inhibit rotation of the helical tissue-coupling element to a greater extent than does the first surface characteristic, and wherein advancing comprises beginning the advancing when a first one of the beads is initially positioned distal to the second axial portion, and a second one of the beads is initially positioned proximal to the second axial portion.

Inventive concept 63. The method according to inventive concept 62, wherein advancing further comprises monitoring a position of the first bead with respect to a distal end of the second axial portion.

Inventive concept 64. The method according to inventive concept 63, wherein advancing further comprises:

ceasing the advancing when the first bead reaches the distal end of the second axial portion;

thereafter, applying tension to a proximal head of the tissue anchor, and assessing whether the tissue anchor is placed in an appropriate location; and thereafter, if the tissue anchor is placed in the appropriate location:

continuing the advancing at least until a portion of the second axial portion is within the soft tissue;

viewing the second bead and the proximal portion of the soft tissue anchor using imaging; and assessing a depth of penetration of the helical tissue-coupling element into the soft tissue by estimating a distance between the second bead and the proximal portion of the tissue anchor.

Inventive concept 65. The method according to inventive concept 61, wherein providing the tissue anchor comprises providing the tissue anchor in which the radiopaque beads include exactly two radiopaque beads.

Inventive concept 66. The method according to inventive concept 59, wherein providing the tissue anchor comprises providing the tissue anchor in which the helical tissue-coupling element is disposed about a longitudinal axis thereof, and has (a) a first surface along a first axial portion of the shaftless helical portion, which first surface has a first surface characteristic, and (b) a second surface along a second axial portion of the shaftless helical portion different from the first axial portion, which second surface has a second surface characteristic that is configured to inhibit rotation of the helical tissue-coupling element to a greater extent than does the first surface characteristic, and wherein advancing comprises beginning the advancing when the bead is initially positioned distal to the second axial portion.

Inventive concept 67. The method according to inventive concept 66, wherein advancing further comprises monitoring a position of the bead with respect to a distal end of the second axial portion.

Inventive concept 68. The method according to inventive concept 67, wherein advancing further comprises:

ceasing the advancing when the bead reaches the distal end of the second axial portion;

thereafter, applying tension to a proximal head of the tissue anchor, and assessing whether the tissue anchor is placed in an appropriate location; and thereafter, if the tissue anchor is placed in the appropriate location, continuing the advancing at least until a portion of the second axial portion is within the soft tissue.

Inventive concept 69. The method according to inventive concept 66, wherein providing the tissue anchor comprises providing the tissue anchor in which the helical tissue-coupling element is configured to rotate in a first rotational direction when being advanced into tissue, and the second surface characteristic is configured to inhibit rotation of the helical tissue-coupling element in the first rotational direction to a lesser extent than in a second rotational direction opposite the first rotational direction.

Inventive concept 70. The method according to inventive concept 59, wherein providing the tissue anchor comprises providing the tissue anchor in which the shaftless helical portion extends along at least 75% of the axial length of the helical tissue-coupling element.

There is additionally provided, in accordance with an inventive concept 71 of the present invention, a method comprising:

providing a tissue anchor, which includes a helical tissue-coupling element, which is disposed about a longitudinal axis thereof, has a distal tissue-penetrating tip, and includes at least (a) a shaftless single-helix axial portion, which is shaped so as to define a single helical element, and (b) a shaftless double-helix axial portion joined to the shaftless single-helix axial portion at a junction along the helical tissue-coupling element; and advancing the helical tissue-coupling element into soft tissue.

Inventive concept 72. The method according to inventive concept 71, further comprising applying tension to a proximal head of the tissue anchor.

Inventive concept 73. The method according to inventive concept 72, wherein providing the tissue anchor comprises providing the tissue anchor in which the shaftless double-helix axial portion is proximal to the shaftless single-helix axial portion, and wherein applying the tension comprises sensing elongation of the shaftless double-helix axial portion while applying the tension.

Inventive concept 74. The method according to inventive concept 73, wherein sensing the elongation comprises sensing the elongation using imaging.

Inventive concept 75. The method according to inventive concept 73, wherein sensing the elongation comprises sensing the elongation using tactile feedback.

Inventive concept 76. The method according to inventive concept 73, wherein providing the tissue anchor comprises providing the tissue anchor in which the shaftless double-helix axial portion extends to the head.

Inventive concept 77. The method according to inventive concept 72, wherein applying the tension comprises pulling on a flexible longitudinal member that is coupled to the proximal head.

Inventive concept 78. The method according to inventive concept 71, wherein advancing the helical tissue-coupling element into the soft tissue comprises advancing the shaftless single-helix axial portion completely into the soft tissue, and leaving at least a portion of the shaftless double-helix axial portion outside of the soft tissue.

Inventive concept 79. The method according to inventive concept 78, wherein leaving the at least a portion of the shaftless double-helix axial portion outside of the soft tissue comprises leaving the shaftless double-helix axial portion entirely outside of the soft tissue.

Inventive concept 80. The method according to inventive concept 71, wherein providing the tissue anchor comprises providing the tissue anchor in which an axial yield strength of the shaftless single-helix axial portion is greater than an axial yield strength of the shaftless double-helix axial portion.

Inventive concept 81. The method according to inventive concept 80, wherein providing the tissue anchor comprises providing the tissue anchor in which the axial yield strength of the shaftless single-helix axial portion is at least 120% of the axial yield strength of the shaftless double-helix axial portion.

Inventive concept 82. The method according to inventive concept 71, wherein providing the tissue anchor comprises providing the tissue anchor in which the shaftless double-helix portion is shaped so as to define two helical elements axially offset from each other, separated by an axial gap.

Inventive concept 83. The method according to inventive concept 71, providing the tissue anchor comprises providing the tissue anchor in which:

the shaftless single-helix axial portion has a single-helix axial thickness at a first location on the shaftless single-helix axial portion at a distance of 250 microns from the junction, the distance measured circumferentially around the helical tissue-coupling element, the shaftless double-helix axial portion, including the two helical elements and the axial gap, has a double-helix axial thickness at a second location on the shaftless double-helix axial portion at the distance from the junction, the single-helix and double-helix axial thicknesses being measured along the axis, and the double-helix axial thickness equals between 75% and 120% of the single-helix axial thickness.

Inventive concept 84. The method according to inventive concept 71, wherein providing the tissue anchor comprises providing the tissue anchor in which the helical tissue-coupling element has an axial length of at least 3 mm, and wherein the shaftless single-and double-helix portions collectively extend along at least 75% of the axial length of the helical tissue-coupling element.

Inventive concept 85. The method according to inventive concept 71, wherein providing the tissue anchor comprises providing the tissue anchor in which the shaftless double-helix portion is shaped so as to define two helical elements rotationally offset from each other by between 160 and 200 degrees.

There is yet additionally provided, in accordance with an inventive concept 86 of the present invention, a method comprising:

providing a tissue anchor, which comprises a helical tissue-coupling element disposed about a longitudinal axis thereof and having a distal tissue-penetrating tip, the helical tissue-coupling element comprising a wire which (a) is shaped as a helix, (b) has a non-circular cross section, and (c) is twisted about its longitudinal axis, so as to define a ridged surface;

advancing the helical tissue-coupling element into soft tissue.

Inventive concept 87. The method according to inventive concept 86, wherein providing the tissue anchor comprises providing the tissue anchor in which the cross section is shaped as a polygon.

Inventive concept 88. The method according to inventive concept 86, wherein providing the tissue anchor comprises providing the tissue anchor in which the helical tissue-coupling element has (a) a first axial stiffness along a first axial portion of the helical tissue-coupling element, (b) a second axial stiffness along a second axial portion of the helical tissue-coupling element more distal than the first axial portion, which second axial stiffness is greater than the first axial stiffness, and (c) a third axial stiffness along a third axial portion more distal than the second axial portion, which third axial stiffness is less than the second axial stiffness.

Inventive concept 89. The method according to inventive concept 88, wherein providing the tissue anchor comprises providing the tissue anchor in which the tissue anchor is shaped so as to define a head at a proximal end thereof, and wherein the first axial portion extends to the head.

Inventive concept 90. The method according to inventive concept 86, wherein providing the tissue anchor comprises providing the tissue anchor in which the tissue anchor is shaped so as to define a head at a proximal end thereof, and the method further comprises a flexible longitudinal member, which is coupled to the head.

There is also provided, in accordance with an inventive concept 91 of the present invention, a method comprising:

advancing a tissue anchor to soft tissue using an anchor-deployment tube, a distal end of which anchor-deployment tube is coupled to a radiopaque marker by a flexible connecting element selected from the group consisting of: a spring, a braid, a mesh, and a cut tube, such that the radiopaque marker and the flexible connecting element are arranged radially surrounding the tissue anchor, such that the radiopaque marker is axially moveable along the tissue anchor with respect to the distal end;

penetrating the tissue anchor into the soft tissue, such that the flexible connecting element pushes the radiopaque marker distally against a surface of the soft tissue; and advancing the tissue anchor into the soft tissue, thereby moving the radiopaque marker toward the distal end, such that the flexible connecting element axially compresses.

Inventive concept 92. The method according to inventive concept 91, wherein the radiopaque marker is shaped as a disc.

Inventive concept 93. The method according to inventive concept 91, wherein the flexible connecting element comprises the spring.

Inventive concept 94. The method according to inventive concept 91, wherein the flexible connecting element comprises the braid.

Inventive concept 95. The method according to inventive concept 91, further comprising:

viewing the radiopaque marker and a proximal portion of the tissue anchor using imaging; and assessing a depth of penetration of the tissue anchor into the soft tissue by estimating a distance between the radiopaque marker and the proximal portion of the tissue anchor.

The present invention will be more fully understood from the following detailed description of embodiments thereof, taken together with the drawings, in which:

BRIEF DESCRIPTION OF THE DRAWINGS

FIGS. 1A-B are schematic illustrations of a tissue anchor, in accordance with an application of the present invention;

FIGS. 2A-B are schematic illustrations of another tissue anchor, in accordance with an application of the present invention;

FIGS. 3A-F are schematic illustrations of a tissue anchor and a depth-finding tool, in accordance with an application of the present invention;

FIGS. 4A-B are schematic illustrations of still another tissue anchor, in accordance with an application of the present invention;

FIGS. 5A-C and 6 are schematic illustrations of another tissue anchor at several stage of implantation in soft tissue, in accordance with respective applications of the present invention;

FIGS. 8A-C are schematic illustrations of yet another tissue anchor, in accordance with respective applications of the present invention.

DETAILED DESCRIPTION OF APPLICATIONS

Figure 3D:
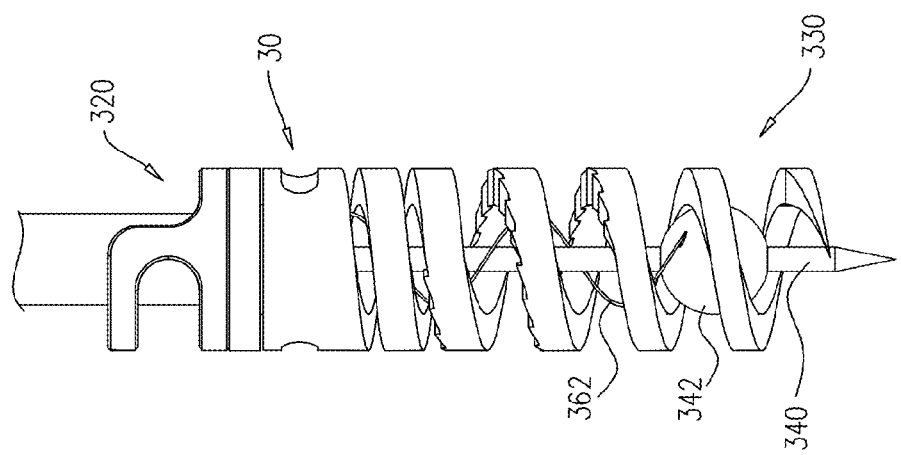

FIGS. 1A-B are schematic illustrations of a tissue anchor 20, in accordance with an application of the present invention. FIG. 1A is an isometric view of the anchor, and FIG. 1B is a cross-sectional view taken along line IB-IB of FIG. 1A. Tissue anchor 20 comprises a generally helical tissue-coupling element 30 disposed about a longitudinal axis 32 thereof and having a distal tissue-penetrating tip 34 at a distal end 36 of tissue anchor 20. Typically, tissue anchor 20 is shaped so as to define a head 40 at a proximal end 42 thereof. Typically, tissue-coupling element 30 has a generally rectangular, e.g., square, cross section.

For some applications, along at least a shaftless helical portion 50 of helical tissue-coupling element 30, an axial thickness $T_A$ of the helical tissue-coupling element varies while a radial thickness $T_R$ of the helical tissue-coupling element remains constant. Axial thickness $T_A$ is measured along axis 32, and radial thickness $T_R$ is measured perpendicular to the axis. (The radial thickness is sometimes referred to in the art as "wall thickness," particularly for configurations in which the helical element is manufactured by cutting a tube, as described hereinbelow. The axial thickness is sometimes referred to in the art as "strut width.")

Typically, radial thickness $T_R$ of helical tissue-coupling element 30 remains constant along at least 50% of an axial length L of the helical tissue-coupling element, such as along 100% of axial length L. Typically, shaftless helical portion 50 extends between 50% and 100% of axial length L of helical tissue-coupling element 30 (In other words, shaftless helical portion 50 does not necessarily extend along the entire axial length L of the helical tissue-coupling element, as labeled in FIG. 1B, even in cases in which the helical tissue-coupling element is shaftless along its entire length L. For example, the shaftless helical portion may extend along only a portion of the shaftless length, such as labeled 50' in FIG. 1B.)

As used in the present application, including in the claims, "shaftless" means lacking a shaft (also sometimes known as a shank) that has an outer surface that is shaped so as to define the helix of helical tissue-coupling element 30. For example, the helical thread of a screw is not shaftless, because the outer surface of the shaft of the screw is shaped so as to define the thread. It is noted that even if a shaft of head 40 extends into helical tissue-coupling element 30, the area into which the shaft of the head extends is still "shaftless" because the shaft of the head does not define the helix, but is merely placed therewithin. It is also noted that if a shaft of a tool, such as shaft 340 of depth-finding tool 330, described hereinbelow with reference to FIGS. 3A, 3B, and 3D, is inserted into helical tissue-coupling element 30, the area into which the shaft of the tool is extends is still "shaftless" because the shaft does not define the helix, but is merely placed therewithin.

For some applications, helical tissue-coupling element 30, as well as the other helical tissue-coupling elements described herein, is manufactured by laser cutting a tube. The tube typically has a constant wall thickness, which provides the constant radial thickness $T_R$. For some applications, helical tissue-coupling element 30 (as well as the other helical tissue-coupling elements described herein) comprises one or more standard implantable alloys known in the art of biomedical implants, such as those described in ISO 5832 parts 1-14. For some applications, helical tissue-coupling element 30 (as well as the other helical tissue-coupling elements described herein) comprises a surface finish or coating, for promoting tissue integration. The surface finish or coating may be applied to one or more surfaces of the element, such as the surface that faces radially inward.

Providing the constant radial thickness $T_R$ along a substantial portion of helical tissue-coupling element 30 provides a constant inner diameter along the portion. In contrast, if the radial thickness varied substantially (e.g., more than 10%), the tissue-coupling element might tear the soft tissue.

Typically, for cardiac applications, axial length L is at least 3 mm, such as at least 4 mm, e.g., at least 4.5 mm, and/or less than 20 mm, such as less than 10 mm, such as to prevent damaging coronary vessels. Shaftless helical portion 50 is shaped so as to define and radially surround an empty space 52, which typically extends along at least 50%, such as 100%, of axial length L. For some applications, empty space 52 has an average diameter of at least 1 mm, no more than 10 mm, and/or between 1 and 10 mm, measured perpendicular to axis 32. This inner diameter corresponds to the inner diameter of helical tissue-coupling element 30.

Typically, for cardiac applications, helical tissue-coupling element 30 has an outer diameter D of between 2 and 8 mm. Typically, outer diameter D varies by less than 10% along entire length L, such as is constant along entire length L. Typically, helical tissue-coupling element 30 has an average axial thickness $T_A$, measured along entire length L, of between 0.2 and 2 mm. Typically, helical tissue-coupling element 30 has an average radial thickness $T_R$, measured along entire length L, of between 0.2 and 2 mm. Typically, radial thickness $T_R$ varies by less than 25% along entire length L, such as is constant along entire length L.

Helical tissue-coupling element 30 behaves as a spring. For some applications, a spring constant of helical tissue-coupling element 30, measured along the entire axial length L thereof, during application of an axial force that does not cause plastic deformation, is between 5 and 50 N/mm.

For some applications, helical tissue-coupling element 30 has:
  at least a first axial thickness $T_{A1}$ along a first axial portion 60 of shaftless helical portion 50 of helical tissue-coupling element 30, which axial thickness is typically between 0.2 and 1 mm, and
  at least a second axial thickness $T_{A2}$ along a second axial portion 62 of shaftless helical portion 50 more distal than first axial portion 60, which second axial thickness $T_{A2}$ is greater than first axial thickness $T_{A1}$, the first and second axial thicknesses being measured along axis 32. Typically, second axial thickness $T_{A2}$ is between 0.2 and 1 mm.

For some applications, first axial portion 60 extends to head 40. In these applications, first axial portion 60 typically does not enter the soft tissue during implantation of the tissue anchor.

One result of these differing thicknesses is that if excessive tension is applied to head 40 at proximal end 42 of anchor 20, such as by flexible longitudinal member 118 as described below, helical tissue-coupling element 30 generally elongates along first axial portion 60 before along second axial portion 62. First axial portion 60 thus serves as a mechanical fuse. As described hereinbelow with reference to FIG. 7C, providing first axial portion 60 effectively reduces the force on the main part of the anchor (e.g., second axial portion 62) which holds the anchor in place, thereby reducing or eliminating the danger of unscrewing the anchor, breaking the anchor, or tearing the tissue, both during the implantation procedure and thereafter during long-term implantation of the anchor. Alternatively or additionally, the physician may reduce or cease increasing the tension before second axial portion 62 elongates, thereby reducing the risk of the elongation causing damage to the tissue in which second axial portion 62 is implanted, and the risk that the tension will pull the anchor from the tissue. For some applications, the physician monitors and senses the length of first axial portion 60 in real time while applying the tension, in order to sense elongation of first axial portion 60. For example, the physician may sense the elongation using imaging (e.g., fluoroscopy, computed tomography, echocardiography, sonography (i.e., ultrasound), or MRI) and/or tactile feedback. Typically, first axial portion 60 undergoes plastic deformation when elongated. As a result, excess force applied to the anchor is absorbed by first axial portion 60, instead of detaching the anchor from the tissue, or causing failure elsewhere on the anchor.

For some applications, helical tissue-coupling element 30 has a third axial thickness $T_{A3}$, and optionally additional axial thicknesses, such as $T_{A4}$ and $T_{A5}$, along a third axial portion 64 of shaftless helical portion 50 of helical tissue-coupling element 30 more distal than second axial portion $T_{A2}$, which third axial thickness $T_{A3}$ is less than second axial thickness $T_{A2}$. Typically, third axial thickness $T_{A3}$ is between 0.2 and 2 mm. For some applications, the axial thickness of third axial portion 64 tapers toward distal end 36, such that $T_{A5}$ is less than $T_{A4}$, which is less than $T_{A3}$. This tapering may provide easier entry of helical tissue-coupling element 30 into the soft tissue. (Third axial thickness $T_{A3}$ may or may not be equal to first axial thickness $T_{A1}$.)

For some applications, the axial thickness of helical tissue-coupling element 30 varies generally continuously along at least an axial portion of the helical tissue-coupling element, such that helical tissue-coupling element 30 has (a) first axial thickness $T_{A1}$ at only a single axial location along first axial portion 60, (b) second axial thickness $T_{A2}$ at only a single axial location along second axial portion 62, and/or (c) third axial thickness $T_{A3}$ at only a single axial location along third axial portion 64.

Alternatively or additionally, the axial thickness of helical tissue-coupling element 30 is constant along one or more axial portions of the helical tissue-coupling element, such that helical tissue-coupling element 30 has (a) first axial thickness $T_{A1}$ at a plurality of axial locations along first axial portion 60, (b) second axial thickness $T_{A2}$ at a plurality of axial locations along second axial portion 62, and/or (c) third axial thickness $T_{A3}$ at a plurality of axial locations along third axial portion 64.

For some applications, helical tissue-coupling element 30 has:
  a first axial stiffness along first axial portion 60 of shaftless helical portion 50 of helical tissue-coupling element 30,
  a second axial stiffness along second axial portion 62 of shaftless helical portion 50 of helical tissue-coupling element 30 (more distal than first axial portion 60), which second axial stiffness is greater than the first axial stiffness, and
  optionally, a third axial stiffness along third axial portion 64 of shaftless helical portion 50 of helical tissue-coupling element 30 (more distal than second axial portion 62), which third axial stiffness is less than the second axial stiffness (the third axial stiffness may or may not be equal to the first axial stiffness).

As used in the present application, including in the claims, "axial stiffness" means the extent to which the helical tissue-coupling element resists axial elastic elongation in response to an applied axial force.

For some applications, the second axial stiffness is at least 120% of the first axial stiffness. For some applications, the first axial stiffness is between 1 and 100 N/mm, and/or the second axial stiffness is between 1.2 and 200 N/mm. For some applications, the second axial stiffness is at least 120% of the third axial stiffness. For some applications, the third axial stiffness is between 1 and 100 N/mm.

These varying axial stiffnesses may be achieved by varying the thicknesses of the axial portions, as described above. Alternatively, these varying axial stiffnesses may be achieved by varying thickness, geometric shape, and/or material properties. For example, material properties may be varied by local heat treatment.

For some applications, helical tissue-coupling element 30 has:
- a first axial yield strength along first axial portion 60 of shaftless helical portion 50 of helical tissue-coupling element 30,
- a second axial yield strength along second axial portion 62 of shaftless helical portion 50 of helical tissue-coupling element 30 (more distal than first axial portion 60), which second axial yield strength is greater than the first axial yield strength, and
- optionally, a third axial yield strength along third axial portion 64 of shaftless helical portion 50 of helical tissue-coupling element 30 (more distal than second axial portion 62), which third axial yield strength is less than the second axial yield strength (the third axial yield strength may be equal to or different from the first axial yield strength).

As used in the present application, including in the claims, "axial yield strength" means the stress at which the helical tissue-coupling element begins to axially elongate plastically, rather than only elastically.

For some applications, the second axial yield strength is at least 120% of the first axial yield strength. For some applications, the first axial yield strength is between 1 and 100 N/mm2, and/or the second axial yield strength is between 1.2 and 200 N/mm2. For some applications, the second axial yield strength is at least 120% of the third axial yield strength. For some applications, the third axial stiffness is between 0.5 and 100 N/mm2.

One result of these differing axial stiffnesses and/or yield strengths is that if excessive tension is applied to head 40 at proximal end 42 of anchor 20, helical tissue-coupling element 30 generally elongates along first axial portion 60 before along second axial portion 62, such that first axial portion 60 serves as a mechanical fuse. As described hereinbelow with reference to FIG. 7C, providing first axial portion 60 effectively reduces the force on the main part of the anchor (e.g., second axial portion 62) which holds the anchor in place, thereby reducing or eliminating the danger of unscrewing the anchor, breaking the anchor, or tearing the tissue, both during the implantation procedure and thereafter during long-term implantation of the anchor. Alternatively or additionally, the physician may reduce or cease increasing the tension before second axial portion 62 elongates, thereby reducing the risk of the elongation causing damage to the tissue in which second axial portion 62 is implanted, and the risk that the tension will pull the anchor from the tissue. For some applications, the physician monitors, such as using imaging (e.g., fluoroscopy, computed tomography, echocardiography, sonography, or MRI) or tactile feedback, the length of first axial portion 60 in real time while applying the tension, in order to sense elongation of first axial portion 60. Typically, first axial portion 60 undergoes plastic deformation when elongated. As a result, excess force applied to the anchor is absorbed by first axial portion 60, instead of detaching the anchor from the tissue, or causing failure elsewhere on the anchor.

For some applications, the axial stiffness of helical tissue-coupling element 30 varies generally continuously along at least an axial portion of the helical tissue-coupling element, such that helical tissue-coupling element 30 has (a) the first axial stiffness at only a single axial location along first axial portion 60, (b) the second axial stiffness at only a single axial location along second axial portion 62, and/or (c) the third axial stiffness at only a single axial location along third axial portion 64.

Alternatively or additionally, the axial stiffness of helical tissue-coupling element 30 is constant along one or more axial portions of the helical tissue-coupling element, such that helical tissue-coupling element 30 has (a) the first axial stiffness at a plurality of axial locations along first axial portion 60, (b) the second axial stiffness at a plurality of axial locations along second axial portion 62, and/or (c) the third axial stiffness at a plurality of axial locations along third axial portion 64.

For some applications, the axial yield strength of helical tissue-coupling element 30 varies generally continuously along at least an axial portion of the helical tissue-coupling element, such that helical tissue-coupling element 30 has (a) the first axial yield strength at only a single axial location along first axial portion 60, (b) the second axial yield strength at only a single axial location along second axial portion 62, and/or (c) the third axial yield strength at only a single axial location along third axial portion 64.

Alternatively or additionally, the axial yield strength of helical tissue-coupling element 30 is constant along one or more axial portions of the helical tissue-coupling element, such that helical tissue-coupling element 30 has (a) the first axial yield strength at a plurality of axial locations along first axial portion 60, (b) the second axial yield strength at a plurality of axial locations along second axial portion 62, and/or (c) the third axial yield strength at a plurality of axial locations along third axial portion 64.

For some applications, an axial length of first axial portion 60 is between 10% and 50% of axial length L of helical tissue-coupling element 30. Alternatively or additionally, for some applications, an axial length of second axial portion 62 is between 10% and 50% of axial length L of helical tissue-coupling element 30. Alternatively or additionally, for some applications, an axial length of third axial portion 64 is between 10% and 30% of axial length L of helical tissue-coupling element 30.

Reference is still made to FIGS. 1A-B. For some applications, helical tissue-coupling element 30 is shaped so as to define:
- a first surface 100 along a first axial surface characteristic portion 102 of shaftless helical portion 50 of the helical tissue-coupling element, which first surface 100 has a first surface characteristic (for example, the first surface characteristic may be a high level of smoothness), and
- a second surface 104 along a second axial surface characteristic portion 106 of shaftless helical portion 50 of the helical tissue-coupling element different from first axial surface characteristic portion 102, which second surface 104 has a second surface characteristic that is configured to mechanically inhibit rotation of the helical tissue-coupling element to a greater extent than does the first surface characteristic, immediately upon advancing of the helical tissue-coupling element into tissue (e.g., even before any differential tissue growth that may occur along second surface 104).

First and second surfaces 100 and 104 face in a same spatial direction, such as proximally (as shown), radially outward (not shown), radially inward (not shown), or distally (not shown).

For some applications, second axial surface characteristic portion 106 is more proximal than first axial surface characteristic portion 102 (shown, but not labeled in FIG. 1A; third axial surface characteristic portion 110, described below, may also be considered to be the first axial surface characteristic portion).

Alternatively, second axial surface characteristic portion 106 portion is more distal than first axial surface characteristic portion 102 (as labeled in FIG. 1A). Optionally, first axial surface characteristic portion 102 extends to head 40. Typically, first axial surface characteristic portion 102 does not enter the soft tissue during implantation of the tissue anchor.

For some applications, helical tissue-coupling element 30 is shaped so as to define a third surface 108 along a third axial surface characteristic portion 110 of shaftless helical portion 50 of the helical tissue-coupling element more distal than second axial surface characteristic portion 106, which third surface 108 includes a third surface characteristic that is configured to inhibit the rotation of the helical tissue-coupling element to a lesser extent than does the second surface characteristic (for example, the third surface characteristic may be a high level of smoothness, which may aid with easy insertion of the anchor into soft tissue). First, second, and third surfaces 100, 104, and 108 face in a same spatial direction, such as proximally (as shown), radially outward (not shown), radially inward (not shown), or distally (not shown). For some applications, the first and third surface characteristics are configured to inhibit the rotation of the helical tissue-coupling element to a same extent.

For some applications, helical tissue-coupling element 30 is configured to rotate in a first rotational direction when being advanced into tissue (e.g., clockwise, as shown), and the second surface characteristic is configured to inhibit rotation of helical tissue-coupling element 30 in the first rotational direction to a lesser extent than in a second rotational direction (e.g., counterclockwise) opposite the first rotational direction. Second surface 104 thus is configured to generally not inhibit the distal advancing (e.g., screwing) of the helical tissue-coupling element into the tissue, and inhibit the proximal removal (e.g., unscrewing) of the helical tissue-coupling element from the tissue, in order to provide better anchoring of the helical tissue-coupling element in the tissue.

For some applications, second surface 104 is sawtooth-shaped so as to provide the second surface characteristic. Typically, sawtooth-shaped second surface 104 does not define any cutting surfaces. For some applications, teeth of the sawtooth-shaped second surface have a sharp leading angle β (beta) of between 5 and 25 degrees, and a blunt trailing edge angle γ (gamma) ☐ of between 75 and 120 degrees.

Alternatively or additionally, for some applications, the second surface characteristic is increased surface roughness.

For some applications, an axial length of first axial surface characteristic portion 102 is between 10 and 800 microns, such as between 150 and 800 microns, e.g., between 350 and 600 microns. Alternatively or additionally, for some applications, an axial length of second axial surface characteristic portion 106 is between 10 and 800 microns, such as between 150 and 800 microns, e.g., between 350 and 600 microns. Alternatively or additionally, for some applications, an axial length of third axial surface characteristic portion 110 is between 10 and 800 microns, such as between 150 and 800 microns, e.g., between 150 and 400 microns. Alternatively or additionally, for some application, the axial length of first axial surface characteristic portion 102 is at least 10%, such as at least 25% of the axial length of second axial surface characteristic portion 106, and/or no more than 30% of the axial length of second axial surface characteristic portion 106, for example between 10% and 30% of the axial length of second axial surface characteristic portion 106.

Alternatively or additionally, for some applications, the axial length of first axial surface characteristic portion 102 is between 10% and 30% of axial length L of helical tissue-coupling element 30. Alternatively or additionally, for some applications, an axial length of second axial surface characteristic portion 106 is between 20% and 80% of axial length L of helical tissue-coupling element 30. Alternatively or additionally, for some applications, an axial length of third axial surface characteristic portion 110 is between 10% and 70% of axial length L of helical tissue-coupling element 30.

For some applications, these varying surface characteristics are implemented in combination with the varying axial thicknesses, stiffnesses, and/or yield strengths described hereinabove. For some applications:

first axial surface characteristic portion 102 at least partially axially overlaps, e.g., axially coincides with, first axial portion 60; the smoothness of first axial surface characteristic portion 102 increases the likelihood that first axial portion 60 plastically deforms, rather than breaks or cracks, when force is applied thereto; and second axial surface characteristic portion 106 at least partially axially overlaps, e.g., axially coincides with, second axial portion 62 and/or third axial portion 64, such that the portions of the helical tissue-coupling element having the greatest rotation-inhibition properties and axial thickness, axial stiffness, and/or axial yield strength are the primary load-bearing surfaces.

Alternatively, these varying surface characteristics are implemented without the varying axial thicknesses, stiffnesses, and/or yield strengths described hereinabove.

For some applications, helical tissue-coupling element 30 has one or more of the following characteristics:

along at least shaftless helical portion 50, such as along entire length L, a ratio between (a) an average axial thickness $T_{AF}$ of free space between adjacent turns of the helix and (b) an average axial thickness $T_A$ of the helix is at least 1.5, no more than 6, and/or between 1.5 and 6. The inter-turn free space is occupied by soft tissue once the anchor has been implanted. This ratio may depend in part on the material of the helix. For example, a ratio at or near the lower end of this range may be most appropriate for applications in which the helix comprises stainless steel (e.g., 316LVM), while a ratio at or near the higher end of this range may be most appropriate for applications in which the helix comprises a CoCr alloy along at least shaftless helical portion 50, such as along entire length L, an average axial thickness $T_A$ of between 0.2 and 2 mm;

along at least shaftless helical portion 50, such as along entire length L, an average radial thickness $T_R$ of between 0.2 and 2 mm;

along at least shaftless helical portion 50, such as along entire length L, a helix angle α (alpha) of less than 25 degrees, such as less than 15 degrees; and/or along at least shaftless helical portion 50, such as along entire length L, a ratio of outer diameter D to radial thickness $T_R$ is at least 3, no more than 10, and/or between 3 and 10, such as 5.

The parameters provided for these characteristics provide an acceptable balance in order to meet three competing requirements. If too steep a helix angle is provided, the resulting friction is too low and the anchor may unscrew. On the other hand, if too shallow a helix angle is provided, there may not be enough space between the helical flights for thick enough tissue in order to prevent tissue tear, or a thick enough metal of the helix to prevent plastic deformation.

Reference is still made to FIGS. 1A-B. For some applications, head 40 comprises a shaft 114, which is coupled (e.g., welded) to a proximal end of helical tissue-coupling element 30, typically such that the shaft and the helical tissue-coupling element are rotationally fixed to each other. (The helical tissue-coupling element may have a reduced pitch, or an axially-solid portion, to enable better coupling to the head.) For some applications, head 40 comprises an interface 116, which is coupled to a flexible longitudinal member 118, such as described hereinbelow with reference to FIGS. 7A-D. Optionally, interface 116 is configured to rotate with respect to helical tissue-coupling element 30 and shaft 114, in order to provide freedom of movement to flexible longitudinal member 118 after implantation of the tissue anchor.

Reference is now made to FIGS. 2A-B, which are schematic illustrations of a tissue anchor 120, in accordance with an application of the present invention. FIG. 2A is an isometric view of the anchor, and FIG. 2B is a cross-sectional view taken along line IIB-IIB of FIG. 2A. Tissue anchor 120 comprises a helical tissue-coupling element 130 disposed about a longitudinal axis 132 thereof and having a distal tissue-penetrating tip 134 at a distal end 136 of tissue anchor 120. Typically, tissue anchor 120 is shaped so as to define a head 140 at a proximal end 142 thereof. Tissue anchor 120 may be implemented in combination with the features of tissue anchor 20, described hereinabove with reference to FIGS. 1A-B.

Helical tissue-coupling element 130 includes:
a shaftless single-helix axial portion 150, which is shaped so as to define a single helical element 152, and
a shaftless double-helix axial portion 160 joined to single-helix axial portion 150 at a junction 161 along helical tissue-coupling element 130; shaftless double-helix axial portion 160 is shaped so as to define two helical elements 162 axially offset from each other.

Shaftless single- and double-helix portions 150 and 160 are thus arranged such that shaftless single-helix portion 150 axially splits into shaftless double-helix portion 160 at junction 161. For some applications, shaftless single-helix axial portion 150 extends to distal tip 134. Alternatively or additionally, for some applications, shaftless double-helix axial portion 160 extends to head 140.

Typically, shaftless double-helix axial portion 160 is proximal to shaftless single-helix axial portion 150. Typically, at least a portion of (typically, the entire) shaftless double-helix axial portion 160 is not advanced into the soft tissue, but instead remains outside the tissue.

Typically, even though the total combined axial thickness of both helices is similar to that of the single helix, the moment of inertia is smaller, resulting in an axial yield strength and/or stiffness of shaftless single-helix axial portion 150 that is greater than (e.g., at least 120% greater than) an axial yield strength of shaftless double-helix axial portion 160. For some applications, the axial yield strength of shaftless single-helix axial portion 150 is between 1 and 100 N, and/or the axial yield strength of shaftless double-helix axial portion 160 is between 1.2 and 200 N.

One result of these differing axial yield strengths and/or stiffnesses is that if excessive tension is applied to head 140 at proximal end 142 of anchor 120, helical tissue-coupling element 130 generally elongates along shaftless double-helix axial portion 160 before along shaftless single-helix axial portion 150. Shaftless double-helix axial portion 160 thus serves as a mechanical fuse. As described hereinbelow with reference to FIG. 7C, providing shaftless double-helix axial portion 160 effectively reduces the force applied on the main part of the anchor (e.g., shaftless single-helix axial portion 150) which holds the anchor in place, thereby reducing or eliminating the danger of unscrewing the anchor, breaking the anchor, or tearing the tissue, both during the implantation procedure and thereafter during long-term implantation of the anchor. Alternatively or additionally, the physician may reduce or cease increasing the tension before shaftless single-helix axial portion 150 elongates, thereby reducing the risk of the elongation causing damage to the tissue in which shaftless single-helix axial portion 150 is implanted, and the risk that the tension will pull the anchor from the tissue. For some applications, the physician monitors, such as using imaging (e.g., fluoroscopy, computed tomography, echocardiography, sonography, or MRI), the length of shaftless double-helix axial portion 160 in real time while applying the tension, in order to sense elongation of shaftless double-helix axial portion 160. Alternatively or additionally, the physician may sense the elongation using tactile feedback. Typically, shaftless double-helix axial portion 160 undergoes plastic deformation when elongated. As a result, excess force applied to the anchor is absorbed by shaftless double-helix axial portion 160, instead of detaching the anchor from the tissue, or causing failure elsewhere on the anchor.

For some applications, two helical elements 162 of shaftless double-helix portion 160 are axially offset from each other, separated by an axial gap 164. For some applications:
shaftless single-helix axial portion 150 has a single-helix axial thickness $T_{AS}$ at a first location on shaftless single-helix axial portion 150 at a distance of 250 microns from junction 161, the distance measured circumferentially around helical tissue-coupling element 130,
shaftless double-helix axial portion 160, including two helical elements 162 and axial gap 164, has a double-helix axial thickness $T_{AD}$ at a second location on the shaftless double-helix axial portion at the distance from junction 161, the single-helix and double-helix axial thicknesses being measured along axis 132, and
double-helix axial thickness $T_{AD}$ equals between 75% and 120%, e.g., between 95% and 105%, of single-helix axial thickness $T_{AS}$, such as 100%.

For some applications, shaftless double-helix portion 160 is shaped so as to define two helical elements 162 rotationally offset from each other by between 160 and 200 degrees, such as 180 degrees, which may cancel out or reduce any moments of force.

For some applications in which tissue anchor 120 is shaped so as to define head 140 at proximal end 142, shaftless double-helix axial portion 160 extends to the head. For some applications, helical tissue-coupling element 130 has an axial length of at least 3 mm, and shaftless single- and double-helix portions 150 and 160 collectively extend along at least 75% of the axial length of helical tissue-coupling element 130.

For some applications, tissue anchor 120 is implemented in combination with the features of tissue anchors 20 and/or 220, described herein with reference to FIGS. 1A-B and 8A-C, respectively, and may have the dimensions of these tissue anchors.

Reference is now made to FIGS. 3A-F, which are schematic illustrations of a tissue anchor 320 and a depth-finding tool 330, in accordance with an application of the present invention. FIGS. 3A and 3C-F are isometric views of the anchor and the depth-finding tool, and FIG. 3B is a cross-sectional view taken along line IIIB-IIIB of FIG. 3A. Tissue anchor 320 may be implemented in combination with the features of tissue anchors 20, 120, and/or 220, described herein with reference to FIGS. 1A-B, 2A-B, and 8A-C, respectively. In this configuration, helical tissue-coupling element 30 is shaped so as to define and radially surround empty space 52 that extends along at least 75% of axial length L. In other words, helical tissue-coupling element 30 is not shaped so as to define a shank or shaft, i.e., is shaftless, as defined hereinabove.

Tissue anchor 320 is shaped so as to define a longitudinal channel 350 extending from proximal end 42 to distal end 36. Typically, longitudinal axis 32 runs through the channel, and may be coaxial therewith. Typically, a distal portion of channel 350 coincides with empty space 52, and a proximal portion of the channel is defined by head 40. For some applications, the distal portion of the channel is wider than the proximal portion of the channel, as shown in FIGS. 3A-B.

Depth-finding tool 330 comprises (a) a radiopaque bead 342 shaped so as to define a hole 344 therethrough, and, typically, (b) a shaft 340. Typically, a distal tip of shaft 340 is sharp.

Shaft 340 of depth-finding tool 330 is removably positioned within channel 350, typically coaxially with longitudinal axis 32, such that the shaft passes through the hole of the bead, and the bead is slidable along the shaft. Bead 342 is positioned within the distal portion of the channel, in empty space 52. The bead is typically initially positioned at or near distal end 36 of tissue anchor 320, as shown in FIGS. 3A-B. For some applications, helical tissue-coupling element 30 is shaped so as to define a distal stopper 360 that prevents bead 342 from advancing distally off of shaft 340.

Bead 342 serves as a marker that indicates a depth of penetration of helical tissue-coupling element 30 into soft tissue, such as cardiac tissue. When rotated, helical tissue-coupling element 30 penetrates and is advanced into the tissue. Bead 342 does not penetrate the tissue, and thus remains at the surface of the tissue, in contact therewith. As a result, as the tissue-coupling element advances into the tissue, the bead remains stationary, and moves toward proximal end 42 of anchor 320 (and toward head 40). In other words, proximal end 42 of anchor 320 (and head 40) move closer to bead 342, as measured along axis 32.

Typically, as anchor 320 is screwed into the tissue, shaft 340 of depth-finding tool 330 penetrates and advances into the tissue along with the anchor. For some applications, when the shaft penetrates to a certain depth, the shaft is withdrawn slightly. Typically, after anchor 320 has been fully implanted, shaft 340 is withdrawn entirely from the tissue, and removed from the patient's body. Optionally, the sharp distal tip of shaft 340 is inserted into the tissue slightly, even before insertion of anchor 320, in order to prevent sliding of depth-finding tool 330 and the anchor on the surface of the tissue before commencement of insertion of the anchor into the tissue.

For some applications, depth-finding tool 330 is implemented in combination with techniques described with reference to FIGS. 22A-B of U.S. patent application Ser. No. 13/553,081, filed Jul. 19, 2012, which published as US Patent Application Publication 2013/0018459 and is assigned to the assignee of the present application and is incorporated herein by reference. For these applications, in addition to its function described herein, shaft 340 serves as elongate longitudinal element 2610 described in the '081 application, for reversibly coupling the head of the anchor to the delivery tool. Proximal withdrawal of the shaft unlocks the positive connection of the head of the anchor with the delivery tool.

Both the bead and more proximal portions of the anchor (such as head 40) are viewed using imaging (e.g., fluoroscopy, computed tomography, echocardiography, sonography, or MRI), and the distance between the bead and the proximal end of the anchor (e.g., the head) is estimated and monitored in real time as the anchor is advanced into the tissue. When the bead reaches a desired distance from the head (such as reaches the head itself), the tissue-coupling element has been fully advanced, e.g., screwed, into and embedded in the tissue, and the physician thus ceases rotating the anchor. The physician proximally withdraws shaft 340 from channel 350, leaving the bead at the proximal end of empty space 52; helical tissue-coupling element 30 contains the bead.

Without using a technique such as this for visualizing the advancement of the anchor into the tissue, it is often difficult to ascertain when the tissue anchor has been fully embedded into the tissue, because the tissue is difficult to see in some images, such as fluoroscopic images. As a result, the tissue anchor may inadvertently be insufficiently advanced into the tissue, resulting in poor anchoring in the tissue, or over-advanced into the tissue, possible tearing or otherwise damaging the tissue.

Bead 342 may have any appropriate shape, such as a sphere (as shown) or a disc (not shown). An outer diameter of the bead is typically slightly greater than the inner diameter of empty space 52, in order to provide some friction between the bead and the helical tissue-coupling element 30, and prevent the bead from being free-floating within the helix. For example, the outer diameter of the bead may be between 0.05 microns less than and 100 microns greater than the inner diameter of empty space 52. Alternatively or additionally, the bead comprises a coating which provides some friction between the bead and the helix; the coating may be sheared off as the bead moves proximally through the helix. Further alternatively or additionally, the bead and shaft are configured to provide some friction therebetween. For some applications, the outer diameter of the bead may be between 1 and 5 mm.

Figure 3C:
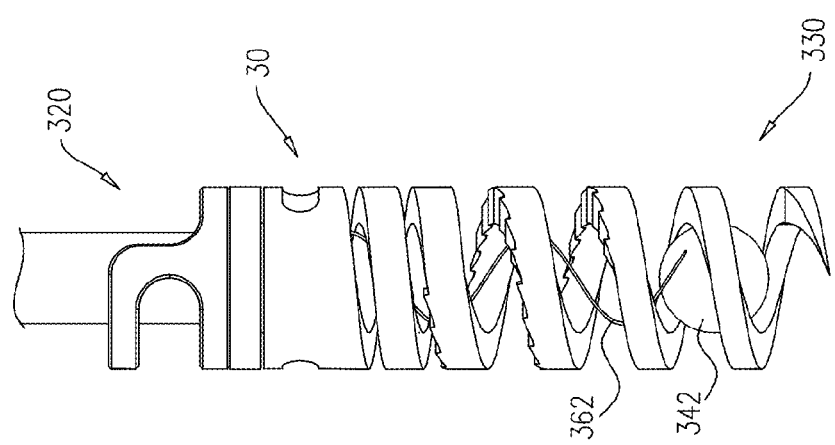

For some applications, as shown in FIGS. 3C and 3D, depth-finding tool 330 further comprises a wire 362 which is at least partially (e.g., entirely) disposed within channel 350 and couples bead 342 to a proximal portion of the anchor, such as head 40, thereby preventing the bead from exiting the distal end of the channel. Wire 362 is very thin, so as to not resist proximal motion of the bead. Wire 362 is optionally shaped as a helical spring having a very low spring constant (as shown). FIG. 3C shows a configuration without shaft 340, while FIG. 3D shows a configuration that includes shaft 340.

Further alternatively or additionally, shaft 340 may be configured to prevent distal motion of the bead. For example, the shaft may be threaded (such as in the opposite direction to the thread of helical tissue-coupling element 30), or be shaped so as to define an angular locking mechanism that locks with the bead at certain rotational orientations, and unlocks with the bead at other rotational orientations.

Figure 3E:
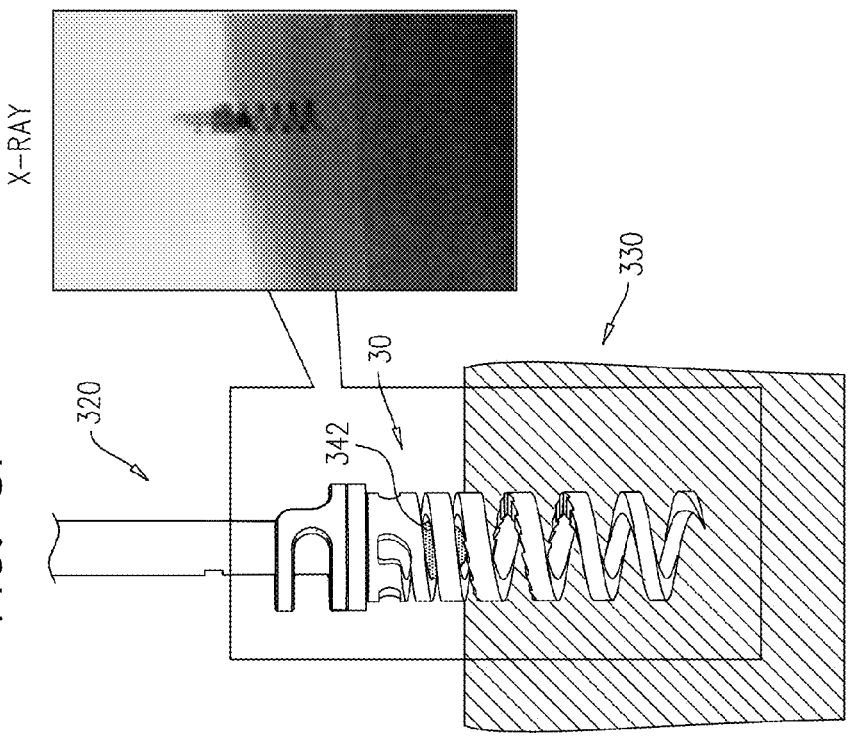
Figure 3F:
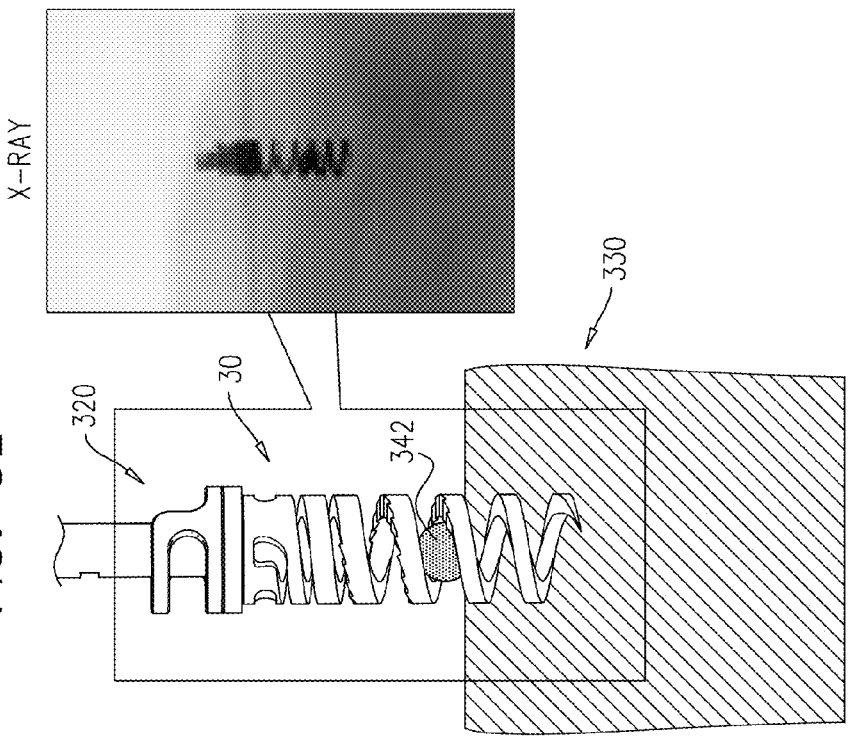

FIGS. 3E-F show a configuration without shaft 340, and include exemplary x-ray images (still radiographs taken using fluoroscopy) taken in an experiment conducted by the inventors in accordance with an application of the present invention. The inventors performed an ex vivo study as a proof-of-concept of some of the imaging-based the depth-finding techniques described herein. In particular, the inventors constructed a mock-up of tissue anchor 320 and depth-finding tool 330. The inventors fabricated a tissue anchor similar to tissue anchor 320, and a depth-finding tool similar to depth-finding tool 330 (the configuration without shaft 340). The inventors used animal meat (ribs) to simulate cardiac soft tissue, and placed the meat under an aluminum block to simulate thoracic fluoroscopy.

FIG. 3E includes an x-ray image of the tissue anchor advanced partially into the tissue, with the radiopaque bead resting against the surface of the tissue. FIG. 3F includes an x-ray image of the tissue anchor and bead after the tissue anchor is fully rotated into the tissue. As can be clearly seen in these x-ray images, the bead remained at the surface of the tissue, and thus moved proximally toward the head of the anchor as the anchor was screwed into the tissue. This ex vivo experiment thus demonstrated that the position of radiopaque bead with respect to the anchor head could be easily seen using conventional x-ray imaging.

Reference is now made to FIGS. 4A-B, which are schematic illustrations of a tissue anchor 420, in accordance with an application of the present invention. FIG. 4A is an isometric view of the anchor, and FIG. 4B is a cross-sectional view taken along line IVB-IVB of FIG. 4A. Tissue anchor 420 may be implemented in combination with the features of tissue anchors 20, 120, and/or 220, described herein with reference to FIGS. 1A-B, 2A-B, and 8A-C, respectively. For some applications, axial thickness $T_A$ is constant, or varies by less than 5%, such as by less than 3%, along all or a portion of the axial length of tissue anchor 420.

Like tissue anchors 20, 120, and 220, tissue anchor 420 comprises helical tissue-coupling element 30, which is disposed about longitudinal axis 32 thereof and has distal tissue-penetrating tip 34. Typically, tissue anchor 420 has axial length L of at least 3 mm, no more than 20 mm (e.g., no more than 10 mm), and/or between 3 mm and 20 mm, such as between 3 mm and 10 mm. Typically, helical tissue-coupling element 30 is shaped so as to define and radially surround empty space 52 that extends along at least 75% of axial length L. In other words, the helical tissue-coupling element typically is not shaped so as to define a shank or shaft.

Tissue anchor 420 further comprises a radiopaque bead 430 shaped so as to define a hole 432 therethrough. Helical tissue-coupling element 30 passes through hole 432 of bead 430, such that the bead is slidable along the helical tissue-coupling element. Bead 430 thus serves as a marker that indicates a depth of penetration of the tissue-coupling element into soft tissue 530, such as cardiac tissue. (Because tissue-coupling element 30 is helical, bead 430 moves along element 30 in a helical path.)

When rotated, helical tissue-coupling element 30 penetrates and is advanced into tissue 530. Bead 430 does not penetrate the tissue, and thus remains at a surface 552 of tissue 530, in contact therewith. As a result, as the tissue-coupling element advances into the tissue, the bead remains stationary and slides along the tissue-coupling element toward proximal end 42 of anchor 420 (and toward head 40). In other words, proximal end 42 of anchor 420 (and head 40) move closer to bead 430, as measured along axis 32. Both the bead and more proximal portions of the anchor (such as head 40) are viewed using imaging (e.g., fluoroscopy, computed tomography, echocardiography, sonography, or MRI), and the distance between the bead and the proximal end of the anchor (e.g., the head) is estimated and monitored in real time as the anchor is advanced into the tissue. When the bead reaches a desired distance from the head (such as reaches the head itself), the tissue-coupling element has been fully advanced, e.g., screwed, into and embedded in the tissue, and the physician thus ceases rotating the anchor.

Without using a technique such as this for visualizing the advancement of the anchor into the tissue, it is often difficult to ascertain when the tissue anchor has been fully embedded into the tissue, because tissue 530 is difficult to see in some images, such as fluoroscopic images. As a result, the tissue anchor may inadvertently be insufficiently advanced into the tissue, resulting in poor anchoring in the tissue, or over-advanced into the tissue, possible tearing or otherwise damaging the tissue.

For some applications, helical tissue-coupling element 30 defines second surface 104, which is configured to inhibit unscrewing of the helical tissue-coupling element from the tissue, as described hereinabove with reference to FIGS. 1A-B. For some of these applications, the physician monitors the position of the bead with respect to a distal end 440 of second axial surface characteristic portion 106 (which defines second surface 104) (either by directly observing the position with respect to distal end 440, or indirectly assessing the position with respect to distal end 440, such as by assessing the position of the bead with respect to proximal end 42 of anchor 420, e.g., head 40). During rotation of helical tissue-coupling element 30 into the tissue, the bead reaches distal end 440 immediately before second axial surface characteristic portion 106 penetrates surface 552 of tissue 530. Before further advancing the helical tissue-coupling element into the tissue, the physician may apply tension, such as described hereinbelow with reference to FIG. 7C, for example in order to assess whether the anchor is placed in an appropriate location for altering the geometry of the right atrium sufficiently to repair the tricuspid valve. If the location is found not to be appropriate, the physician may remove the anchor from the tissue and redeploy the anchor at another location. The anchor may generally be readily unscrewed from the tissue because second surface 104 did not yet enter the tissue. If the location is found to be appropriate, the physician further advances helical tissue-coupling element 30 into the tissue, optionally using bead 430 to assess when the tissue-coupling element has been completely screwed into the tissue.

For some applications, helical tissue-coupling element 30 is shaped so as define a distal stopper 450, which protrudes from the tissue-coupling element sufficiently to prevent motion of bead 430 distally beyond the stopper. Bead 430 is threaded around the tissue-coupling element proximal to the stopper. The stopper may protrude in one or more directions from the tissue-coupling element. By way of illustration, the stopper is shown in FIG. 4A as protruding radially outwardly from the tissue-coupling element.

Bead 430 may have any appropriate shape, such as annular, e.g., a rectangle, e.g., square (as shown). Typically, the inner shape of the bead generally conforms with, and is slightly larger than, the outer cross-sectional shape of the helix.

Reference is now made to FIGS. 5A-C and 6, which are schematic illustrations of a tissue anchor 520 at several stage of implantation in soft tissue 530, in accordance with respective applications of the present invention. Tissue anchor 520 may be implemented in combination with the features of tissue anchors 20, 120, 220, and/or 420 described herein with reference to FIGS. 1A-B, 2A-B, 8A-C, and 4A-B, respectively. For some applications, axial thickness $T_A$ is constant, or varies by less than 5%, such as by less than 3%, along all or a portion of the axial length of tissue anchor 520.

Like tissue anchors 20, 120, 220, and 420, tissue anchor 520 comprises helical tissue-coupling element 30, which is disposed about longitudinal axis 32 thereof and has distal tissue-penetrating tip 34. Typically, tissue anchor 520 has axial length L of at least 3 mm, no more than 20 mm (e.g., no more than 10 mm), and/or between 3 mm and 20 mm, such as between 3 mm and 10 mm. Typically, helical tissue-coupling element 30 is shaped so as to define and radially surround empty space 52 that extends along at least 75% of axial length L. In other words, the helical tissue-coupling element typically is not shaped so as to define a shank or shaft.

Tissue anchor 520 further comprises a plurality of radiopaque beads 430, e.g., exactly two radiopaque beads 430A and 430B, shaped so as to define respective holes therethrough, such as shown in FIGS. 4A-B. Helical tissue-coupling element 30 passes through the holes of beads 430, such that the beads are slidable along the helical tissue-coupling element. Beads 430 thus serve as markers that indicate a depth of penetration of the tissue-coupling element into soft tissue, such as cardiac tissue.

For some applications, helical tissue-coupling element 30 defines second surface 104, which is configured to inhibit unscrewing of the helical tissue-coupling element from the tissue, as described hereinabove with reference to FIGS. 1A-B.

As shown in FIG. 5A, for some applications, before helical tissue-coupling element 30 is inserted into soft tissue 530, such as cardiac tissue, a first radiopaque bead 430A is initially positioned near distal tissue-penetrating tip 34, distal to distal end 440 of second axial surface characteristic portion 106 (which defines second surface 104), and a second radiopaque bead 430B is initially positioned proximal to and near a proximal end 550 of second axial surface characteristic portion 106.

As shown in FIG. 5B, the physician begins advancing helical tissue-coupling element 30 into tissue 530. When rotated, helical tissue-coupling element 30 penetrates and is advanced into the tissue. First bead 430A does not penetrate the tissue, and thus remains at surface 552 of the tissue, in contact therewith. As a result, as the tissue-coupling element advances into the tissue, first bead 430A remains stationary and slides along the tissue-coupling element toward proximal end 42 of anchor 520 (and toward head 40). In other words, proximal end 42 and anchor 520 (and head 40) move closer to first bead 430A, as measured along axis 32. In addition, first bead 430A moves closer to second bead 430B, which has advanced distally as the anchor is screwed into the tissue. Both the beads and more proximal portions of the anchor (such as head 40) are viewed using imaging (e.g., fluoroscopy, computed tomography, echocardiography, sonography, or MRI), and the distance between first bead 430A and the proximal end of the anchor (e.g., the head), and/or between first and second beads 430A and 430B, is estimated and monitored in real time as the anchor is advanced into the tissue.

By assessing one or more of the distances described above, the physician monitors the position of first bead 430A with respect to distal end 440 of second axial surface characteristic portion 106 (which defines second surface 104). During rotation of helical tissue-coupling element 30 into the tissue, first bead 430A reaches distal end 440 immediately before second axial surface characteristic portion 106 penetrates the surface of the tissue. Before further advancing the helical tissue-coupling element into the tissue, the physician may apply tension, such as described hereinbelow with reference to FIG. 7C, for example in order to assess whether the anchor is placed in an appropriate location for altering the geometry of the right atrium sufficiently to repair the tricuspid valve. If the location is found not to be appropriate, the physician may remove the anchor from the tissue and redeploy the anchor at another location. The anchor may generally be readily unscrewed from the tissue because second surface 104 did not yet enter the tissue.

If the location is found to be appropriate, the physician further advances helical tissue-coupling element 30 into tissue 530, as shown in FIG. 5C. As mentioned above, second bead 430B is initially positioned proximal to and near proximal end 550 of second axial surface characteristic portion 106 (as shown in FIGS. 5A and 5B). The physician uses second bead 430B to assess when the tissue-coupling element has been completely screwed into tissue 530. As helical tissue-coupling element 30 further penetrates and is advanced into the tissue, second bead 430B does not penetrate the tissue, and thus remains at surface 552 of the tissue, in contact therewith, as shown in FIG. 5C. As a result, as the tissue-coupling element advances into the tissue, second bead 430B remains stationary and slides along the tissue-coupling element toward proximal end 42 of anchor 520 (and toward head 40). Both second bead 430B and more proximal portions of the anchor (such as head 40) are viewed using imaging (e.g., fluoroscopy, computed tomography, echocardiography, sonography, or MRI), and the distance between second bead 430B and the proximal end of the anchor (e.g., the head), is estimated and monitored in real time as the anchor is advanced into the tissue. As shown in FIG. 5C, when second bead 430B reaches a desired distance from the head (such as reaches the head itself), the tissue-coupling element has been fully advanced, e.g., screwed, into and embedded in the tissue, and the physician thus ceases rotating the anchor.

Without using a technique such as this for visualizing the advancement of the anchor into the tissue, it is often difficult to ascertain when the tissue anchor has been fully embedded into the tissue, because the tissue is difficult to see in some images, such as fluoroscopic images. As a result, the tissue anchor may inadvertently be insufficiently advanced into the tissue, resulting in poor anchoring in the tissue, or over-advanced into the tissue, possible tearing or otherwise damaging the tissue.

For some applications, as shown in FIG. 5C, tissue anchor 520 is configured such that during advancement of the tissue anchor into tissue 530, first bead 430A is stopped at distal end 440 of second axial surface characteristic portion 106 from further proximal sliding by second surface 104. First bead 430A thus enters tissue 530 with the anchor as the anchor is further rotated and advanced into the tissue.

Alternatively, for other applications, as shown in FIG. 6, tissue anchor 520 is configured such that during advancement of the tissue anchor into tissue 530, first bead 430A remains at surface 552 of tissue 530 and slides over second axial surface characteristic portion 106. For these applications, second bead 430B is typically initially fixed at a proximal end of tissue-coupling element 30. As the tissue anchor is further advanced into the tissue, first and second beads 430A and 430B thus become positioned adjacent to each other, marking the desired penetration depth. (It may be easier for the physician to assess the distance between first and second beads 430A and 430B using imaging, than between first bead 430A and proximal end 42 (e.g., the head) of the anchor.)

For some applications, helical tissue-coupling element 30 is shaped so as define distal stopper 450, described hereinabove with reference to FIGS. 4A-B.

First and second beads 430A and 430B may have any appropriate shape, such as annular, e.g., a rectangle, e.g., square (as shown). Typically, the inner shape of the bead generally conforms with, and is slightly larger than, the outer cross-sectional shape of the helix at its greatest thickness.

Reference is now made to FIGS. 7A-D, which are schematic illustrations of a system 620 comprising a first tissue-engaging element 660a and a second tissue-engaging element 660b for repairing a tricuspid valve 604 of a heart 602 of a patient, in accordance with some applications of the present invention. First tissue-engaging element 660a comprises tissue anchor 20, tissue anchor 120, tissue anchor 220, tissue anchor 320, tissue anchor 420, or tissue anchor 520, described herein with reference to FIGS. 1A-B, 2A-B, 8A-C, 4A-B, 5A-B, and 6A-C and 7, respectively. By way of illustration and not limitation, in the configuration shown in FIGS. 7A-D, first tissue-engaging element 660a comprises tissue anchor 120, described hereinabove with reference to FIGS. 2A-B. First tissue-engaging element 660a is designated for implantation at least in part in cardiac tissue at a first implantation site 630. Second tissue-engaging element 660b comprises a stent 650 which is designated for implantation at a second implantation site 652 in a portion of a blood vessel, e.g., an inferior vena cava 608 (as shown) or a superior vena cava 610 (although not shown, can be implemented as described with reference to FIGS. 1E-G of PCT Publication WO 2011/089601, which is assigned to the assignee of the present application and is incorporated herein by reference). First and second tissue-engaging elements 660a and 660b are coupled together by flexible longitudinal member 118. For some applications, flexible longitudinal member 118 has a length of at least 10 mm, no more than 40 mm, and/or between 10 and 40 mm. For some applications, flexible longitudinal member 118 comprises a suture, wire, or cord.

Typically, a distance between first and second implantation sites 630 and 652 is adjusted by pulling to apply tension to or relaxing longitudinal member 118 and/or by applying tension to at least one of first and second tissue-engaging elements 660a and 660b. Responsively, a distance between the leaflets of tricuspid valve 604 is adjusted to reduce and eliminate regurgitation through valve 604, and thereby, valve 604 is repaired. For some applications, longitudinal member 118 is pulled or relaxed by manipulating second tissue-engaging element 660b, as is described hereinbelow.

First and second tissue-engaging elements 660a and 660b may be fabricated and/or comprise materials as described with reference to FIGS. 1A-G of the above-mentioned '601 publication. For some applications, second tissue-engaging element 660b comprises a stent 650 which is advanced toward and expandable in a portion of inferior vena cava 608 (such as shown in FIGS. 7A-D) or superior vena cava 610 (such as shown in FIGS. 1E-G of the above-mentioned '601 publication), i.e., a blood vessel that is in direct contact with a right atrium 606 of heart 602 of the patient. Second tissue-engaging element 660b is implanted at second implantation site 652. As shown, first implantation site 630 comprises a portion of an annulus of tricuspid valve 604. Implantation site 630 typically comprises a portion of the annulus of valve 604 that is between (1) the middle of the junction between the annulus and anterior leaflet 614, and (2) the middle of the junction between the annulus and posterior leaflet 616, e.g., between the middle of the junction between the annulus and anterior leaflet 614 and the commissure between the anterior and posterior leaflets. That is, first tissue-engaging element 660a is coupled to, e.g., screwed into, the fibrous tissue of the tricuspid annulus close to the commissure in between anterior leaflet 614 and posterior leaflet 616. Implantation site 630 is typically close to the mural side of valve 604. For such applications, the drawing together of first and second implantation sites 630 and 652 cinches valve 604 and may create a bicuspidization of tricuspid valve 604, and thereby achieve stronger coaptation between anterior leaflet 614 and septal leaflet 612.

For some applications, first implantation site 630 may include a portion of tissue of a wall defining right atrium 606 of heart 602, typically in a vicinity of the annulus of valve 604. For other applications, first implantation site 630 may include a portion of a wall of a right ventricle of heart 602, a ventricular portion of the annulus of valve 604, or a portion of a papillary muscle of the right ventricle of heart 602, as is shown hereinbelow in FIG. 6 of the above-mentioned '601 publication. First implantation site 630 is typically a distance away from, e.g., generally opposite, second implantation site 652 so that, following adjusting of longitudinal member 118, first and second implantation sites 630 and 652 are drawn together, and thereby at least first and second leaflets, e.g., all three leaflets, of valve 604 are drawn toward each other. For applications in which first implantation site 630 includes a portion of tissue of the annulus, the adjusting of the distance between implantation sites 630 and 652 alters the geometry of (i.e., changes the configuration of) the annulus of valve 604 and thereby draws together the leaflets of valve 604. For applications in which first implantation site 630 includes tissue of a portion of a wall that defines atrium 606, the adjusting of the distance between implantation sites 630 and 652 alters the geometry of (i.e., changes the configuration of) the wall of atrium 606 and thereby draws together the leaflets of valve 604.

Figure 7A:
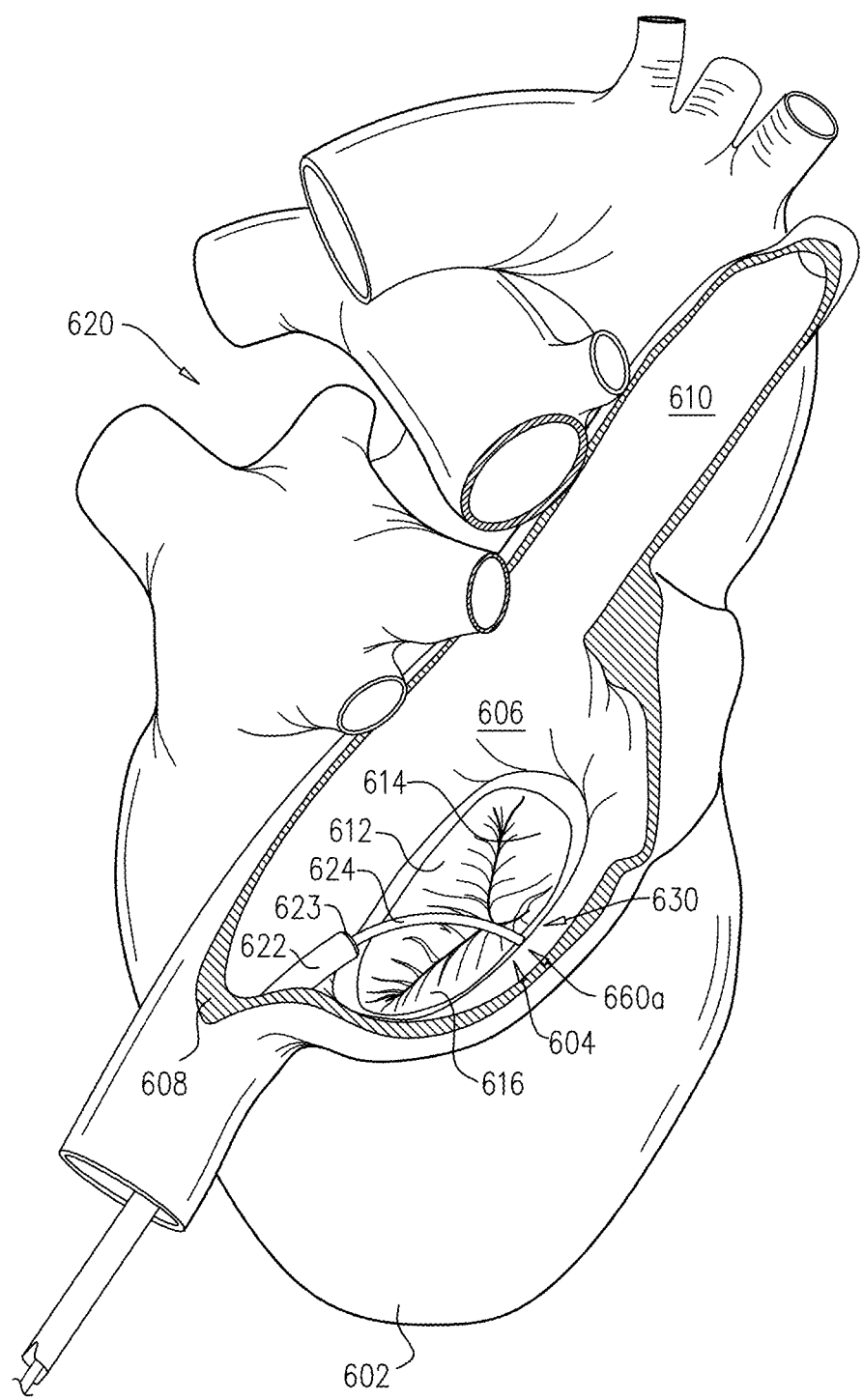
FIGS. 7A-D are schematic illustrations of a system comprising a first tissue-engaging element and a second tissue-engaging element for repairing a tricuspid valve, in accordance with some applications of the present invention.

FIG. 7A shows the advancement of a catheter 622 toward atrium 606 of the patient until a distal end 623 of the catheter is disposed within atrium 606, as shown. The procedure is typically performed with the aid of imaging, such as fluoroscopy, transesophageal echo, and/or echocardiography. For some applications, the procedure begins by advancing a semi-rigid guidewire into right atrium 606 of the patient. The guidewire provides a guide for the subsequent advancement of catheter 622 therealong and into the right atrium. Catheter 622 typically comprises a 14-20 F sheath, although the size may be selected as appropriate for a given patient. Catheter 622 is advanced through vasculature into right atrium 606 using a suitable point of origin typically determined for a given patient, such as described in the above-mentioned '601 publication.

Once distal end 623 of catheter 622 is disposed within atrium 606, an anchor-deployment tube 624 is extended from within catheter 622 beyond distal end 623 thereof and toward first implantation site 630. Anchor-deployment tube 624 holds first tissue-engaging element 660a and a distal portion of longitudinal member 118. For some applications, tube 624 is steerable, as is known in the catheter art, while for other applications, a separate steerable element may be coupled to anchor-deployment tube 624. Under the aid of imaging guidance, anchor-deployment tube 624 is advanced toward first implantation site 630 until a distal end thereof contacts cardiac tissue of heart 602 at first implantation site 630. Anchor-deployment tube 624 facilitates atraumatic advancement of first tissue-engaging element 660a toward first implantation site 630. For such applications in which anchor-deployment tube 624 is used, stent 650 is compressed within a portion of tube 624.

Figure 7B:
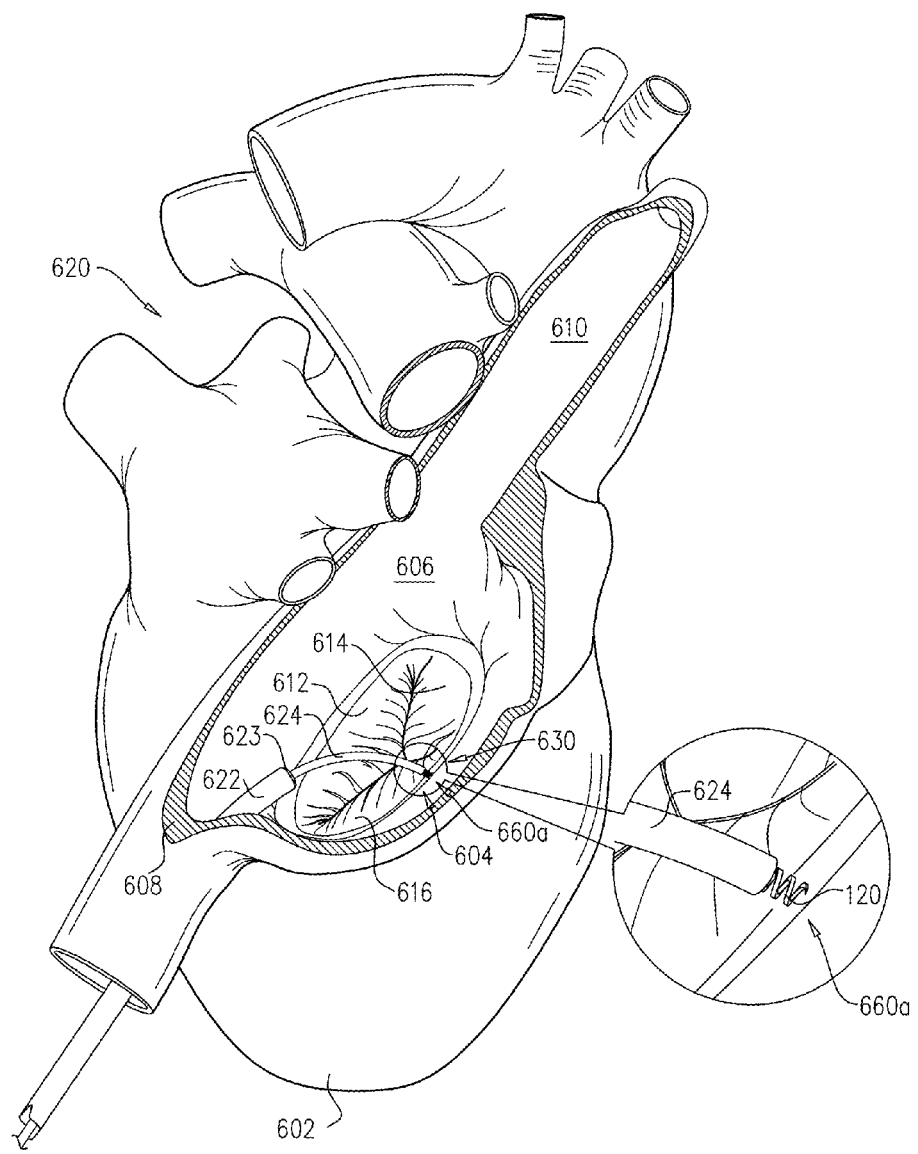

As shown in FIG. 7B, an anchor-manipulating tool (not shown for clarity of illustration), which is slidably disposed within anchor-deployment tube 624, is slid distally within tube 624 so as to push distally first tissue-engaging element 660a and expose first tissue-engaging element 660a from within tube 624. For some applications of the present invention, the anchor-manipulating tool is reversibly coupled to first tissue-engaging element 660a and facilitates implantation of first tissue-engaging element 660a in the cardiac tissue.

The physician rotates the anchor-manipulating tool from a site outside the body of the patient in order to rotate first tissue-engaging element 660a and thereby screw at least a portion of first tissue-engaging element 660a in the cardiac tissue. For applications in which tissue-engaging element 660a comprises tissue anchor 20, the physician typically advances second axial portion 62 (and third axial portion 64, if provided) completely into the cardiac soft tissue, and leaves at least a portion of (e.g., the entire) first axial portion 60 outside of the soft tissue. For applications in which tissue-engaging element 660a comprises tissue anchor 120, the physician typically advances single-helix portion 150 completely into the cardiac soft tissue, and leaves at least a portion of (e.g., the entire) double-helix portion 160 outside of the soft tissue. For applications in which tissue-engaging element 660a comprises tissue anchor 220, the physician typically advances second axial portion 262 (and third axial portion 264, if provided) completely into the cardiac soft tissue, and leaves at least a portion of (e.g., the entire) first axial portion 260 outside of the soft tissue.

Alternatively, system 620 is provided independently of the anchor-manipulating tool, and anchor-deployment tube 624 facilitates implantation of first tissue-engaging element 660a in the cardiac tissue. The physician rotates anchor-deployment tube 624 from a site outside the body of the patient in order to rotate first tissue-engaging element 660a and thereby screw at least a portion of first tissue-engaging element 660a in the cardiac tissue.

For applications in which first tissue-engaging element 660a comprises tissue anchor 320, tissue anchor 420, or tissue anchor 520, described hereinabove with reference to FIGS. 3A-F, 4A-B, and 5A-C and 6, respectively, the physician visualizes the respective radiopaque beads to aid with proper advancement of the anchor into the tissue.

Figure 7C:
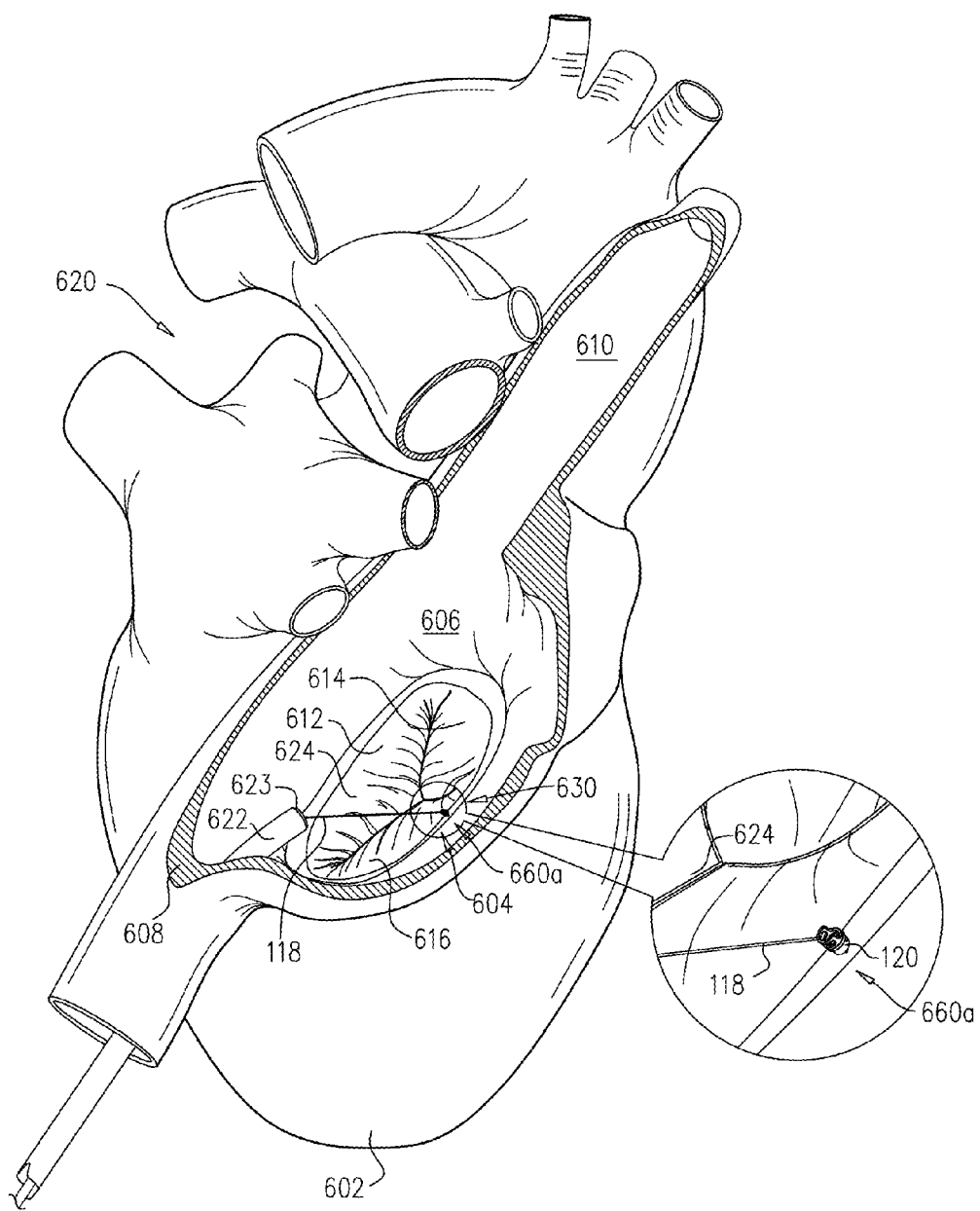

As shown in FIG. 7C, following the implantation of first tissue-engaging element 660a at first implantation site 630, anchor-deployment tube 624 is retracted within catheter 622 in order to expose longitudinal member 118. Subsequently, longitudinal member 118 is tensioned in order to repair tricuspid valve 604, as described hereinbelow.

For some applications, prior to pulling the portion of longitudinal member 118 that is disposed between first tissue-engaging element 660a and distal end 623 of catheter 622, a mechanism that facilitates the application of a pulling force to longitudinal member 118 is fixed in place, as described in the above-mentioned '601 publication.

For some applications, catheter 622 is reversibly coupled to a proximal portion of longitudinal member 118 by being directly coupled to the proximal portion of member 118 and/or catheter 622 is reversibly coupled to second tissue-engaging element 60b. For example, catheter 622 may be reversibly coupled to stent 650 by the stent's application of a radial force against the inner wall of catheter 622 because of the tendency of stent 650 to expand radially. Following implantation of first tissue-engaging element 660a, catheter 622 (or an element disposed therein) is then pulled proximally to apply tension to longitudinal member 118, which, in such an application, functions as a tensioning element. For some applications, catheter 622 pulls on second tissue-engaging element 660b in order to pull longitudinal member 118. For other applications, catheter 622 pulls directly on longitudinal member 118. For yet other applications, a pulling mechanism pulls on longitudinal member 118, as is described with reference to FIGS. 7A-D in the above-referenced '601 publication.

Pulling longitudinal member 118 pulls taut the portion of longitudinal member 118 that is disposed between first tissue-engaging element 660a and distal end 623 of catheter 622. Additionally, longitudinal member 118 may be pulled or relaxed in order to adjust the distance between first and second implantation sites 630 and 652. Responsively to the pulling of longitudinal member 118, at least the anterior and septal leaflets of tricuspid valve 604 are drawn together because the geometry of the annulus and/or of the wall of atrium 606 is altered in accordance with the pulling of longitudinal member 118 and depending on the positioning of first tissue-engaging element 660a.

For some applications, during the pulling of longitudinal member 118 by catheter 622, a level of regurgitation of tricuspid valve 604 is monitored. Longitudinal member 118 is pulled until the regurgitation is reduced or ceases.

For applications in which first tissue-engaging element 660a comprises tissue anchor 20, described hereinabove with reference to FIGS. 1A-B, if the physician applies too much tension when pulling longitudinal member 118, helical tissue-coupling element 30 generally elongates along first axial portion 60 before along second axial portion 62, such that first axial portion 60 serves as a mechanical fuse. Providing first axial portion 60 effectively reduces the force on the main part of the anchor (e.g., second axial portion 62) which holds the anchor in place, thereby reducing or eliminating the danger of unscrewing the anchor, breaking the anchor, or tearing the tissue, both during the implantation procedure and thereafter during long-term implantation of the anchor. Alternatively or additionally, the physician may reduce or cease increasing the tension before second axial portion 62 elongates, thereby reducing the risk of the elongation causing damage to the tissue in which second axial portion 62 is implanted, and the risk that the tension will pull the anchor from the tissue. For some applications, the physician senses elongation of first axial portion 60 in real time while applying the tension, such as using imaging (e.g., fluoroscopy, computed tomography, echocardiography, sonography, or MRI) and/or tactile feedback.

For applications in which first tissue-engaging element 660a comprises tissue anchor 120, described hereinabove with reference to FIGS. 2A-B, if the physician applies too much tension when pulling longitudinal member 118, helical tissue-coupling element 130 generally elongates along shaftless double-helix axial portion 160 before along single-helix axial portion 150, and thus can be considered to serve as a mechanical fuse. Providing shaftless double-helix axial portion 160 effectively reduces the force on shaftless single-helix axial portion 150 which holds the anchor in place, thereby reducing or eliminating the danger of unscrewing the anchor, breaking the anchor, or tearing the tissue, both during the implantation procedure and thereafter during long-term implantation of the anchor. Alternatively or additionally, the physician may reduce or cease increasing the tension before single-helix axial portion 150 elongates, thereby reducing the risk of the elongation causing damage to the tissue in which single-helix axial portion 150 is implanted, and the risk that the tension will pull the anchor from the tissue. For some applications, the physician senses elongation of shaftless double-helix axial portion 160 in real time while applying the tension, such as using imaging (e.g., fluoroscopy, computed tomography, echocardiography, sonography, or MRI) and/or tactile feedback.

For some applications in which first tissue-engaging element 660a comprises tissue anchor 420 or tissue anchor 520, described hereinabove with reference to FIGS. 4A-B and FIGS. 5A-C and 6, respectively, the physician may monitor the location of the bead during implantation of the anchor as described with reference to FIG. 7B, and cease advancing the anchor once the bead reaches distal end 440 immediately before second axial surface characteristic portion 106 penetrates the surface of the tissue. Before further advancing the helical tissue-coupling element into the tissue, the physician may apply tension, in order to assess whether the anchor is placed in an appropriate location for altering the geometry of the right atrium sufficiently to repair the tricuspid valve. If the location is found not to be appropriate, the physician may remove the anchor from the tissue and redeploy the anchor at another location. The anchor may generally be readily unscrewed from the tissue because second surface 104 did not yet enter the tissue. If the location is found to be appropriate, the physician further advances the helical tissue-coupling element into the tissue, optionally using the bead to assess when the tissue-coupling element has been completely screwed into the tissue.

Once the physician determines that the regurgitation of valve 604 is reduced or ceases, and valve 604 has been repaired, the physician decouples catheter 622 from second tissue-engaging element 660b disposed therein and/or from longitudinal member 118, and then retracts catheter 622 in order to expose second tissue-engaging element 660b, i.e., stent 650. During the advancement of catheter 622 toward atrium 606, stent 650 is disposed within a distal portion of catheter 622 in a compressed state. Following initial retracting of catheter 622, stent 650 is exposed and is allowed to expand and contact a wall of inferior vena cava 608.

Figure 7D:
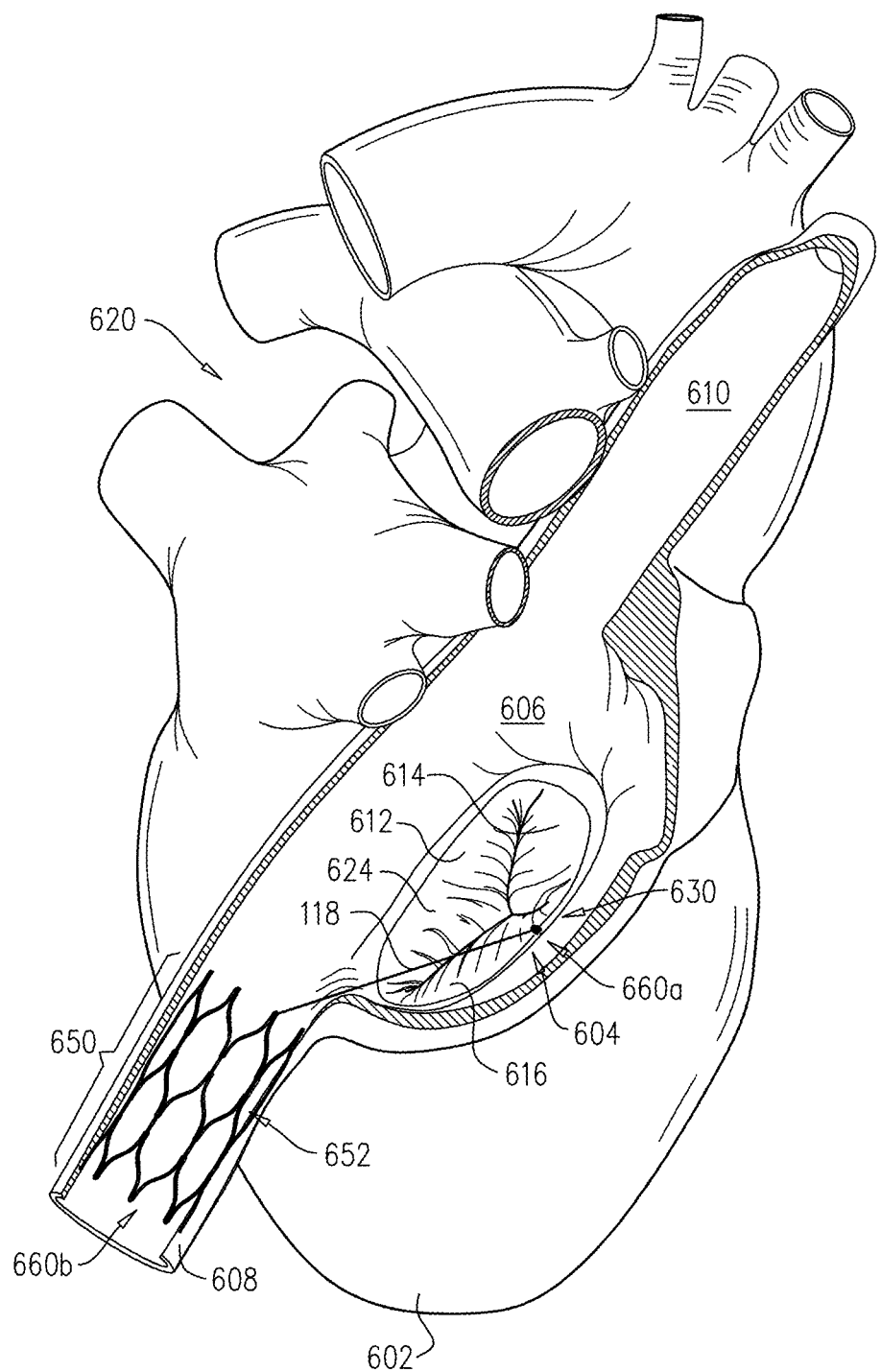

FIG. 7D shows the stent fully exposed and fully expanded. Responsively to the expanding, stent 650 is implanted in second implantation site 652 and maintains the tension of longitudinal member 118 on first tissue-engaging element 660a and thereby on the portion of cardiac tissue to which first tissue-engaging element 660a is coupled.

The techniques described with reference to FIGS. 7A-B may be performed in combination with techniques described in the above-mentioned '601 publication, *mutatis mutandis*.

Reference is now made to FIGS. 8A-C, which are schematic illustrations of a tissue anchor 220, in accordance with respective applications of the present invention. FIG. 8A is an isometric view of the anchor, and FIG. 8B is a cross-sectional view taken along line VIIIB-VIIIB of FIG. 8A. FIG. 8C is an isometric view of another configuration of the anchor, which is described hereinbelow. Tissue anchor 220 comprises a helical tissue-coupling element 230 disposed about a longitudinal axis 232 thereof and having a distal tissue-penetrating tip 234 at a distal end 236 of tissue anchor 220. Typically, tissue anchor 220 is shaped so as to define a head 240 at a proximal end 242 thereof.

Helical tissue-coupling element 230 comprises a wire 254 shaped as a helix 256. Wire 254 has a non-circular cross section 264, which is typically shaped as a polygon, such as a quadrilateral, e.g., a rectangle 266, for example a square as shown in FIG. 8B, or as an ellipse. During manufacture, wire 254 is twisted about its longitudinal axis, so as to define a ridged surface. The wire, thus twisted, is formed into helix 256, as shown in FIGS. 8A-B. The ridged surface helps anchor the tissue-coupling element in soft tissue, such as cardiac tissue. For some applications, the wire is twisted about its longitudinal axis at least 1 (e.g., at least 2) twists per cm, no more than 5 twists per cm, and/or between 1 and 5, e.g., 2 and 5, twists per cm of the length of wire 254 (the strut) while the strut is straight (i.e., before curved into the helix).

For applications in which the cross-section is shaped as rectangle 266, each of a length L3 and width W thereof is typically between 0.3 and 0.8 mm. For some applications, first axial portion 260 extends to head 240. (The cross section mentioned above with reference to FIGS. 1A-B in analogous to cross section 264.)

Typically, helical tissue-coupling element 230 has an axial length L2 that is at least 3 mm, no more than 20 mm (e.g., no more than 10 mm), and/or between 3 mm and 20 mm, such as 10 mm. Typically, helical tissue-coupling element 230 is shaped so as to define and radially surround an empty space 252 that extends along at least 75% of axial length L2. In other words, the helical tissue-coupling element typically is not shaped so as to define a shank or shaft.

Typically, wire 254 comprises a metal, such as standard implantable alloys known in the art of biomedical implants, such as those described in ISO 5832 parts 1-14.

For some applications, helical tissue-coupling element 230 has:
- a first axial stiffness along a first axial portion 260 of a shaftless helical portion 250 of helical tissue-coupling element 230,
- a second axial stiffness along a second axial portion 262 of shaftless helical portion 250 of helical tissue-coupling element 230 that is more distal than first axial portion 260), which second axial stiffness is greater than the first axial stiffness, and
- optionally, a third axial stiffness along a third axial portion 264 of shaftless helical portion 250 of helical tissue-coupling element 30 that is more distal than second axial portion 262), which third axial stiffness is less than the second axial stiffness (the third axial stiffness may be equal to or different from the first axial stiffness).

For some applications, the second axial stiffness is at least 120% of the first axial stiffness. For some applications, the first axial stiffness is between 2 and 100 N/mm, and/or the second axial stiffness is between 3 and 200 N/mm. For some applications, the second axial stiffness is at least 120% of the third axial stiffness. For some applications, the third axial stiffness is between 2 and 100 N/mm.

These varying axial stiffnesses may be achieved by varying the number of twists per cm of the length the wire before it is shaped into the helix; axial portions having a greater number of twists per cm are stiffer. Alternatively or additionally, these varying axial stiffnesses may be achieved by varying the thickness of the struts, the chemical composition, and/or by treating the different axial portions, for example with different thermal treatments along the helix.

For some applications, helical tissue-coupling element 230 has:
- a first axial yield strength along a first axial portion 260 of a shaftless helical portion 250 of helical tissue-coupling element 230,
- a second axial yield strength along a second axial portion 262 of shaftless helical portion 250 of helical tissue-coupling element 230 that is more distal than first axial portion 260), which second axial yield strength is greater than the first axial yield strength, and
- optionally, a third axial yield strength along a third axial portion 264 of shaftless helical portion 250 of helical tissue-coupling element 30 that is more distal than second axial portion 262), which third axial yield strength is less than the second axial yield strength (the third axial yield strength may be equal to or different from the first axial yield strength).

For some applications, the second axial yield strength is at least 120% of the first axial yield strength. For some applications, the first axial yield strength is between 5 and 15 N, and/or the second axial yield strength is between 6 and 30 N. For some applications, the second axial yield strength is at least 120% of the third axial yield strength. For some applications, the third axial yield strength is between 5 and 15 N.

These varying axial yield strengths may be achieved by varying the number of twists per cm of the length the wire before it is shaped into the helix; axial portions having a greater number of twists per cm are stiffer. Alternatively or additionally, these varying axial stiffnesses may be achieved by varying the thickness of the struts, the chemical composition, and/or by treating the different axial portions, for example with different thermal treatments along the helix.

One result of these differing axial stiffnesses and/or yield strengths is that if excessive tension is applied to head 240 at proximal end 242 of anchor 220, helical tissue-coupling element 230 generally elongates along first axial portion 260 before along second axial portion 262, such that first axial portion 260 serves as a mechanical fuse. As described hereinabove with reference to FIG. 7C, providing first axial portion 260 effectively reduces the force on the main part of the anchor (e.g., second axial portion 262) which holds the anchor in place, thereby reducing or eliminating the danger of unscrewing the anchor, breaking the anchor, or tearing the tissue, both during the implantation procedure and thereafter during long-term implantation of the anchor. Alternatively or additionally, the physician may reduce or cease increasing the tension before second axial portion 262 elongates, thereby reducing the risk of the elongation causing damage to the tissue in which second axial portion 262 is implanted, and the risk that the tension will pull the anchor from the tissue. For some applications, the physician monitors, such as using imaging (e.g., fluoroscopy, computed tomography, echocardiography, sonography, or MRI), the length of first axial portion 260 in real time while applying the tension, in order to sense elongation of first axial portion 260. Alternatively or additionally, the physician may sense the elongation using tactile feedback. Typically, first axial portion 260 undergoes plastic deformation when elongated. As a result, excess force applied to the anchor is absorbed by first axial portion 260, instead of detaching the anchor from the tissue, or causing failure elsewhere on the anchor.

For some applications, the axial stiffness of helical tissue-coupling element 230 varies generally continuously along at least an axial portion of the helical tissue-coupling element, such that helical tissue-coupling element 230 has (a) the first axial stiffness at only a single axial location along first axial portion 260, (b) the second axial stiffness at only a single axial location along second axial portion 262, and/or (c) the third axial stiffness at only a single axial location along third axial portion 264.

Alternatively or additionally, the axial stiffness of helical tissue-coupling element 230 is constant along one or more axial portions of the helical tissue-coupling element, such that helical tissue-coupling element 230 has (a) the first axial stiffness at a plurality of axial locations along first axial portion 260, (b) the second axial stiffness at a plurality of axial locations along second axial portion 262, and/or (c) the third axial stiffness at a plurality of axial locations along third axial portion 264.

For some applications, the axial yield strength of helical tissue-coupling element 230 varies generally continuously along at least an axial portion of the helical tissue-coupling element, such that helical tissue-coupling element 230 has (a) the first axial yield strength at only a single axial location along first axial portion 260, (b) the second axial yield strength at only a single axial location along second axial portion 262, and/or (c) the third axial yield strength at only a single axial location along third axial portion 264.

Alternatively or additionally, the axial yield strength of helical tissue-coupling element 230 is constant along one or more axial portions of the helical tissue-coupling element, such that helical tissue-coupling element 230 has (a) the first axial yield strength at a plurality of axial locations along first axial portion 260, (b) the second axial yield strength at a plurality of axial locations along second axial portion 262, and/or (c) the third axial yield strength at a plurality of axial locations along third axial portion 264.

Reference is made to FIG. 8C. As mentioned above, the varying axial yield strengths and/or axial stiffnesses of the different axial portions of helical tissue-coupling element 230 may be achieved by varying the number of twists per cm of the length the wire before it is shaped into the helix. For some applications, first axial portion 260 is not twisted (i.e., has zero twists per cm) in order to provide this axial portion with its relatively low axial yield strength and/or axial stiffness. For some applications, all or a portion of third axial portion 264, e.g., the tip, is ground smooth.

Reference is now made to FIGS. 9A-B and 10A-B, which are schematic illustrations of two configurations of a delivery system 700, in accordance with respective applications of the present invention. Delivery system 700 is used to deliver first tissue-engaging element 660a, and be implemented in combination with the techniques described hereinabove with reference to FIGS. 7A-D. First tissue-engaging element 660a comprises tissue anchor 20, tissue anchor 120, or tissue anchor 220, described hereinabove with reference to FIGS. 1A-B, 2A-B, and 8A-C, respectively, or another tissue anchor that is known in the art (which is optionally inserted by rotation). By way of illustration and not limitation, in the configuration shown in FIGS. 9A-B and 10A-B, first tissue-engaging element 660a comprises tissue anchor 20, described hereinabove with reference to FIGS. 1A-B. First tissue-engaging element 660a is designated for implantation at least in part in cardiac tissue at first implantation site 630, as described hereinabove with reference to FIGS. 7A-B.

Delivery system 700 comprises anchor-deployment tube 624, described hereinabove with reference to FIGS. 7A-D.

Figure 9A:
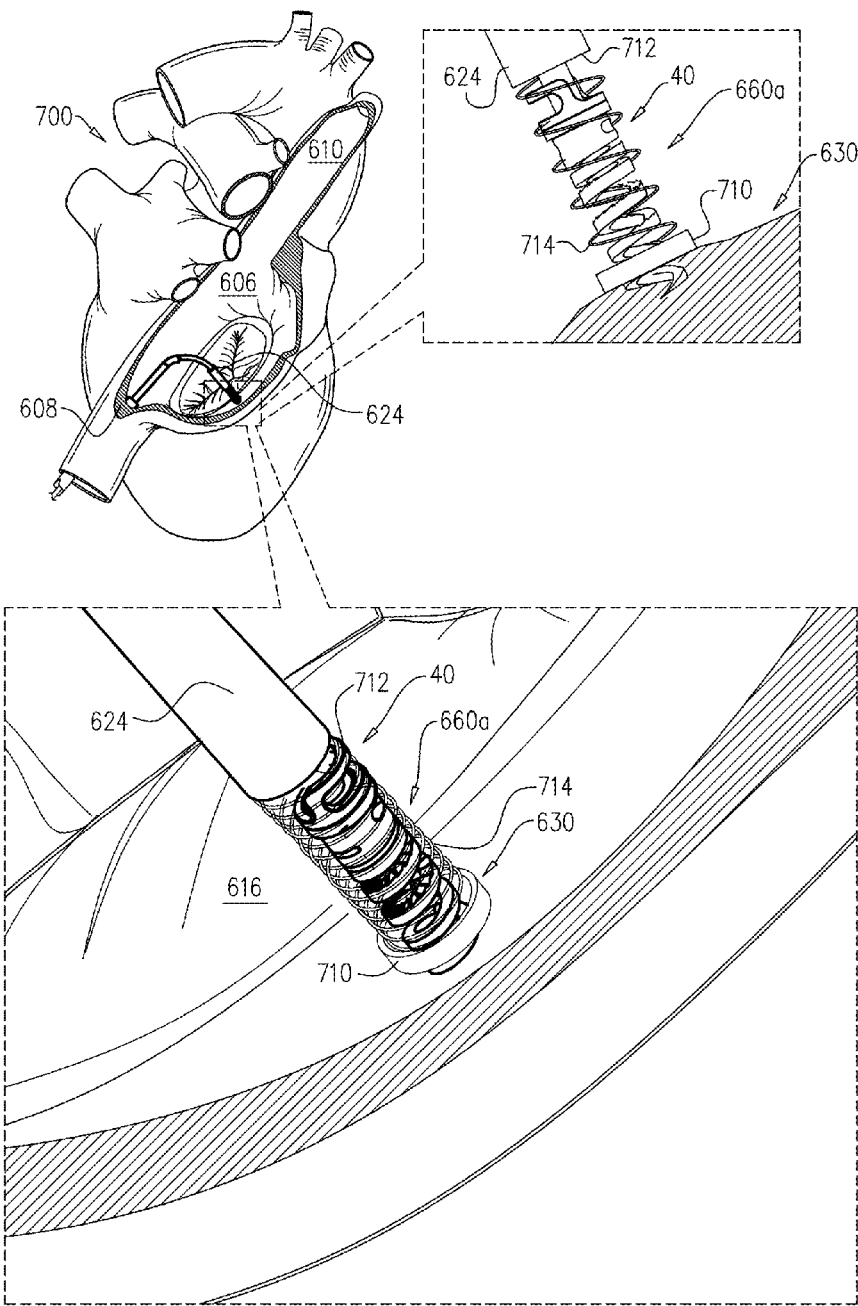
FIGS. 9A-B and 10A-B are schematic illustrations of two configurations of a delivery system, in accordance with respective applications of the present invention.
Figure 9B:
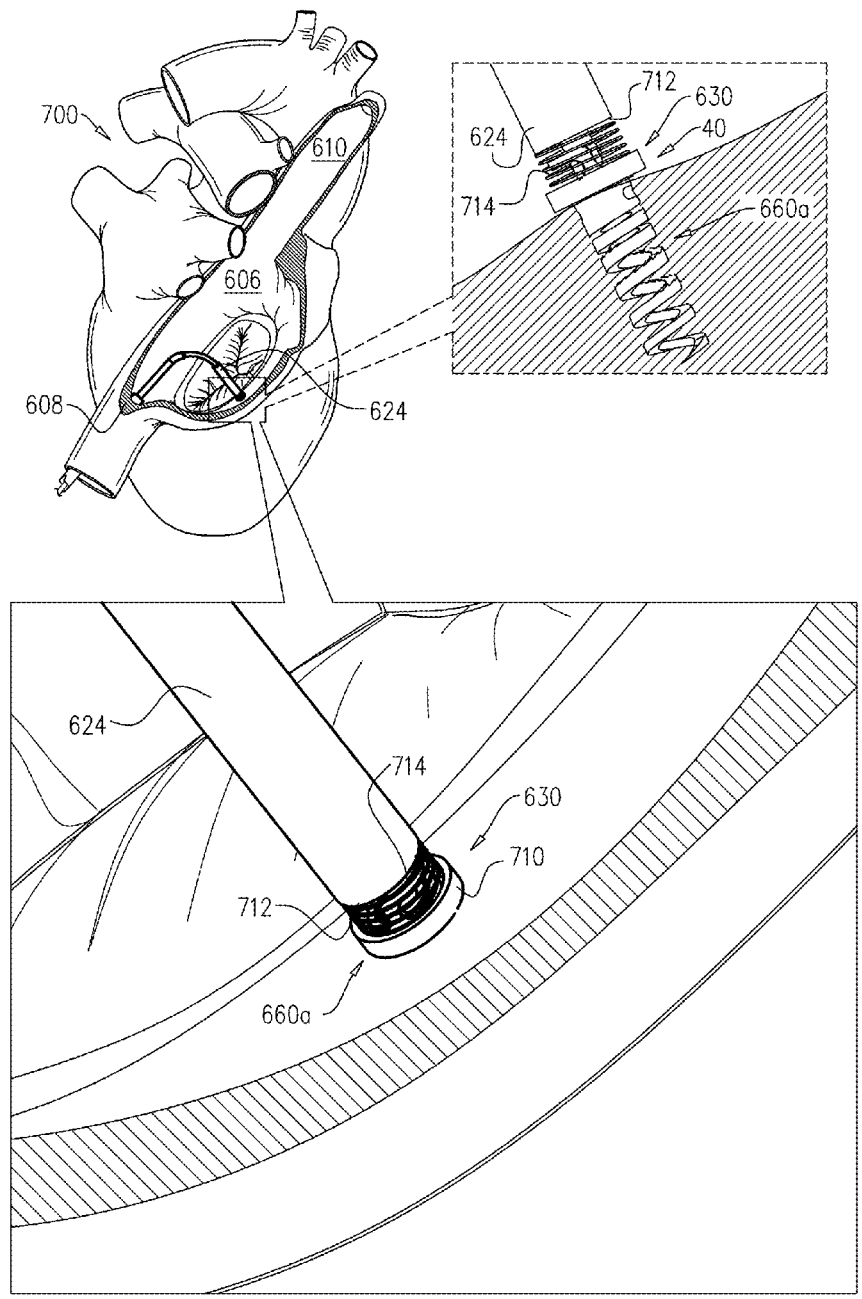
Figure 10A:
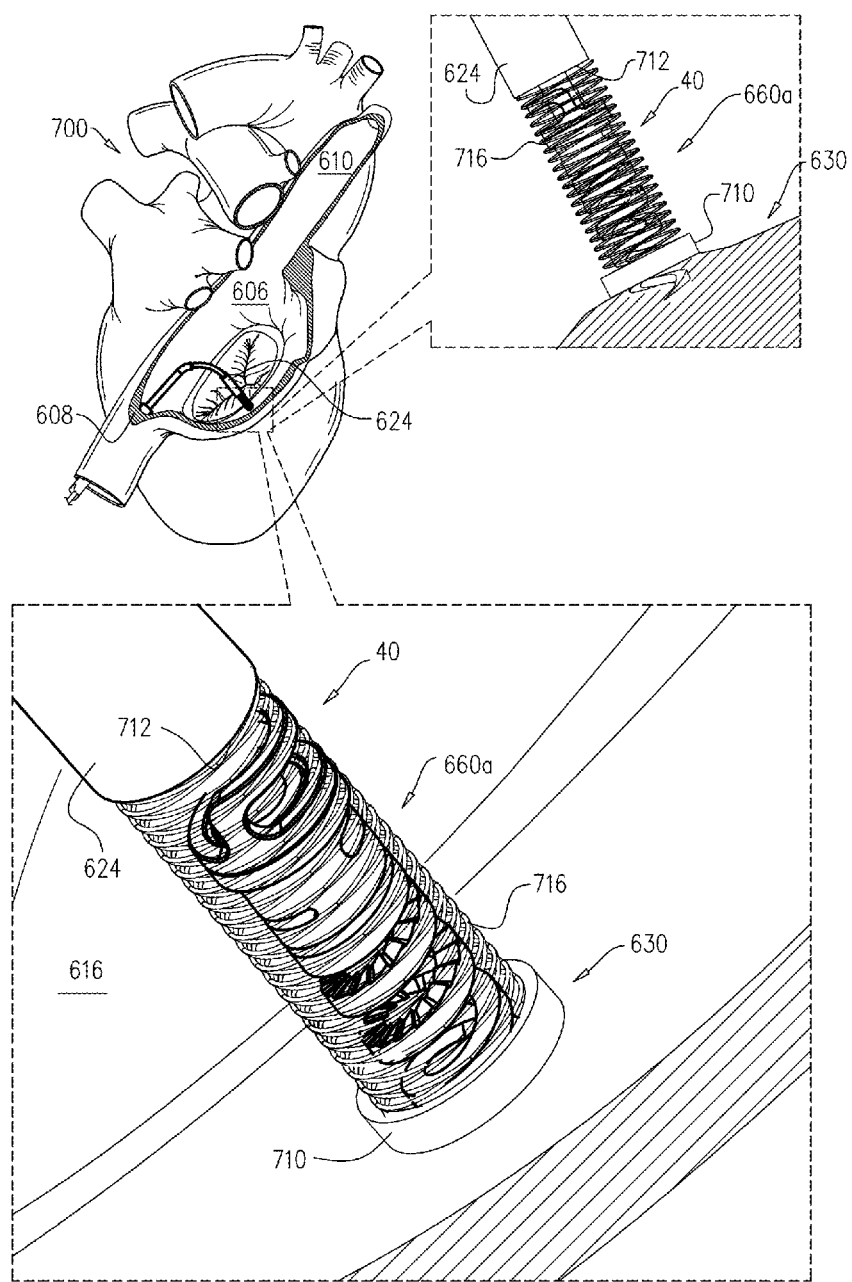
Figure 10B:
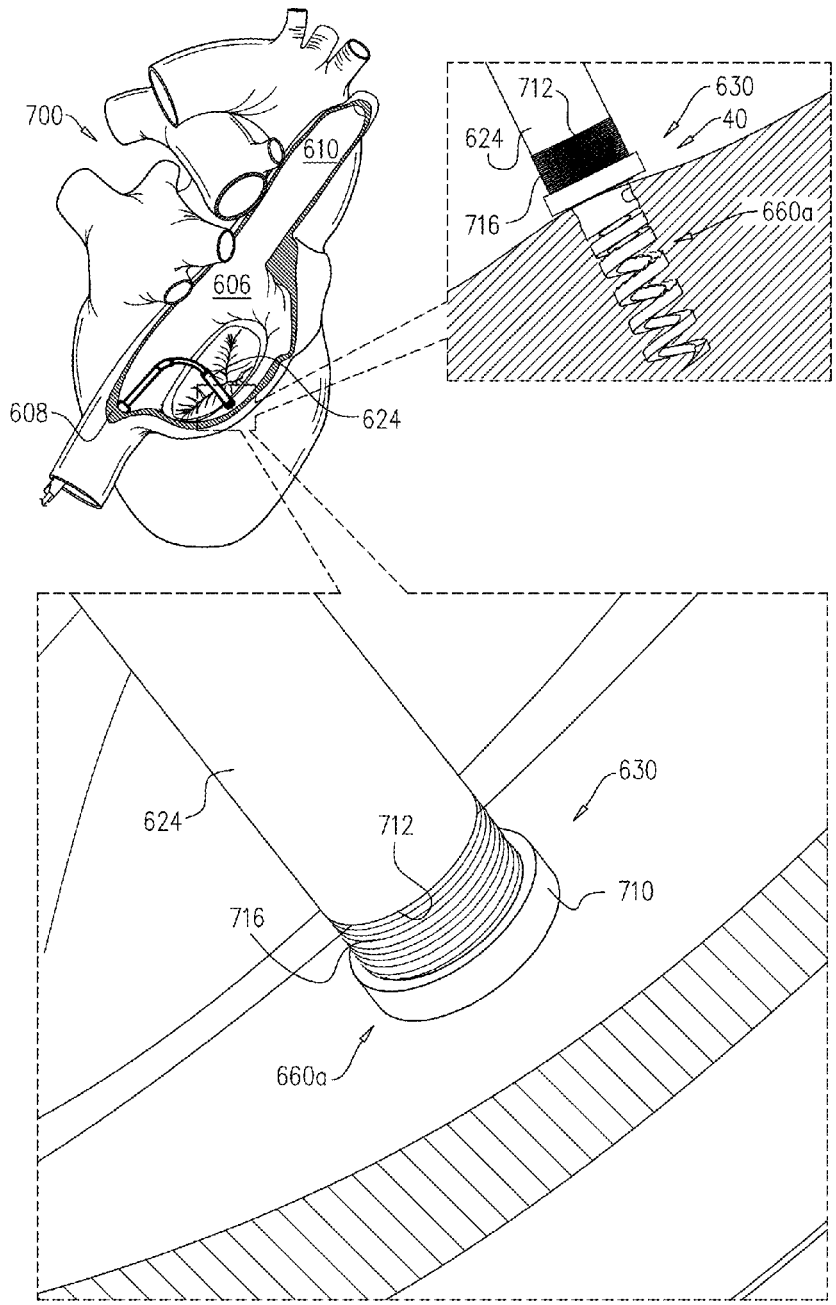

Delivery system 700 further comprises a radiopaque marker 710, which is coupled to a distal end 712 of anchor-deployment tube 624, such as by a flexible connecting element, such as a spring 714, as shown in FIGS. 9A-B, a braid 716, as shown in FIGS. 10A-B, a mesh, or a cut tube. Radiopaque marker 710, and the flexible connecting element (spring 714, braid 716, the mesh, or the cut tube) are initially arranged radially surrounding first tissue-engaging element 660a, such that radiopaque marker 710 is axially moveable along first tissue-engaging element 660a with respect to distal end 712. An inner diameter of radiopaque marker 710 is slightly larger than an outer diameter of first tissue-engaging element 660a. The flexible connecting element (spring 714, braid 716, the mesh, or the cut tube) axially compresses as marker 710 moves toward distal end 712. The flexible connecting element (spring 714, braid 716, the mesh, or the cut tube) biases the marker distally. Marker 710 may have any appropriate shape, such as a disc.

For applications in which braid 716 is provided, as shown in FIGS. 10A-B, the braid comprises biocompatible alloys such as St.St., Co.Cr., Titanium, NiTi or similar, or stiff polymers such as PEEK, PEKK or similar.

For some applications, radiopaque marker 710 is coupled to distal end 712 of anchor-deployment tube 624 by both spring 714 and braid 716 (configuration not shown). The braid radially surrounds the spring, and helps ensure that the spring remains straight, rather than bulging radially outward.

As shown in FIGS. 9A and 10A, as the physician begins to rotate first tissue-engaging element 660a into tissue at first implantation site 630, spring 714 or braid 716 (or the mesh or the cut tube) pushes marker 710 distally against the surface of the tissue. Marker 710 does not penetrate the tissue, and thus remains at the surface of the tissue, in contact therewith. As a result, as the physician continues to rotate element 660a further into the tissue, the surface of the tissue holds marker 710 in place, bringing marker 710 closer to distal end 712 of anchor-deployment tube 624 and closer to head 40 of element 660a.

Both marker 710 and more proximal portions of the anchor (such as head 40) are viewed using imaging (e.g., fluoroscopy, computed tomography, echocardiography, sonography, or MRI), and the distance between the marker and the proximal end of the anchor (e.g., the head) is estimated and monitored in real time as the anchor is advanced into the tissue. When the marker reaches a desired distance from the head (such as reaches the head itself), the tissue-coupling element has been fully advanced, e.g., screwed, into and embedded in the tissue, and the physician thus ceases rotating the anchor.

Alternatively or additionally, anchor-deployment tube 624 comprises one or more radiopaque markers near distal end 712 thereof.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

U.S. application Ser. No. 12/692,061, filed Jan. 22, 2010, which published as US Patent Application Publication 2011/0184510;

International Application PCT/IL2011/000064, filed Jan. 20, 2011, which published as PCT Publication WO 2011/089601;

U.S. application Ser. No. 13/188,175, filed Jul. 21, 2011, which published as US Patent Application Publication 2012/0035712;

U.S. application Ser. No. 13/485,145, filed May 31, 2012, entitled, "Locking concepts," which published as US Patent Application Publication 2013/0325115;

U.S. application Ser. No. 13/553,081, filed Jul. 19, 2012, entitled, "Method and apparatus for tricuspid valve repair using tension," which published as US Patent Application Publication 2013/0018459; and International Application PCT/IL2012/000282, filed Jul. 19, 2012, entitled, "Method and apparatus for tricuspid valve repair using tension," which published as PCT Publication WO 2013/011502.

In particular, the tissue anchors described herein may be used as one or more of the tissue anchors (e.g., the helical tissue anchors) described in the above-listed applications, in combination with the other techniques described therein.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
a tissue anchor, which (a) comprises a helical tissue-coupling element which has a distal tissue-penetrating tip at a distal end of the tissue anchor, and which is configured to be advanced into soft tissue, and (b) is shaped so as to define a longitudinal channel extending from a proximal end of the anchor to the distal end of the tissue anchor; and
a depth-finding tool, which comprises:
a radiopaque bead, which is shaped so as to define a hole therethrough, and which is positioned within the channel and is axially moveable along the channel so as to serve as a marker indicating a depth of penetration of the tissue-coupling element into the soft tissue; and
a shaft that is removably positioned within the channel, such that the shaft passes through the hole of the radiopaque bead, and such that the radiopaque bead is axially moveable along the shaft and along the channel.

2. The apparatus according to claim 1, wherein the helical tissue-coupling element is shaped so as to define a distal stopper that prevents the radiopaque bead from exiting from the distal end of the tissue anchor.

3. The apparatus according to claim 1, wherein the depth-finding tool further comprises a wire, which is at least partially disposed within the channel, and which couples the radiopaque bead to the a proximal portion of the tissue anchor, thereby preventing the radiopaque bead from exiting the distal end of the tissue anchor.

4. The apparatus according to claim 1, wherein a distal tip of the shaft is sharp.

5. A method comprising:
providing a tissue anchor, which (a) includes a helical tissue-coupling element which has a distal tissue-penetrating tip at a distal end of the tissue anchor, and which is configured to be advanced into soft tissue, and (b) is shaped so as to define a longitudinal channel extending from a proximal end of the anchor to the distal end of the tissue anchor;

providing a depth-finding tool, which includes (a) a radiopaque bead, which is shaped so as to define a hole therethrough, and is axially moveable along the channel so as to serve as a marker indicating a depth of penetration of the tissue- coupling element into the soft tissue, and (b) a shaft that is removably positioned within the channel, such that the shaft passes through the hole of the radiopaque bead, and such that the radiopaque bead is axially moveable along the shaft and along the channel;

advancing the helical tissue-coupling element into the soft tissue, such that the radiopaque bead comes into contact with and remains at a surface of the soft tissue so as to serve as a marker indicating the depth of penetration of the tissue- coupling element into the soft tissue; and proximally withdrawing the shaft from the channel, leaving the radiopaque bead in the channel.

6. The method according to claim 5, further comprising:
viewing the radiopaque bead and a proximal portion of the soft tissue anchor using imaging; and
assessing the depth of penetration of the helical tissue-coupling element into the soft tissue by estimating a distance between the radiopaque bead and the proximal portion of the tissue anchor.

7. The method according to claim 5, wherein proximally withdrawing the shaft from the channel comprises proximally withdrawing the shaft from the channel after finishing advancing the helical tissue-coupling element into the soft tissue.

8. The method according to claim 5, wherein a distal tip of the shaft is sharp, and wherein the method further comprises, before advancing the helical tissue- coupling element into the soft tissue, inserting the sharp distal tip of the shaft into the soft tissue slightly, in order to prevent sliding of the depth-finding tool and the anchor on a surface of the soft tissue before advancing the anchor into the tissue.

9. The method according to claim 5, wherein a distal tip of the shaft is sharp, and wherein the method further comprises advancing the shaft into the soft tissue while advancing the helical tissue-coupling element into the soft tissue.

10. The method according to claim 5, wherein the helical tissue-coupling element is shaped so as to define a distal stopper that prevents the radiopaque bead from exiting from the distal end of the tissue anchor.

11. The method according to claim 5, wherein the depth-finding tool further includes a wire, which is at least partially disposed within the channel, and which couples the radiopaque bead to the a proximal portion of the tissue anchor, thereby preventing the radiopaque bead from exiting the distal end of the tissue anchor.

* * * * *